United States Patent [19]
Corbett et al.

[11] Patent Number: 6,124,302
[45] Date of Patent: *Sep. 26, 2000

[54] 4,4-DISUBSTITUTED-3,4-DIHYDRO-2(1H)-QUINAZOLINONES USEFUL AS HIV REVERSE TRANSCRIPTASE INHIBITORS

[75] Inventors: Jeffrey W. Corbett, Haddon Height, N.J.; Soo S. Ko, Hockessin, Del.

[73] Assignee: DuPont Pharmaceuticals, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 09/056,820

[22] Filed: Apr. 8, 1998

Related U.S. Application Data

[60] Provisional application No. 60/043,115, Apr. 9, 1997, and provisional application No. 60/071,322, Jan. 14, 1998.

[51] Int. Cl.[7] .................... C07D 401/06; C07D 403/06; A61K 31/517

[52] U.S. Cl. .................... 514/259; 514/235.8; 514/252.1; 514/252.02; 514/241; 514/222.5; 544/284; 544/286; 544/5; 544/116; 544/257; 544/264; 544/238; 544/8; 544/180

[58] Field of Search .................... 514/259, 235.8, 514/252.1, 252.02, 241, 222.5; 544/286, 284, 116, 238

[56] References Cited

U.S. PATENT DOCUMENTS

| | | | |
|---|---|---|---|
| 3,660,322 | 5/1972 | Bernardi et al. | 260/251 |
| 4,099,002 | 7/1978 | Inaba et al. | 544/119 |
| 5,037,829 | 8/1991 | Freyne et al. | 514/259 |
| 5,434,152 | 7/1995 | Huffman et al. | 514/234.5 |
| 5,457,201 | 10/1995 | Yasuda et al. | 544/284 |
| 5,519,021 | 5/1996 | Young et al. | 514/230.5 |

FOREIGN PATENT DOCUMENTS

| | | |
|---|---|---|
| 0530994 | 3/1993 | European Pat. Off. |
| 0569083 | 11/1993 | European Pat. Off. |
| 0582455 | 2/1994 | European Pat. Off. |
| 4320347 | 12/1994 | Germany . |
| 9304047 | 3/1993 | WIPO . |
| 9512583 | 5/1995 | WIPO . |
| 9513273 | 5/1995 | WIPO . |

OTHER PUBLICATIONS

Huffman et al., *J. Org. Chem*, 1995, 60, 1590–1594, "Lithium Alkoxides of Cinchona Alkaloids as Chiral Controllers for Enantioselective Acetylide Addition to Cyclic N–Acyl Ketimines".

Tucker et al., *J. Med. Chem*, 1994, 37, 2437–2444, "Synthesis of a Series of 4–(Arylethynyl)–6–chloro–4–cyclopropyl–3, 4–dihydroquinazolin–2 (1H)–ones as Novel Non–nucleoside HIV–1 Reverse Transcriptase Inhibitors".

Houpis et al., *Tetrahedron Letters*, 1994, 35, 6811–6814, "Synthesis of a New Generation Reverse Transcriptase Inhibitor via the BCl$_3$/GaCl$_3$–induced Condensation of Anilines with Nitriles (Sugasawa Reaction) ".

*Primary Examiner*—John M. Ford
*Attorney, Agent, or Firm*—David H. Vance; Mary K. VanAtten

[57] ABSTRACT

The present invention relates to 4,4-disubstituted-3,4-dihydro-2(1H)-quinazolinones of formula I:

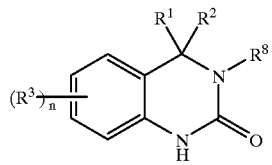

or steroisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent, wherein:

$R^1$ is $C_{1-3}$ alkyl substituted with 1–7 halogen;

$R^2$ is optionally substituted $C_{1-5}$ alkyl, optionally substituted $C_{2-5}$ alkenyl, or optionally substituted $C_{2-5}$ alkynyl;

$R^3$, at each occurrence, is independently selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

$R^5$ and $R^{5a}$ are independently selected from H and $C_{1-3}$ alkyl;

$R^6$ is selected from H, OH, $C_{1-4}$ alkyl, $C_{1-4}$ alkoxy, and $NR^5R^{5a}$;

$R^7$ is selected from $C_{1-3}$ alkyl and $C_{1-3}$ alkoxy;

$R^8$ is selected from H, $C_{3-5}$ cycloalkyl, and $C_{1-3}$ alkyl; and, n is selected from 0, 1, 2, 3, and 4.

54 Claims, No Drawings

4,4-DISUBSTITUTED-3,4-DIHYDRO-2(1H)-QUINAZOLINONES USEFUL AS HIV REVERSE TRANSCRIPTASE INHIBITORS

This application claims the benefit of U.S. provisional application Ser. No. 60/043,115, filed Apr. 9, 1997, and U.S. provisional application Ser. No. 60/071,322, filed Jan. 14, 1998.

FIELD OF THE INVENTION

This invention relates generally to 4,4-disubstituted-3,4-dihydro-2(1H)-quinazolinones which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppresive disease, acquired immunodeficiency syndrome (AIDS). HIV seropositive individuals are initially asymptomatic but typically develop AIDS related comples (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV proteae is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoprotiens on the surface of the viral protective coat. This lack of specificity decreases the immune system's efectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunmodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the procesing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine AZT) 2',3'-dideoxycytidine (ddC), 2',3'-dideoxythymidinene (d4T), 2',3'-dideoxyinosine (ddI), and 2',3'-dideoxy-3'-thiacytidine (3TC) have been shown to be relatively effective in halting HIV replication at the reverse transcriptase (RT) stage.

An active area of research is in the discovery of non-nucleoside HIV reverse transcriptase inhibitors. As an example, it has been found that certain benzoxazinones and quinazolinones are active in the inhibition of HIV reverse trsncriptase, the prevention or treatment of infection by HIV and the treatment of AIDS.

U.S. Pat. No. 5,519,021 describe reverse transcriptase inhibitors which are benzoxazinones of the formula:

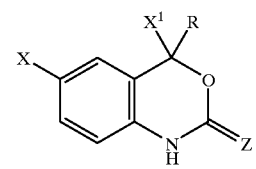

wherein X is a halogen, Z may be O.

EP 0,530,224 and WO 93/04047 describe HIV reverse transcriptase inhibitors which are quinazolinones of the formula A:

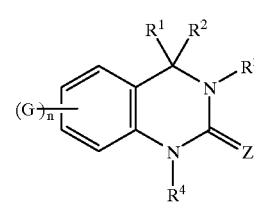

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(-)-6-chloro-4-cyclopropyl-3,4-dihydro-4((2-pyridy) ethynyl)-2(1H)-quinzalinone.

Synthetic procedures for making quinazolinones like those described above are detailed in the following references: Houpis et al, *Tetr. Lett.* 1994, 35(37), 6811–6814; Tucker et al, *J. Med. Chem.* 1994, 37, 2437–2444; and, Huffman et al, *J. Org. Chem.* 1995, 60, 1590–1594.

DE 4,320,347 illustrates quinazolinones of the formula:

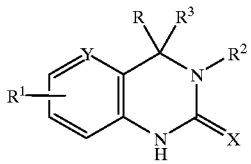

wherein R is a phenyl, carbocycylic ring, or a heterocyclic ring. Compounds of this sort are not considered to be part of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention or a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compostions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide a method of inhibiting HIV present in a body fluid sample which comprises treating the body fluid sample with an effective amount of a compound of the present invention.

It is another object of the presnet inventionto provide a kit or container containing at least one of the compounds of the present invention in an amount effective for use as a standard or reagent in a test or assay for determining the ability of a potential pharmaceutical to inhibit HIV reverse transcriptase, HIV growth, or both.

These and ohter objects, which will becom apparent during the following detailed description, have been achieved by the inventor's discovery that compounds of formula (I):

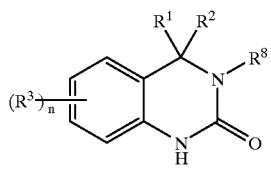

wherein $R^1$, $R^2$, $R^3$, and $R^8$ are defined below, stereoisomeric forms, mixtures of stereoisomeric forms, or pharmaceutically acceptable salt forms thereof, are effectivereverse transcriptase inhibitors.

DETAILED DESCRIPTION OF PREFERRED EMBODIMENTS

[1] Thus, in a first embodiment, the present invention provides a novel compound of formula I:

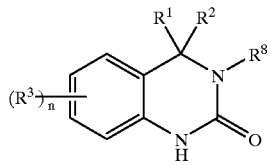

or a stereoisomer or pharmaceutically acceptable salt thereof, wherein:

$R^1$ is $C_{1-3}$ alkyl substituted with 1–7 halogen;

$R^2$ is selected from $C_{1-5}$ alkyl substituted with 1–2 $R^4$, $C_{2-5}$ alkenyl substituted with 1–2 $R^4$, and $C_{2-5}$ alkynyl substituted with 1 $R^4$;

$R^3$, at each occurrence, is independently selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

alternatively, if two $R^3$'s are present and are attached to adjacent carbons, then they may combine to form —$OCH_2O$—;

$R^4$ is selected from $C_{3-5}$ cycloalkyl substituted with 0–2 $R^3$, phenyl substituted with 0–5 $R^3$, and a 5–6 membered heterocyclic system containing 1–3 heteroatoms selected from O, N, and S, substituted with 0–2 $R^3$;

$R^5$ and $R^{5a}$ are independently selected from H and $C_{1-3}$ alkyl;

$R^6$ is selected from H, OH, $C_{1-4}$ alkyl, $C_{1-4}$ alkoxy, and $NR^5R^{5a}$;

$R^7$ is selected from $C_{1-3}$ alkyl and $C_{1-3}$ alkoxy;

$R^8$ is selected from H, $C_{3-5}$ cycloalkyl, and $C_{1-3}$ alkyl; and, n is selected from 0, 1, 2, 3, and 4.

[2] In a preferred embodiment, the present invention provides a novel compound of formula I, wherein:

$R^1$ is $C_{1-3}$ alkyl substituted with 1–7 halogen;

$R^2$ is selected from $C_{1-5}$ alkyl substituted with 1 $R^4$, $C_{2-5}$ alkenyl substituted with 1 $R^4$, and $C_{2-5}$ alkynyl substituted with 1 $R^4$;

$R^3$, at each occurrence, is independently selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

alternatively, if two $R^3$'s are present and are attached to adjacent carbons, then they may combine to form —$OCH_2O$—;

$R^4$ is selected from $C_{3-5}$ cycloalkyl substituted with 0–2 $R^3$, phenyl substituted with 0–2 $R^3$, and a 5–6 membered heterocyclic system containing 1–3 heteroatoms selected from O, N, and S, substituted with 0–1 $R^3$;

$R^5$ and $R^{5a}$ are independently seleted from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$;

$R^8$ is selected from H, cyclopropyl, $CH_3$ and $C_2H_5$; and, n is selected from 0, 1, 2, and 3.

[3] In a more preferred embodiment, the present invention provides a novel compound of formula I, wherein:

$R^1$ is selected from $CF_3$, $C_2F_5$;

$R^2$ is selected from $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, at each occurrence, is independently selected from $C_{1-3}$ alkyl, OH, $C_{1-3}$ alkoxy, F, Cl, Br, I, $NR^5R^{5a}$, $NO_2$, CN, $C(O)R^6$, $NHC(O)R^7$, and $NHC(O)NR^5R^{5a}$;

alternatively, if two $R^3$'s are present and are attached to adjacent carbons, then they may combine to form —$OCH_2O$—;

$R^4$ is selected from $C_{3-5}$ cycloalkyl substituted with 0–2 $R^3$, phenyl substituted with 0–2 $R^3$, and a 5–6 membered heterocyclic system containing 1–3 heteroatoms selected from O, N, and S, substituted with 0–1 $R^3$;

$R^5$ and $R^{5a}$ are independently selected from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$;

$R^8$ is selected from H, $CH_3$ and $C_2H_5$; and, n is selected from 0, 1, and 2.

[4] In an even more preferred embodiment, the present invention provies a novel compound of formula I, wherein:

$R^1$ is $CF_3$;

$R^2$ is selected from $C_{1-3}$ alyl substituted with 1 $R^4$, $C_{2-3}$ alkenyl substituted with 1 $R^4$, and $C_{2-3}$ alkynyl substituted with 1 $R^4$;

$R^3$, at each occurrence, is independently selected from $C_{1-3}$ alkyl, OH, $C_{1-3}$ alkoxy, F, Cl, $NR^5R^{5a}$, $NO_2$, CN, $C(O)R^6$, $NHC(O)R^7$, and $NHC(O)NR^5R^{5a}$;

alternatively, if two $R^3$'s are present and are attached to adjacent carbons, then they may combine to form —$OCH_2O$—;

$R^4$ is selected from cyclopropyl substituted with 0–2 $R^3$, phenyl substituted with 0–2 $R^3$, and a 5–6 membered heterocyclic system containing 1–3 heteroatoms selected from O, N, and S, substituted with 0–1 $R^3$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^5$ and $R^{5a}$ are independently selected from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$;

$R^8$ is selected from H, $CH_3$ and $C_2H_5$; and, n is selected from 0, 1, and 2.

[5] In a further preferred embodiment, wherein the compound is of formula Ia

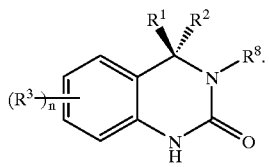

Ia

[5] In a preferred embodiment, wherein the compound is of formula Ib:

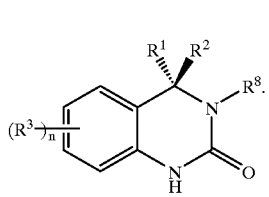

Ib

[7] In a further preferred embodiment, the compound of formula I is selected from:

(+/−)-6-Chloro-4-cyclopropylethynyl-4-trifluoromethyl-3,4-dihydro-2(1H)-quinazolinone;

(+/−)-6-Chloro-4-(2-pyridyl)ethynyl-4-trifluoromethyl-3,4-dihydro-2(1H)-quinazolinone;

(+/−)-6-Chloro-4-phenylethynyl-4-trifluoromethyl-3,4-dihydro-2(1H)-quinazolinone;

(+/−)-4-Cyclopropylethynyl-6-methoxy-4-trifluoromethyl-3,4-dihydro-2(1H)-quinazolinone;

(+/−)-6-Methoxy-4-(2-pyridyl)ethynyl-4-trifluoromethyl-3,4-dihydro-2(1H)-quinazolinone;

(+/−)-6-Methoxy-4-phenylethynyl-4-trifluoromethyl-3,4-dihydro-2(1H)-quinazolinone;

(+/−)-4-Cyclopropylethynyl-5,6-difluoro-4-trifluoromethyl-3,4-dihydro-2(1H)-quinazolinone;

(+/−)-5,6-Difluoro-4-(2-pyridyl)ethynyl-4-trifluoromethyl-3,4-dihydro-2(1H)-quinazolinone;

(+/−)-5,6-Difluoro-4-phenylethynyl-4-trifluoromethyl-3,4-dihydro-2(1H)-quinazolinone;

(+/−)-4-Cyclopropylethynyl-6-fluoro-4-trifluoromethyl-3,4-dihydro-2(1H)-quinazolinone;

(+/−)-6-Fluoro-4-(2-pyridyl)ethynyl-4-trifluoromethyl-3,4-dihydro-2(1H)-quinazolinone;

(+/−)-6-Fluoro-4-phenylethynyl-4-trifluoromethyl-3,4-dihydro-2(1H)-quinazolinone;

(+/−)-6-Fluoro-4-(2'-2-pyridyl)ethyl-4-trifluoromethyl-3,4-dihydro-2(1H)-quinazolinone;

(+/−)-6-Fluoro-4-phenylethyl-4-trifluoromethyl-3,4-dihydro-2(1H)-quinazolinone;

(−)-6-Chloro-4-cyclopropylethynyl-4-trifluoromethyl-3,4-dihydro-2(1H)-quinazolinone (+)-6-Chloro-4-cyclopropylethynyl-4-trifluoromethyl-3,4-dihydro-2(1H)-quinazolinone (+)-4-Cyclopropylethynyl-5,6-difluoro-4-trifluoromethyl-3,4-dihydro-2(1H)-quinazolinone;

(−)-4-Cyclopropylethynyl-5,6-difluoro-4-trifluoromethyl-3,4-dihydro-2(1H)-quinazolinone;

(−)-4-E-Cyclopropylethenyl-5,6-difluoro-4-trifluoromethyl-3,4-dihydro-2(1H)-quinazolinone; and, (−)-6-Chloro-4-E-cyclopropylethenyl-4-trifluoromethyl-3,4-dihydro-2(1H)-quinazolinone;

or a pharmaceutically acceptable salt thereof.

[8] In a second embodiment, the present invention provides a novel compound of formula II:

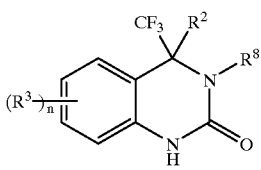

or a stereoisomer or pharmaceutically acceptable salt thereof, wherein:

$R^2$ is $C\equiv C-R^{4a}$;

$R^3$ is selected from $C_{1-4}$ alkenyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

$R^{4a}$ is selected from methyl, ethyl, n-propyl, i-propyl, i-butyl, t-butyl, and i-pentyl;

$R^5$ and $R^{5a}$ are independently selected from H, $CH_{1-3}$ alkyl;

$R^6$ is selected from H, OH, $CH_{1-4}$, $C_{1-4}$ alkoxy, and $NR^5R^{5a}$;

$R^7$ is selected from $CH_{1-3}$ alkyl and $C_{1-3}$ alkoxy;

$R^8$ is selected from H, $CH_{3-5}$ cycloalkyl, and $C_{1-3}$ alkyl; and n is selected from 0, 1, 2, 3, and 4.

[9] In another preferred embodiment, the present invention provides a novel compound of formula II, wherein:

$R^2$ is $C\equiv C-R^{4a}$;

$R^3$ is selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$;

$R^{4a}$ is selected from methyl, ethyl, n-propyl, i-propyl, i-butyl, t-butyl, and i-pentyl;

$R^5$ and $R^{5a}$ are independently selected from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$;

$R^8$ is selected from H, cyclopropyl, $CH_3$ and $C_2H_5$; and, n is selected from 0, 1, and 2.

[10] In a further preferred embodiment, wherein the compound is of formula IIa

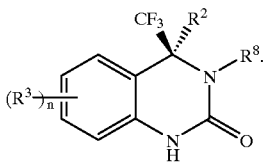

[11] In a further preferred embodiment, wherein the compound is of formula IIb:

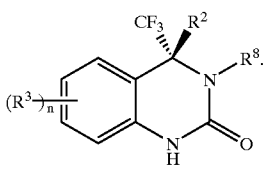

[12] In another more preferred embodiment, the compound of formula II is selected from:
(+/−)-6-Chloro-4-isopropylethynyl-4-trifluoromethyl-3,4-dihydro-2(1H)-quinazolinone;
(+/−)-6-Chloro-4-ethylethynyl-4-trifluoromethyl-3,4-dihydro-2(1H)-quinazolinone;
(+/−)-4-Isopropylethynyl-6-methoxy-4-trifluoromethyl-3,4-dihydro-2(1H)-quinazolinone;
(+/−)-5,6-Difluoro-4-isopropylethynyl-4-trifluoromethyl-3,4-dihydro-2(1H)-quinzolinone;
(+/−)-5,6-Difluoro-4-ethylethynyl-4-trifluoromethyl-3,4-dihydro-2(1H)-quinazolinone;
(+/−)-5,6Difluoro-4-isopentyl-4-trifluoromethyl-3,4-dihydro-2(1H)-quinazolinone;
(+/−)-6-Fluoro-4isopropylethynyl-4-trifluoromethyl-3,4-dihydro-2(1H)-quinazolinone;
(+/−)-6-Fluoro-4-ethlethynyl-4-trifluoromethyl-3,4-dihydro-2(1H)-quinazolinone;
(−)-5,6-Difluoro-4-isopropylethynyl-4-trifluoromethyl-3,4-dihydro-2(1H)-quinazolinone;
(+)-5,6-Difluoro-4-isopropylethynyl-4-trifluoromethyl-3,4dihydro-2(1H)-quinazolinone;
(−)-5,6-Difluoro-4-ethylethynyl-4-trifluoromethyl-3,4dihydro-2(1H)-quinazolinone; and,
(+)-5,6-Difluoro-4-ethylethynyl-4-trifluoromethyl-3,4-dihydro-2(1H)-quinazolinone;
or a pharmaceutically acceptable salt thereof.

In a third embodiment, the present invention provides a novel pharmaceutical composition comprising a pharmaceutically acceptable carrier and a therapeutically effective amount of a compound of formula I or II or pharmaceutically acceptable salt form thereof.

In a fourth embodiment, the present invention provides a novel method for treating HIV infection which comprises administering to a host in need of such treatment a therapeutically effective amount of a compound of formula I or II or pharmaceutically acceptable salt form thereof.

In a fifth embodiment, the present invention provides a novel method of treating HIV infection which comprises administering, in combination, to a host in need thereof a therapeutically effective amount of:

(a) a compound of formula I or II; and, (b) at least one compound selected from the group consisting of HIV reverse transcriptase inhibitors and HIV protease inhibitors.

In another preferred embodiment, the reverse transcriptase inhibitor is selected from AZT, 3TC, ddI, ddC, d4T, delavirdine, TIBO derivatives, BI-RG-587, nevirapine, L-697, 661, LY 73497, Ro 18,898, loviride, trovirdine, MKC-442, and HBY 097, and the protease inhibitor is selected from saquinavir, ritonavir, indinavir, VX-478, nelfinavir, KNI-272, CGP-61755, U-140690, and ABT-378.

In an even more preferred embodiment, the reverse transcriptase inhibitor is selected from AZT and 3TC and the protease inhibitior is selected from saquinavir, ritonavir, nelfinavir, and indinavir.

In a still further preferred embodiment, the reverse transcriptase inhibitor is AZT.

In another still further preferred embodiment, the protease inhibitor is indinavir.

In a sixth embodiment, the present invention provides a pharmaceutical kit useful for the treatment of HIV infection, which comprises a therapeutically effective amount of:

(a) a compound of formula I or II; and, (b) at least one compound selected from the group consisting of HIV reverse transcriptase inhibitors and HIV protease inhibitors, in one or more sterile containers.

In a seventh embodiment, the present invention provides a novel method of inhibiting HIV present in a body fluid sample which comprises treating the body fluid sample with an effective amount of a compound of formula I or II.

In a eighth embodiment, the present invention to provides a novel a kit or container comprising a compound of formula I or II in an amount effective for use as a standard or reagent in a test or assay for determining the ability of a potential pharmaceutical to inhibit HIV reverse transcriptase, HIV growth, or both.

DEFINITIONS

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a sturcure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon—carbon bonds which may occur in any stable point along the chain, such as ethenyl, propenyl and the like. "Alkynyl" is intended to incude hydrocarbon chains of either a straight or branched configuration and one or more triple carbon—carbon bonds which may occur in any stable point along the chain, such as ethynyl, propynyl and the like.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3- to 5-membered monocyclic ring, which may be saturated or partially unsaturated. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic system" is intended to mean a stable 5- to 6-membered monocyclic heterocyclic ring which is saturated partially unsaturated or unsaturated (aromatic), and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compond is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "atomatic heterocyclic system" is intended to mean a stable 5- to 6-membered monocyclic heterocyclic aromatic ring which consists of carbon atoms and from 1 to 3 heteroatoms independently selected from the group consisting of N, O and S. It is preferred that the total number of S and O atoms in the aromatic heterocycle is not more than 1.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadizolyl, 1,2,5-oxadiazolyl, 1,2,4-oxadiazolyl, oxazolidinyl, oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydropuranyl, 6H,1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-trizolyl, and 1,3,4-triazolyl. Preferred heterocyles include, but are not limited to, pyridinyl, furanyl, thienyl, pyrrolyl, pyrazolyl, imidazolyl, and oxazolidinyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), TIBO derivatives, BI-RG-587, nevirapine (Boehring Ingelheim), L-697,661, LY 73497, Ro 18,893 (Roche), loviride (Janssen), trovirdine (Lilly), MKC-442 (Triangle), and HBY 097 (Hoechst).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), U-140690 (Pharmacia and Upjohn), and ABT-378.

Additional examples include the cyclic protease inhibitors disclosed in WO93/07128, WO 94/19329, WO 94/22840, and PCT Application Number US 96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventinal non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the the present invention can be synthesized from the parent compound which contains a basic or acidic moiety by conventional chemical methods. Generally, such salts can be prepared by reacting the free acid or base forms of thses compunds with a stoichiometric amount of the appropriate base or acid in water or in an organic solvent, or in a mixture of the two; generally, nonaqueous media like ether, ethyl acetate, ethanol isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutiaclly acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to formula (I) or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like.

"Stable compound" and "stable structure" are meant to indicate a compound that is sufficiently robust to survive isolation to a useful degree of purity from a reaction mixture, and formulation into an efficacious therapeutic agent. Only stable compounds are contempleted by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituten to keto (i.e., =O) group, then 2 hydrogens on the atom are replaced.

"Therapeutically effective amount" is intended to include an amount of a compound of the present invention or an amount of the combination of compounds claimed effective to inhibit HIV infection to treat the symptoms of HIV infection in a host. The combination of compounds is preferagbly a synergistic combination. Synergy, as described for example by Chou and Talalay, Adv. Enzyme Regul. 22:27–55 (1984), occurs when the effect (in this case, inhibition of HIV replication) of the compounds when adminsitered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of orgainc synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

SCHEME 1

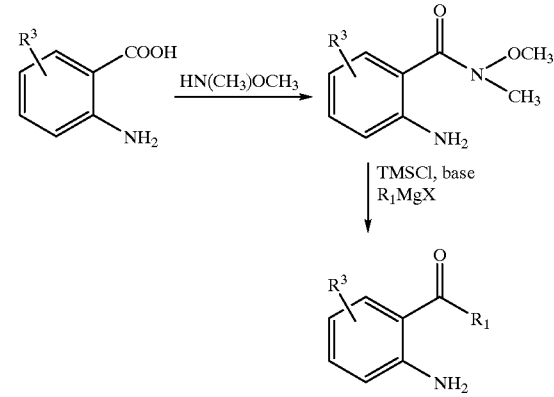

Scheme 1 illustrates a method of preparing keto-anilines from an appropriately subsututed 2-aminobenzoic acid. The acid is converted to its N-methoxy-N-methyl amide derivative which can then be displaced to obtain the $R^1$-substituted ketone. The keto-anilines are useful intermediates for the presently claimed compounds.

SCHEME 2

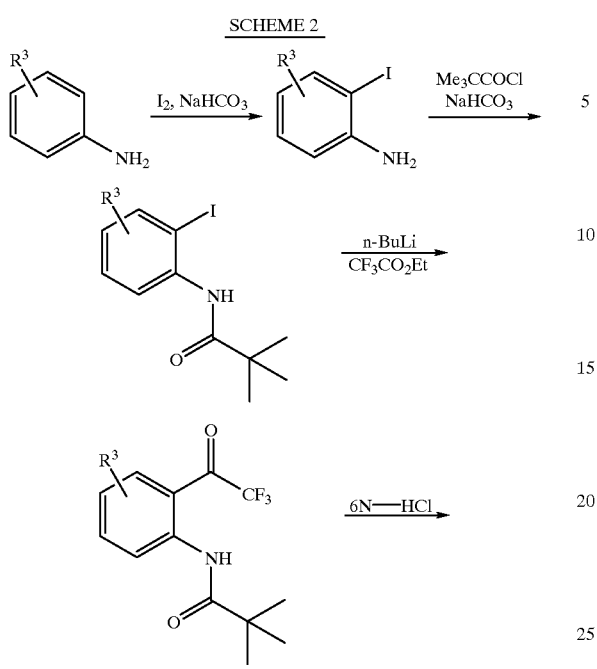

Scheme 2 describes another method of preparing keto-anilines, this time from an appropriately substituted aniline. After iodination and amine protection, a group such as trifluoromethyl can be introduced using a strong base and ethyl trifluoroacetate. Deprotection provides the ketoaniline. Additional means of preparing keto-anilines are known to one of skill in the art, e.g., Houpis et al, *Tetr. Lett.* 1994, 35(37), 6811–6814, the contents of which are hereby incorporated herein by reference.

SCHEME 3

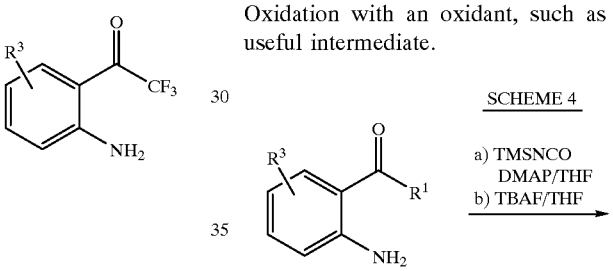

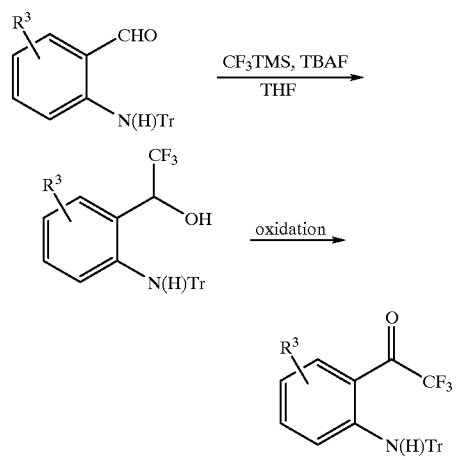

Another method of making 2-trifluoroacetylanilines is shown in Scheme 3. After forming the protected aniline, the amide is then reduced and the trifluoromethyl group added. Oxidation with an oxidant, such as $MnO_2$, provides the useful intermediate.

SCHEME 4

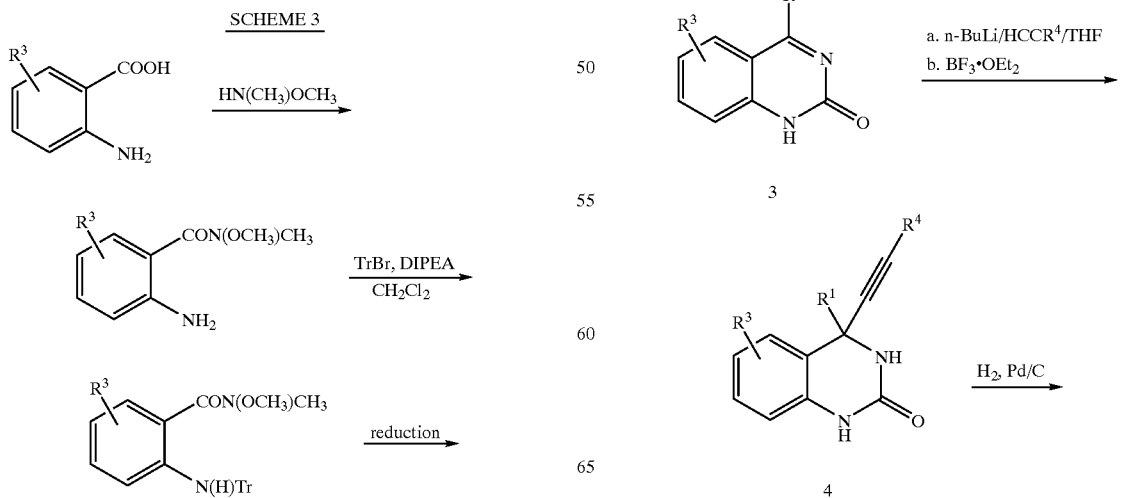

15
-continued

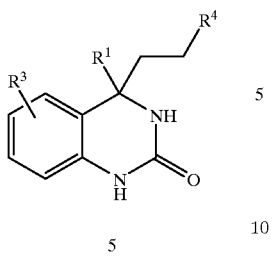
5

Using the general method detailed in Scheme 4, one can prepare compounds of the present invention. Keto-aniline 1, which may be prepared by the methods described in Schemes 1 and 2, is treated with trimethylsilyl isocyanante in dry tetrahydrofuran in the presence of dimethylaminopyridine followed by tetrabutylammonium fluoride to give the hydroxy-urea 2. The hydroxy-urea 2 is then dehydrated with a dehydrating agent such as 4 Å molecular sieves in refluxing toluene or xylenes to give the ketimine 3. A substituted acetylenic $R^2$ group is added by treating the ketimine 3 with a lithium acetylide, which is prepared in a separate vessel by reacting the corresponding substituted acetylene with n-butyllithium in dry tetrahydrofuran, to give the 4,4-disubstituted 3,4-dihydro-2(1H)-quinazolinone 4, a compound of formula I. The acetylenic bond of the compound 4 may be reduced, e.g., by catalytic hydrogation, to give the corresponding alkenyl group (not shown) or the saturated compound 5.

Other $R^2$ groups may also be introduced by directly reacting the imine 3 with a lithiate $R^2Li$ or a Grignard reagent $R^2MgX$ in the presence or absence of Lewis acid catalyst, such as $BF_3$ etherate. See also Huffman et al, *J. Org. Chem.* 1995, 60, 1590–1594, the contents of which are hereby incorporated herein by reference.

In certain instances, one enantimoer of a compound of Formula I or II may display superior activity compared with the other. When required, separation of the racemic material can be achieved by HPLC using a chiral column as exemplified in Examples 27–34 (Scheme 4) or by a resolution using a resolving agent such as camphonic choloride as in Thomas J. Tucker, et al, *J. Med. Chem.* 1994, 37, 2437–2444. A chiral compound of Formula I may also be directly synthesized using a chiral catalyst or a chiral ligand, e.g. Mark A. Huffman, et al, *J. org. Chem.* 1995, 60 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "°C" for degrees Celcius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "EDAC" for 1-(3-dimethylaminopropyl)-3-ethylcarbodiimide hydrochloride, "DIPEA" for diisopropylethylamine, "TBAF" for tetrabutylammonium fluoride, "LAH" for lithium aluminum hydride, and "TEA" for triethylamine.

16
EXAMPLE 1

Preparation of (+/−)-6-Chloro-4-cyclopropylethynyl-4-trifluoromethyl-3,4-dihydro-2 (1H)-quinazolinone ($R^4$=Cyclopropyl)

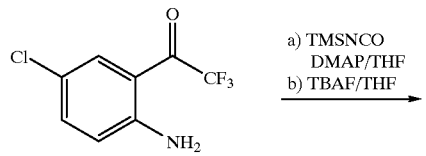

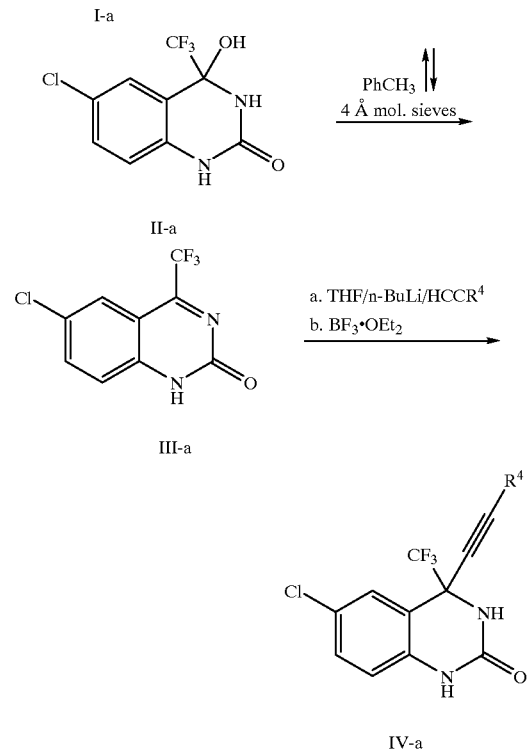

Step 1. Synthesis of II-a from I-a.

To a solution of compound I-a (4.55 g, 20.2 mmol) in anhydrous THF (40 mL) was added dimethylaminopyridine (0.25 g, 2.02 mmol) and trimethylsilyl isocyanate (6.05 g, 7.11 mL, 52.5 mmol). The mixture was stirred at room temperature for approximately 16 hours, then tetrabutylammonium fluoride (21 mL of 1M solution in THF) was added. The thick slurry was siluted with additional THF (20 mL) and stirred at room temperature for 0.5 hours. The THF was removed under reduced pressure, the residue was taken up in EtOAc (100 mL) and washed sequentially with 1N HCl (70 mL), saturated aqueous $NaHCO_3$ (70 mL) and saturated aqueous NaCl (50 mL). The organic phase was dried over $MgSO_4$, filtered and concentrated under reduced pressure to afford a light yellow solid. The yellow color was removed upon trituration with hexanes to afford IIa (5.09 g, 94%) as a white solid: $^1H$ NMR (300 mHz, acetone-$d_6$) δ 9.06 (br s, 1 H), 7.48 (s, 1 H), 7.40 (br s, 1 H), 7.34 (dd, J=8.8, 2.6 Hz, 1 H), 6.97 (d, J=8.8 Hz, 1 H); $^{19}F$ NMR (282 MHz, acetone-$d_6$) δ −86.33, −86.35; IR (KBr Pellet) 1724, 1678, 1398, 1198, 1174 $cm^{-1}$; MS (CI) m/e 266 ($MH^{30}$, 100).

Step 2. Synthesis of III-a from II-a.

A suspension of II-a (5.09 g, 19.1 mmol) in toluene (150 mL) containing 4 Å molecular sieves (approximately 100 mg) was heated at reflux for 16 hours. The resulting clear yellow solution was cooled to room temperature, the precipitated solids were dissolved in acetone and the molecular sieves are removed by vacuum filtration. The filtrate was concentrated under reduced pressure, and triturated with hexanes to afford III-a (4.25 g, 89%) as a yellow solid: $^1$H NMR (300 MHz, acetone-$d_6$) δ 7.86–7.82 (m, 2 H), 7.61 (d, J=8.8 Hz, 1 H); $^{19}$F NMR (282 MHz, acetone-$d_6$) δ –67.88.

Step 3. Synthesis of IV-a from IIIa.

A solution of cyclopropylacetylene (13.0 mL of 30 wt % solution in toluene/THF/hexanes, 59.0 mmol) in anhydrous THF (118 mL) was cooled to –78° C., treated with n-BuLi (32.8 mL of 1.6M solution in hexanes, 52.4 mmol), warmed to 0° C. in an ice bath, and aged for 0.5 h. To a solution of III-a (3.12 g, 12.6 mmol) in anhydrous THF (66 mL) at –78° C. was added the lithium acetylide over approximately 10 minutes. To this was added boron tirfluoride etherate (0.89 g, 0.80 mL, 6.28 mmol), followed by removal of the cooling bath. The reaction was allowed to reach room temperature and stirred at room temperature for 4 hours before quenching with 1M citric acid (100 mL). The mixture was concentrated under reduced pressure to ½ original volume diluted with EtOAc (200 mL), the aqueous phase was removed and the orgainic phase was sequentially washed with saturated aqueous NaHCO$_3$ (100 mL), and saturated aqueous NaCl (100 mL). The organic phase was dried over MgSO$_4$, filtered and concentrated under reduced pressure. The crude material was purified by flash chromatography (3% MeOH/CH$_2$Cl$_2$) to afford a thick yellow oil from which was obtained crystalline IV-a (R$^4$=cyclopropyl) (3.85 g, 97%) as a white solid: mp 86.6–88° C.; $^1$H NMR (300 MHz, acetone-$d_6$) δ 8.95 (br s, 1 H), 7.51 (br s, 1 H), 7.43 (br s, 1 H), 7.40 (dd, J=8.8, 2.4 Hz, 1 H), 7.02 (d, J=8.8 Hz, 1 H), 1.49–1.41 (m, 1 H), 0.93–0.82 (m, 1 H), 0.77–0.74 (m, 1 H); $^{19}$F NMR (282 MHz, acetone-$d_6$) δ –82.96; IR (KBr Pellet) 1696, 1172 cm$^{-1}$; MS (CI) m/e calc'd for C$_{14}$H$_{10}$ClF$_3$N$_2$O: 315.051201, found 315.051626; 315 (MH$^{30}$, 51), 332 (M+NH$_4$+, 100); Analysis calc'd for C$_{14}$H$_{10}$N$_2$ClF$_3$O.0.25 H$_2$O: C, 52.68; H, 3.32; N, 8.78; found: C, 52.61; H, 3.35; N, 8.28.

EXAMPLE 2

Preparation of (+/−)-6-Chloro-4-isopropylethynyl-4-trifluoromethyl-3,4-dihydro-2(1H)-quinazolinone (R$^4$=Isopropyl)

A solution of III-a (50 mg, 0.201 mmol) was treated with the lithium acetylide derived from 3-methyl-1-butyne (62 mg, 93 mL, 0.905 mmol) according to the procedure of Step 3 of Example 1. The resulting crude material was purified by flash chromatography (35% EtOAc/hexanes) to afford 26 mg (41%) of the desired product: $^1$H NMR (300 MHz,) δ9.08 (br s, 1 H), 7.59 (br s, 1 H), 7.53 (br s, 1 H), 7.40 (dd, J=8.4, 2.2 Hz, 1 H), 7.02 (d, J=8.8 Hz, 1 H), 2.81–2.68 (m, 1 H), 1.20 (dd, J=6.6 Hz, 6 H); $^{19}$F NMR (282 MHz, acetone-$d_6$) δ –83.05; MS (CI) m/e calc'd for C$_{14}$H$_{12}$ClF$_3$N$_2$O: 317.066851, found 317.069433; 317 (MH$^+$, 43), 334 (M+NH$_4$$^{30}$, 100).

EXAMPLE 3

Preparation of (+/'-)-6-Chloro-4-(2-pyridyl)ethynyl-4-trifluoromethyl-3,4-dihydro-2(1H)-quinazolinone (R$^4$=2-Pyridyl)

A solution of III-a (110 mg, 0.402 mmol) was treated with the the lithium acetylide derived from 2-thynylpyridine (0.19 g, 1.81 mmol) according to the procedure of Step 3 of Example 1. The resulting crude material was purified by HPLC (2.5% MeOH/CH$_2$Cl$_2$) to afford 85 mg (60%) of the desired product: mp 105° C. dec.; $^1$H NMR (300 MHz, acetone-$d_6$) δ 9.14 (br s, 1 H), 8.64-8.61 (m, 1 H), 7.89-7.84 (m, 2 H), 7.70-7.66 (m, 2 H), 7.48-7.43 (m, 2 H), 7.09 (d, J=8.8 Hz, 1 H); $^{19}$F NMR (282 MHz, acetone-$d_6$) δ –82.48; IR (KBr Pellet) 1704, 1430, 1186 cm$^{-1}$; MS (CI) m/e calc'd for C$_{16}$H$_{10}$ClF$_3$N$_3$O: 352.046450, found 352.046956; 352 (MH$^+$, 100); Analysis calc'd for C$_{16}$H$_9$ClF$_3$N$_3$O.0.125 H$_2$O; C, 54.3; H, 2.56; N, 11.9; found: C, 54.71; H, 3.03; N, 11.3.

EXAMPLE 4

Preparation of (+/−)-6-Chloro-4-ethylethynyl-4-trifluoromethyl-3,4-dihydro-2(1H)-quinazolinone (R$^4$=Ethyl)

A solution of III-a (100 mg, 0.402 mmol) was treated with the the lithium acetylide derived from 1-butyne (1.09 mg, 2.01 mmol) according to the procedure of Step 3 of Example 1. The resulting crude material was purified by HPLC (2.5% MeOH/CH$_2$Cl$_2$) to afford 79 mg (65%) of the desired product: $^1$H NMR (300 MHz, acetone-$d_6$) δ 9.05 (br s, 1 H), 7.54 (br s, 2 H), 7.41-7.39 (m, 1 H), 7.02 (d, J=8.4 Hz, 1 H); 2.36-2.32 (m, 2 H), 2.18-1.13 (m, 3 H); $^{19}$F NMR (282 MHz, acetone-$d_6$) δ –82.99; MS (CI) m/e calc'd for C$_{13}$H$_{10}$Cl$_{F3}$N$_2$O: 303.051201, found 303.051882; 303 (MH$^+$, 55), 320 (M+NH$_4$$^+$, 100).

EXAMPLE 5

Preparation of (+/−)-6-Chloro-4-phenylethynyl-4-trifluoromethyl-3,4-dihydro-2(1H)-quinazolinone (R$^4$=Phenyl)

A solution of III-a (100 mg, 0.402 mmol) was treated with the the lithium acetylide derived from phenylacetylene (185 mg, 1.81 mmol) according to the procedure of Step 3 of Example 1. The resulting crude material was purified by HPLC (2.5% MeOH/CH$_2$Cl$_2$) to afford 54 mg (38%) of the desired product: $^1$H NMR (300 MHz, acetone-$d_6$) δ 9.07 (br s, 1 H), 7.74 (br s, 1 H), 7.67 (br s, 1 H), 7.62-7.58 (m, 2 H), 7.48-7.40 (m, 4 H), 7.08 (d, J=8.4 Hz, 1 H); $^{19}$F NMR (282 MHz, acetone-$d_6$) δ –82.67; IR (KBr Pellet) 1696, 1186 cm$^{-1}$; MS (CI) m/e calc'd for C$_{17}$H$_{11}$ClF$_3$N$_3$O: 351.051201 found 351.051704; 351 (MH$^+$, 51), 368 (M+NH$_4$$^+$, 100); analysis calc'd for C$_{17}$H$_{10}$ClF$_3$N$_2$O.0.25 H$_2$O: C, 57.48; H, 2.98; N, 7.89; found: C, 57.00; H, 3.03; N, 7.48.

EXAMPLE 6

Preparation of (+/−)-4-Cyclopropylethynyl-6-methoxy-4trifluoromethyl-3,4-dihydro-2(1H)-quinazolinone (R$^4$=Cyclopropyl)

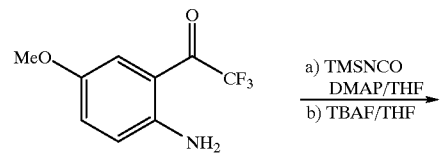

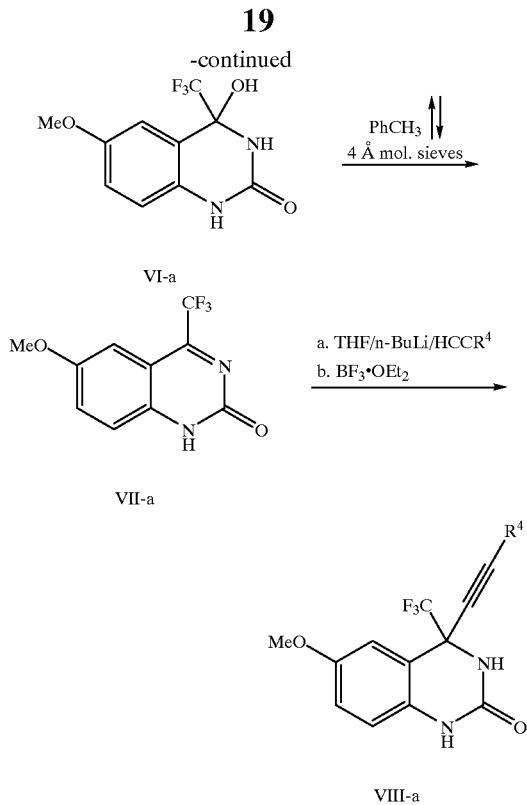

Step 1. Synthesis of VI-a from V-a.

A solution of V-a (0.50 mg, 2.28 mmol) was treated dimethylaminopyridine and trimethylsilyl isocyanate as described in Step 1 of Example 1 to afford 0.58 g (97%) of the desired product: $^1$H NMR (300 MHz, acetone-d$_6$) δ 8.81 (br s, 1 H), 7.74 (br s, 1 H), 7.11 (br s, 1 H), 7.00-6.92 (m, 2 H), 6.83 (s, 1 H), 3.76 (s, 3 H); $^{19}$F NMR (282 MHz, acetone-d$_6$) δ −85.99.

Step 2. Synthesis of VII-a from VI-a.

A solution of VI-a (0.58 g, 2.21 mmol) was heated in toluene at reflux as described in Step 2 of Example 1 to afford 0.50 g (93%) of the desired product: $^1$H NMR (300 MHz, acetone-d$_6$) δ 7.52 (br s, 2 H), 7.27 (s, 1 H), 3.90 (s, 3 H); $^{19}$F NMR (282 MHz, acetone-d$_6$) δ −68.08.

Step 3. Synthesis of VIII-a from VII-a.

A solution of VII-a (100 mg, 0.410 mmol) was treated with the the lithium acetylide derived from cyclopropylacetylene (0.41 mL of 30 wt % solution in toluene/THF/hexanes, 1.85 mmol) according to the procedure of Step 3 of Example 1. The resulting crude material was purified by HPLC (2.5% MeOH/CH$_2$Cl$_2$) to afford 103 mg (81%) of the desired product: $^1$H NMR (300 MHz, acetone-d$_6$) δ 8.77 (br s, 1 H), 7.29 (br s, 1 H), 7.06 (br s, 1 H), 6.99-6.90 (m, 2 H), 3.77 (s, 3 H), 1.46-1.38 (m, 1 H), 0.91-0.85 (m, 2 H), 0.79-0.72 (m, 2 H); $^{19}$F NMR (282 MHz, acetone-d$_6$) δ −82.61; MS (CI) m/e calc'd for C$_{15}$H$_{14}$F$_3$N$_2$O$_2$: 311.100738, found 311.099970; 311 (MH$^+$, 100).

EXAMPLE 7

Preparation of (+/−)-4-Isopropylethynyl-6-methoxy-4-trifluoromethyl-3,4-dihydro-2(1H)-quinazolinone (R$^4$=Isopropyl)

A solution of VII-a (100 mg, 0.410 mmol) was treated with the the lithium acetylide derived from 3-methyl-1-butyne (126 mg, 0.19 mL, 1.85 mmol) according to the procedure of Step 3 of Example 1. The resulting crude material was purified by flash chromatography (2.5% MeOH/CH$_2$Cl$_2$) to afford 30 mg (24%) of the desired product: mp 228–229° C.; $^1$H NMR (300 MHz, acetone-d$_6$) δ 8.72 (br s, 1 H), 7.27 (br s, 1 H), 7.10 (br s, 1 H), 7.00-6.91 (m, 2 H), 3.77 (s, 3 H), 2.73-2.67 (m, 1 H), 1.20 (dd, J=7.0, 1.5 Hz, 6 H); $^{19}$F NMR (282 MHz, acetone-d$_6$) δ −82.71; IR (KBr Pellet) 1696, 1428, 1190, 1176 cm$^{-1}$; MS (CI) m/e calc'd for C$_{15}$H$_{16}$F$_3$N$_3$O$_2$: 313.116388, found 313.115871; 313 (MH$^+$, 100), 330 (M+NH$_4^+$, 15); Analysis calc'd for C$_{15}$H$_{15}$F$_3$N$_2$O$_2$: C, 57.69; H, 4.84; N, 8.97; found: C, 57.74; H, 5.01; N, 8.57.

EXAMPLE 8

Preparation of (+/−)-6-Methoxy-4-(2-pyridyl)ethynyl-4-trifluoromethyl-3,4-dihydro-2(1H)-quinazolinone (R$^4$=2-Pyridyl)

A solution of VII-a (100 mg, 0.410 mmol) was treated with the the lithium acetylide derived from 2-ethynylpyridine (0.19 g, 1.85 mmol) according to the procedure of Step 3 of Example 1. The resulting crude material was purified by flash chromatography (2.5% MeOH/CH$_2$Cl$_2$) to afford 56 mg (39%) of the desired product: $^1$H NMR (300 MHz, acetone-d$_6$) δ 8.81 (br s, 1 H), 8.61 (d, J=4.8 Hz, 1 H); 7.88-7.82 (m, 1 H), 7.66 (d, J=7.7 Hz, 1 H), 7.61 (br s, 1 H), 7.46-7.42 (m, 1 H), 7.23 (br s, 1 H), 7.06-6.97 (m, 2 H), 3.79 (s, 3 H); $^{19}$F NMR (282 MHz, acetone-d$_6$) δ −82.13; IR (KBr Pellet) 1698, 1518, 1464, 1430, 1244, 1208, 1184 cm$^{-1}$; MS (CI) m/e calc'd for C$_{17}$H$_{13}$F$_3$N$_3$O$_2$: 348.095987, found 448.095629; 348 (MH$^+$, 100); Analysis calc'd for C$_{17}$H$_{12}$F$_3$N$_3$O$_2$.0.25 C$_3$H$_6$O: C, 58.92; H, 3.76; N, 11.61; found: C, 59.38; H, 4.04; N, 11.35.

EXAMPLE 9

Preparation of (+/−)-6-Methoxy-4-phenylethynyl-4-trifluoromethyl-3,4-dihydro-2(1H)-quinazolinone (R$^4$=Phenyl)

A solution of VII-a (100 mg, 0.410 mmol) was treated with the the lithium acetylide derived from phenylacetylene (0.19 g, 1.85 mmol) according to the procedure of Step 3 of Example 1. The resulting crude material was purified by flash chromatography (2.5% MeOH/CH$_2$Cl$_2$) to afford 34 mg (24%) of the desired product: mp 206.2-207.7° C.; $^1$H NMR (300 MHz, acetone-d$_6$) δ 8.85 (br s, 1 H), 7.60-7.57 (m, 3 H), 7.49-7.39 (m, 3 H), 7.21 (br s, 1 H), 7.05-6.96 (m, 2 H), 3.79 (s, 3 H); $^{19}$F NMR (282 MHz, acetone-d$_6$) δ −82.32; IR (KBr Pellet) 1696, 1516, 1430, 1236, 1204, 1184, 1128 cm$^{-1}$; MS (CI) m/e calc'd for C$_{18}$H$_{14}$F$_3$N$_2$O$_2$: 347.100738, found 347.101482; 347 (MH$^{30}$, 100), 364 (M+NH$_4^+$, 48); Analysis calc'd for C$_{18}$H$_{13}$F$_3$N$_2$O$_2$: C, 62.43; H, 3.78; N, 8.10 found: C, 62.35; H, 3.58; N, 7.83.

EXAMPLE 10

Preparation of (+/−)-4-Cyclopropylethynyl-5,6-difluoro-4-trifluoromethyl-3,4-dihydro-2(1H)-quinaolinone (R⁴=Cyclopropyl)

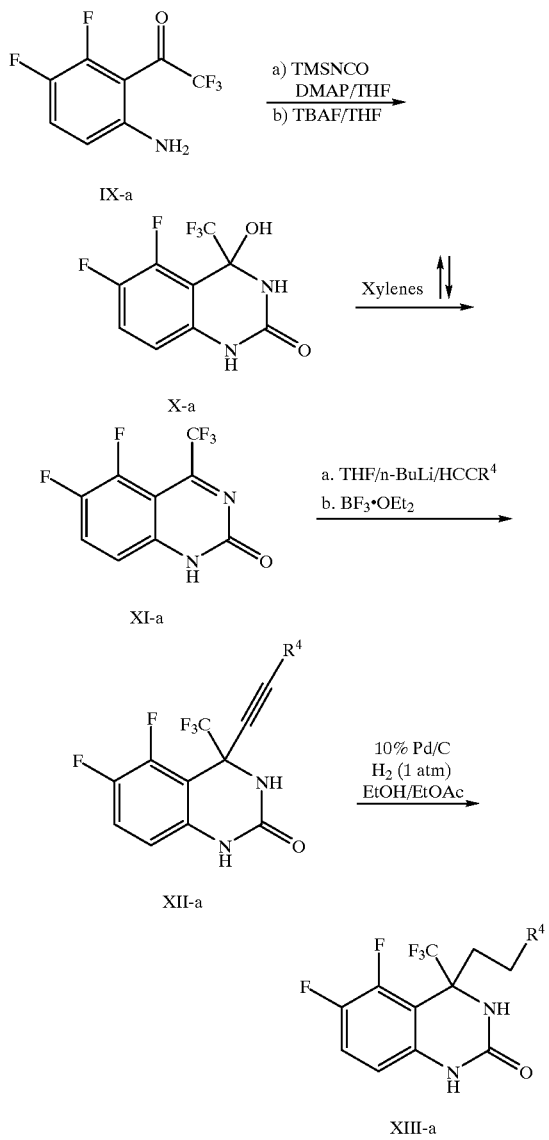

Step 1. Synthesis of X-a from IX-a.

A solution of IX-a (6.46 g, 28.7 mmol) was treated with dimethylaminopyridine and trimethylsilyl isocyanate as described in Step 1 of Example 1 to afford 6.74 g (88%) of the desired product: $^1$H NMR (300 MHz, acetone-$d_6$) δ 9.13 (br s, 1 H), 7.45-7.32 (m, 2 H), 7.18 (br s, 1 H), 6.85-6.80 (m, 1 H); $^{19}$F NMR (282 MHz, acetone-$d_6$) δ−86.6 (d, 17.2, 3), −137.52-137.68 (m, 1), −148.47-148.59 (m, 1).

Step 2. Synthesis of XI-a from X-a.

A solution of X-a (6.74 g, 25.1 mmol) was heated in xylenes at reflux descibed in Step 2 of Example 1 substituting xylenes for toluene, to afford 6.3 g (100%) of the desired product: $^1$H NMR (300 MHz, acetone-$d_6$) δ 7.92-7.83 (m, 1 H), 7.46-7.44 (m, 1 H); $^{19}$F NMR (282 MHz, acetone-$d_6$) δ−70.7 (d, 38.7, 3), −136.72 (s, 1), −146.47-146.57 (m, 1).

Step 3. Synthesis of XII-a from XI-a.

A solution of XI-a (6.28 g, 25.1 mmol) was treated with the the lithium acetylide derived from cyclopropylacetylene (24.9 mL of 30 wt % solution in toluene/THF/hexanes, 0.113 mol) according to the procedure of Step 3 of Example 1. The resulting crude yellow oil was dissolved in acetone and concentrated under reduced pressure to deliver a yellow solid. Crystallization from acetone afforded 5.98 g (75%) of the desired material: mp 86.5-88.5° C.; $^1$H NMR (300 MHz, acetone-$d_6$) δ 9.01 (br s, 1 H), 7.46 (br s, 1 H), 7.44-7.35 (m, 1 H), 6.86-6.81 (m, 1 H), 1.41-1.37 (m, 1 H), 0.90-0.83 (m, 1 H), 0.74-0.69 (m, 1 H), $^{19}$F NMR (282 MHz, acetone-$d_6$) δ −83.3; (d, J=12.9, 1), −136.04-136.23 (m, 1), −148.14-148.26 (m, 1); IR (KBr Pellet) 1706, 1516, 1442, 1246, 1214, 1196 cm$^{-1}$; MS (CI) m/e calc'd for $C_{14}H_{10}F_5N_2O$: 317.071329, found 317.070836; 317 (MH⁺, 100), 334 (M+NH₄⁺, 62); Analysis calc'd for $C_{14}H_9F_5N_2O$: C, 53.17; H, 2.88; N, 8.87; found: C, 53.30; H, 3.16; N, 8.53.

EXAMPLE 11

Preparation of (+/−)-5,6-Difluoro-4-isopropylethynyl-4-trifluoromethyl-3,4-dihydro-2(1H)-quinazolinone (R⁴=Isopropyl)

A solution of XI-a (7.24 g, 28.9 mmol) was treated with the the lithium acetylide derived from 3-methyl-1-butyne (8.87 g, 13.3 mL, 0.130 mol) according to the procedure of Step 3 of Example 1. The resulting crude material was purified by flash chromatography (2.5% MeOH/CH₂Cl₂) to afford a yellow oil. Crystallization from acetone afforded 6.77 g (74%) of the desired product: mp 79–80° C.; $^1$H NMR (300 MHz, acetone-$d_6$) δ 9.02 (br s, 1 H), 7.50 (br s, 1 H), 7.44-7.35 (m, 1 H), 6.87-6.82 (m, 1 H), 269-2.65 (m, 1 H), 1.17 (d, J=7.0 Hz, 6 H); $^{19}$F NMR (282 MHz, acetone-$d_6$) δ −83.4 (d, J=12.9, 1), −135.79-135.94 (m, 1), −148.14-148.26 (m, 1); MS (CI) m/e calc'd for $C_{14}H_{12}F_5N_2O$: 319.086979, found 319.087376; 319 (MH⁺, 100), 336 (M+NH₄⁺, 76).

EXAMPLE 12

Preparation of (+/−)-5,6-Difluoro-4-(2-pyridyl)ethynyl-4-trifluoromethyl-3,4-dihydro-2(1H)-quinazolinone (R⁴=2-Pyridyl)

A solution of XI-a (100 mg, 0.400 mmol) was treated with the the lithium acetylide derived from 2-ethynylpyridine (0.19 g, 1.80 mmol) according to the procedure of Step 3 of Example 1. The resulting crude material was purified by flash chromatography (4% MeOH/CH₂Cl₂) to afford 83 mg (59%) of the desired product: mp 219–220° C.; $^1$H NMR (300 MHz, acetone-$d_6$) δ 9.15 (br s, 1 H), 8.61 (d, J=4.4 Hz, 1 H), 7.88-7.82 (m, 2 H), 7.63 (dd, J=7.0, 1.1 Hz, 1 H); 7.47-7.42 (m, 2 H), 6.94-6.88 (m, 1 H); $^{19}$F NMR (282 MHz, acetone-$d_6$) δ −82.8 (d, J=12.9, 3), −135.78-135.93 (m, 1), −147.86-147.98 (m, 1); IR (KBr Pellet) 1712, 1470, 1450, 1430, 1416, 1264, 1238, 1226, 1198, 1186 cm$^{-1}$; MS (CI) m/e calc'd for $C_{16}H_9F_5N_3O$: 354.066578, found 354.067821; 354 (MH⁺, 100).

EXAMPLE 13

Preparation of (+/−)-5,6-Difluoro-4-ethylethynyl-4-trifluoromethyl-3,4-dihydro-2(1H)-quinazolinone (R⁴=2-Ethyl)

A solution of XI-a (100 mg, 0.400 mmol) was treated with the the lithium acetylide derived from 1-butyne (97 mg, 1.80 mmol) according to the procedure of Step 3 of Example 1. The resulting crude material was purified by HPLC (2.5% MeOH/CH$_2$Cl$_2$) to afford 69 mg (57%) of the desired product: mp 191–194° C; $^1$H NMR (300 MHz, acetone-d$_6$) δ 9.03 (br s, 1 H), 7.50 (br s, 1 H), 7.45-7.35 (m, 1 H), 6.87-6.82 (m, 1 H), 2.34-2.27 (m, 2 H), 1.20-1.15 (m, 3 H) $^{19}$F NMR (282 MHz, acetone-d$_6$) δ −83.3 (d, J=12.9, 3), −135.79-135.98 (m, 1), −148.16-148.29 (m, 1); IR (KBr Pellet) 1704, 1686, 1618, 1444, 1244, 1210, 1192, 1172 cm$^{-1}$; MS (CI) m/e calc'd for C$_{13}$H$_{10}$F$_5$N$_2$O: 305.071329, found 305.071146; 305 (MH$^+$, 100); Analysis calc'd for C$_{13}$H$_9$F$_5$N$_2$O: C, 51.33; H, 2.98; N, 9.22; found: C, 51.00; H, 2.79; N, 8.99.

EXAMPLE 14

Preparation of (+/−)-5,6-Difluoro-4-phenylethynyl-4-trifluoromethyl-3,4-dihydro-2(1H)-quinazolinone (R$^4$=Phenyl)

A solution of XI-a (100 mg, 0.400 mmol) was treated with the the lithium acetylide derived from phenylacetylene (0.18 g, 0.20 mL, 1.80 mmol) according to the procedure of Step 3 of Example 1. The resulting crude material was purified by HPLC (2.5% MeOH/CH$_2$Cl$_2$) to afford 92 mg (65%) of the desired product: $^1$H NMR (300 MHz, acetone-d$_6$) δ 9.14 (br s, 1H), 7.80 (br s, 1H), 7.57–7.54 (m, 2H), 7.49–7.40 (m, 4H), 6.92–6.87 (m, 1H); $^{19}$F NMR (282 MHz, acetone-d$_6$) δ −83.0 (d, J=12.9, 3), −136.08–136.27 (m, 1), −147.87–148.00 (m, 1); MS (CI) m/e calc'd for C$_{17}$H$_{10}$F$_5$N$_2$O: 353.071329, found 353.01716; 353 (MH$^+$, 42), 370 (M+NH$_4^+$, 100).

EXAMPLE 15

Preparation of (+/−)-5,6-Difluoro-4-isopentyl-4-trifluoromethyl-3,4-dihydro-2(1H)-quinazolinone (R$^4$=Isopropyl)

Synthesis of XIII-a from XII-a.

A solution of XIII-a (R$^4$=isopropyl) (26 mg, 82 mmol) in ethanol (1 mL) and EtOAc (0.5 mL) was treated with 10% Pd on carbon (35 mg) under H$_2$ (1 atm) for 16 hours. The catalyst was removed by vacuum filtration through Celite and the filter cake was washed with EtOAc. The combined filtrates were concentrated under reduced pressure to afford 26 mg (100%) of the desired material. No further purification was necessary: $^1$H NMR (300 MHz, acetone-d$_6$) δ 8.88 (br s, 1H), 7.41–7.31 (m, 1H), 6.89–6.81 (m, 2H), 2.55–2.50 (m, 1H), 1.64–1.45 (m, 2H), 1.06–1.02 (m, 1H), 0.89 (dd, J=6.6, 2.2 Hz, 6H); $^{19}$F NMR (282 MHz, acetone-d$_6$) δ −83.22 (d, J=12.1, 3), −138.97–139.13 (m, 1), −148.46–148.58 (m, 1); IR (KBr Pellet) 1700, 1678, 1518, 1438, 1252, 1188, 1172 cm$^{-1}$; MS (CI) m/e calc'd for C$_{14}$H$_{16}$F$_5$N$_2$O: 323.118280, found 323.116703; 323 (MH$^+$, 100), 340 (M+NH$_4^+$, 57).

EXAMPLE 16

Preparation of (+/−)-4-Butyl-5,6-difluoro-4-trifluoromethyl-3,4-dihydro-2(1H)-quinazolinone (R$^4$=Ethyl)

A solution of XIII-a (R$^4$=ethyl) (20 mg, 66 mmol) in ethanol (1 mL) and EtOAc (0.5 mL) was treated with 10% Pd on carbon under H$_2$ according to the procedure of Example 15. Purification by HPLC (2.5% MeOH/CH$_2$Cl$_2$) afforded 12 mg (56%) of the desired product: $^1$H NMR (300 MHz, acetone-d$_6$) δ 8.89 (br s, 1H), 7.41–7.32 (m, 1H), 6.86–6.81 (m, 2H), 2.57–2.47 (m, 1H), 1.56–1.15 (m, 5H), 0.88 (t, J=7.3 Hz, 3H); $^{19}$F NMR (282 MHz, acetone-d$_6$) δ −83.19–83.24 (m, 1), −139.14 (s, 1), −148.49–148.62 (m, 1); MS (CI) m/e calc'd for C$_{13}$H$_{14}$F$_5$N$_2$O: 309.102629, found 309.103555; 309 (MH$^+$, 100), 326 (M+NH$_4^+$, 62).

EXAMPLE 17

Preparation of (+/−)-4-Cyclopropylethynyl-6-fluoro-4-trifluoromethyl-3,4-dihydro-2(1H)-quinazolinone (R$^4$=Cyclopropyl)

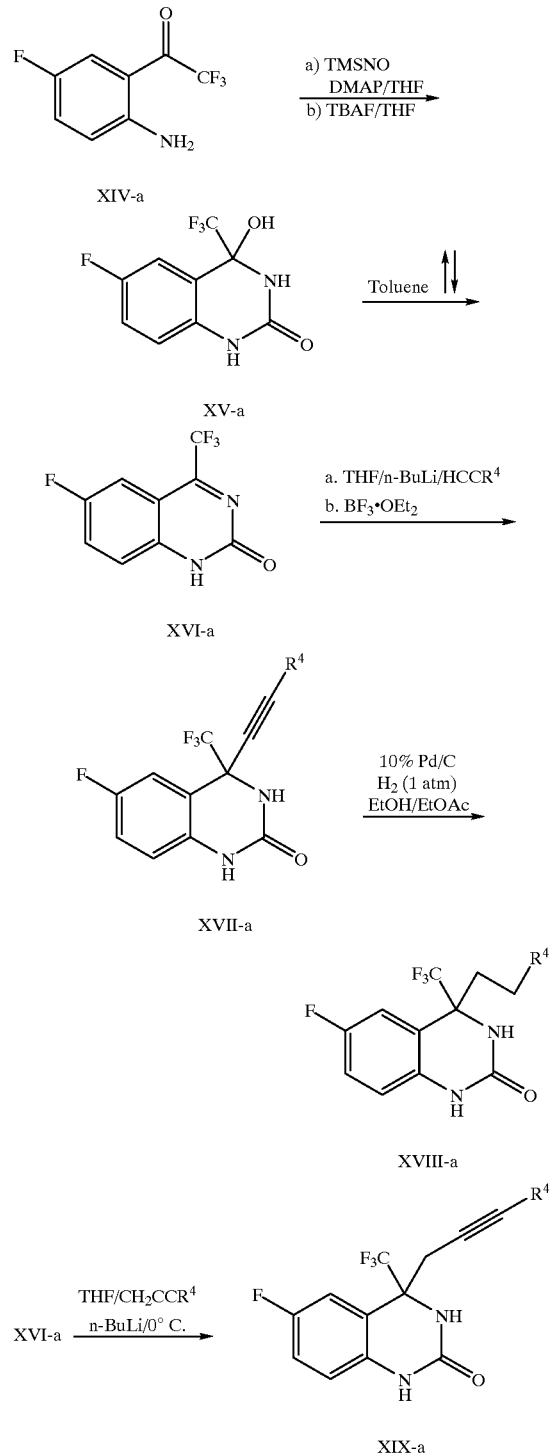

Step 1. Synthesis of XV-a from XIV-a.

A solution of XIII-a (3.07 g, 14.8 mmol) was treated with dimethylaminopyridine and trimethylsilyl isocyanate as described in Step 1 of Example 1 to afford 2.81 g (76%) of the desired product.

Step 2. Synthesis of XVI-a from XV-a.

A solution of XV-a (6.74 g, 2.51 mmol) was heated in toluene at reflux as described in Step 2 of Example 1 to afford 0.73 g (94%) of the desired product.

Step 3. Synthesis of XVII-a from XVI-a.

A solution of XVI-a (100 mg, 0.431 mmol) was treated with the the lithium acetylide derived from cyclopropylacetylene (1.43 mL of 30 wt % solution in toluene/THF/hexanes, 1.94 mmol) according to the procedure of Step 3 of Example 1. The resulting crude material was purified by HPLC (2.5% MeOH/CH$_2$Cl$_2$) to afford 44 mg (34%) of the desired product: mp 155° C.; $^1$H NMR (300 MHz, acetone-d$_6$) δ 8.86 (br s, 1H), 7.36 (br s, 1H), 7.30–7.27 (m, 1H), 7.22–7.15 (m, 1H), 7.04–6.99 (m, 1H), 1.47–1.42 (m, 1H), 0.90–0.87 (m, 2H), 0.76–0.75 (m, 2H); $^{19}$F NMR (282 MHz, acetone-d$_6$) δ −82.86, −123.36–123.44; MS (CI) m/e calc'd for C$_{14}$H$_{11}$F$_4$N$_2$O: 299.080751, found 299.079976; 299 (MH$^+$, 100).

EXAMPLE 18

Preparation of (+/−)-6-Fluoro-4-isopropylethynyl-4-trifluoromethyl-3,4-dihydro-2(1H)-quinazolinone (R$^4$=Isopropyl)

A solution of XVI-a (100 mg, 0.431 mmol) was treated with the the lithium acetylide derived from 3-methyl-1-butyne (0.13 g, 0.20 mL, 1.94 mmol) according to the procedure of Step 3 of Example 1. The resulting crude material was purified by HPLC (2.5% MeOH/CH$_2$Cl$_2$) to afford 24 mg (18%) of the desired product: mp 158° C.; $^1$H NMR (300 MHz, acetone-d$_6$) δ 9.07 (br s, 1H), 7.60 (br s, 1H), 7.32–7.30 (m, 1H), 7.24–7.16 (m, 1H), 7.05–6.99 (m, 1H), 2.77–2.67 (m, 1H), 1.20 (dd, J=7.0, 2.6 Hz, 6H); $^{19}$F NMR (282 MHz, acetone-d$_6$) δ −82.95, −123.41–123.49; MS (301) m/e calc'd for C$_{14}$H$_{13}$F$_4$N$_2$O: 301.096401, found 301.096235; 301 (MH$^+$, 100).

EXAMPLE 19

Preparation of (+/−)-6-Fluoro-4-(2-pyridyl)ethynyl-4-trifluoromethyl-3,4-dihydro-2(1H)-quinazolinone (R$^4$=2-Pyridyl)

A solution of XVI-a (100 mg, 0.431 mmol) was treated with the the lithium acetylide derived from 2-ethynylpyridine (0.20 g, 1.94 mmol) according to the procedure of Step 3 of Example 1. The resulting crude material was purified by HPLC (2.5% MeOH/CH$_2$Cl$_2$) to afford 65 mg (45%) of the desired product: mp 155° C.; $^1$H NMR (300 MHz, acetone-d$_6$) δ 9.02 (br s, 1H), 8.60 (d, J=4.0 Hz, 1H), 7.87–7.78 (m, 2H), 7.66 (d, J=7.7 Hz, 1H), 7.45–7.41 (m, 2H), 7.26–7.20 (m, 1H), 7.09–7.05 (m, 1H); $^{19}$F NMR (282 MHz, acetone-d$_6$) δ −82.36, −122.94–123.02; MS (CI) m/e calc'd for C$_{16}$H$_{10}$F$_4$N$_3$O: 336.076000, found 336.074156; 336 (MH$^+$, 25).

EXAMPLE 20

Preparation of (+/−)-6-Fluoro-4-ethylethynyl-4-trifluoromethyl-3,4-dihydro-2(1H)-quinazolinone (R$^4$=Ethyl)

A solution of XVI-a (100 mg, 0.431 mmol) was treated with the the lithium acetylide derived from 1-butyne (0.10 g, 1.94 mmol) according to the procedure of Step 3 of Example 1. The resulting crude material was purified by HPLC (2.5% MeOH/CH$_2$Cl$_2$) to afford 40 mg (33%) of the desired product: mp 190° C.; $^1$H NMR (300 MHz, acetone-d$_6$) δ 8.86 (br s, 1H), 7.38 (br s, 1H), 7.34–7.31 (m, 1H), 7.22–7.16 (m, 1H), 7.05–7.00 (m, 1H), 2.04–2.01 (m, 2H), 1.19–1.14 (m, 3H); $^{19}$F NMR (282 MHz, acetone-d$_6$) δ −75.392, −123.42–123.50; MS (CI) m/e calc'd for C$_{13}$H$_{11}$F$_4$N$_2$O: 287.080751, found 287.080740; 287 (MH$^+$, 100).

EXAMPLE 21

Preparation of (+/−)-6-Fluoro-4-phenylethynyl-4-trifluoromethyl-3,4-dihydro-2(1H)-quinazolinone (R$^4$=Phenyl)

A solution of XVI-a (100 mg, 0.431 mmol) was treated with the the lithium acetylide derived from phenylacetylene (0.20 g, 0.21 mL, 1.94 mmol) according to the procedure of Step 3 of Example 1. The resulting crude material was purified by HPLC (2.5% MeOH/CH$_2$Cl$_2$) to afford 41 mg (28%) of the desired product: mp 107° C.; $^1$H NMR (300 MHz, acetone-d$_6$) δ 9.00 (br s, 1H), 7.69 (br s, 1H), 7.63–7.59 (m, 2H), 7.50–7.40 (m, 4H), 7.27–7.20 (m, 1H), 7.10–7.05 (m, 1H); $^{19}$F NMR (282 MHz, acetone-d$_6$) δ −82.56, −122.99–123.07; MS (CI) m/e calc'd for C$_{17}$H$_{11}$F$_3$N$_2$O: 335.080751, found 335.082057; 335 (MH$^+$, 74), 352 (M+NH$_3^+$, 100).

EXAMPLE 22

Preparation of (+/−)-6-Fluoro-4-isopentyl-4-trifluoromethyl-3,4-dihydro-2(1H)-quinazolinone (R$^4$=Isopropyl)

Synthesis of XVIII-a from XVII-a.

A solution of XVII-a (R$^4$=isopropyl) (26 mg, 87 mmol) in ethanol (1 mL) and EtOAc (0.5 mL) was treated with 10% Pd on carbon under H$_2$ according to the procedure of Example 15 to afford 15 mg (58%) of the desired product. No further purification was necessary: mp 179° C.; $^1$H NMR (300 MHz, acetone-d$_6$) δ 7.02–6.97 (m, 2H), 6.80–6.76 (m, 1H), 2.18–2.09 (m, 2H), 1.92–1.82 (m, 2H, 1.52–1.45 (m, 1H), 0.88–0.79 (m, 6H); $^{19}$F NMR (282 MHz, acetone-d$_6$) δ −82.60, −123.72–123.84; MS (CI) m/e calc'd for C$_{14}$H$_{17}$F$_4$N$_2$O: 305.127707, found 305.126790; 305 (MH$^+$, 100).

EXAMPLE 23

Preparation of (+/−)-6-Fluoro-4-(2'-2-pyridyl)ethyl-4-trifluoromethyl-3,4-dihydro-2(1H)-quinazolinone (R$^4$=2-Pyridyl)

A solution of XVII-a (R$^4$=2-pyridyl) (33 mg, 99 mmol) in ethanol (1 mL) and EtOAc (0.5 mL ) was treated with 10% Pd on carbon under H$_2$ according to the procedure of Example 15 to afford 10 mg (30%) of the desired product. No further purification was necessary: mp 88° C.; $^1$H NMR (300 MHz, acetone-d$_6$) δ 8.35 (d, J=4.4 Hz, 1H), 7.63 (dt, J=7.7, 1.5 Hz, 1H), 7.20–7.13 (m, 3H), 7.04–6.98 (m, 1H), 6.83–6.79 (m, 1H), 2.84–2.78 (m, 1H), 2.68–2.48 (m, 2H), 2.27–2.06 (m, 1H); $^{19}$F NMR (282 MHz, acetone-d$_6$) δ −82.58, −123.26–123.34; MS (CI) m/e calc'd for C$_{16}$H$_{14}$F$_4$N$_3$O: 340.107300, found 340.107719; 340 (MH$^+$, 100).

EXAMPLE 24

Preparation of (+/−)-4-Butyl-6-fluoro-4-trifluoromethyl-3,4-dihydro-2(1H)-quinazolinone (R⁴=Ethyl)

A solution of XVII-a (R⁴=ethyl) (24 mg, 84 mmol) in ethanol (1 mL) and EtOAc (0.5 mL) was treated with 10% Pd on carbon under $H_2$ according to the procedure of Example 15 to afford 24 mg (100%) of the desired product. No further purification was necessary: mp 198° C.; ¹H NMR (300 MHz, acetone-$d_6$) δ 7.03–6.97 (m, 2H), 6.80–6.76 (m, 1H), 2.18–2.11 (m, 1H), 1.90–1.81 (m, 1H), 1.30–1.19 (m, 3H), 0.97–0.80 (m, 4H); ¹⁹F NMR (282 MHz, acetone-$d_6$) δ −82.692, −123.78–123.86; MS (CI) m/e calc'd for $C_{13}H_{15}F_4N_2O$: 291.112051, found 291.112227; 291 (MH⁺, 100).

EXAMPLE 25

Preparation of (+/−)-6-Fluoro-4-phenylethyl-4-trifluoromethyl-3,4-dihydro-2(1H)-quinazolinone (R⁴=Phenyl)

A solution of XVII-a (R⁴=phenyl) (30 mg, 90 mmol) in ethanol (1 mL) and EtOAc (0.5 mL) was treated with 10% Pd on carbon under $H_2$ according to the procedure of Example 15 to afford 20 mg (67%) of the desired product. No further purification was necessary: mp 98° C.; ¹H NMR (300 MHz, acetone-$d_6$) δ 7.18–6.99 (m, 7H), 6.84–6.79 (m, 1H), 2.68–2.60 (m, 1H), 2.48–2.12 (m, 3H); ¹⁹F NMR (282 MHz, acetone-$d_6$) δ −82.67, −123.24–123.32; MS (CI) m/e calc'd for $C_{17}H_{14}F_3N_2O$: 339.112051, found 339.110781; 339 (MH⁺, 100).

EXAMPLE 26

Preparation of (+/−)-6-Fluoro-4-methylpropargyl-4-trifluoromethyl-3,4-dihydro-2(1H)-quinazolinone (R⁴=Methyl)

Synthesis of XIX-a from XVI-a.

A solution of 2-butyne (94 mg, 1.75 mmol) in anhydrous THF (3.5 mL) was cooled to 0° C., treated with n-BuLi (0.97 mL of 1.6 M solution in hexanes, 1.55 mmol), and aged for 0.5 h. To a solution of XVI-a (90 mg, 0.388 mmol) in anhydrous THF (1.9 mL) at −78° C. was added the lithium anion over 5 minutes, followed by boron trifluoride etherate (25 mL, 0.194 mmol). The cooling bath was removed and the mixture was allowed to warm to room temperature. After 16 h at room temperature, quench by addition of 1 M citric acid (10 mL), dilute with EtOAc (50 mL), separate phases and wash the organic phase sequentially with saturated aqueous $NaHCO_3$ (20 mL) and saturated aqueous NaCl (20 mL). The resulting material was purified by HPLC (2.5% MeOH/$CH_2Cl_2$) to afford 10 mg (9%) of the desired product: mp 181° C.; ¹H NMR (300 MHz, acetone-$d_6$) δ 8.91 (br s, 1H), 7.27 (d, 8.4H), 7.18–7.08 (m, 1H), 7.02–6.97 (m, 2H), 3.29 (dd, J=16.8, 2.6 Hz, 1H), 3.00 (dd, J=16.8, 2.2 Hz, 1H), 1.61–1.59 (m, 3H); ¹⁹F NMR (282 MHz, acetone-$d_6$) δ −81.86, —123.69–123.70; MS (CI) m/e calc'd for $C_{13}H_{11}F_4N_2O$: 287.080751, found 287.080340; 287 (MH⁺, 75), 304 (M+$NH_4^+$, 100).

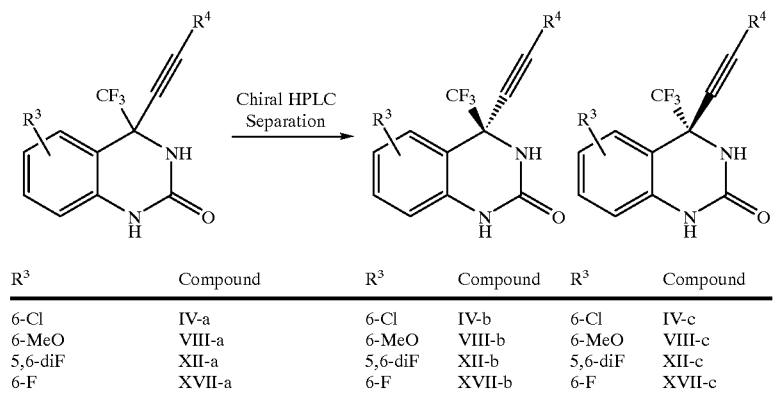

SCHEME 4: Chiral Resolution

| R³ | Compound | R³ | Compound | R³ | Compound |
|---|---|---|---|---|---|
| 6-Cl | IV-a | 6-Cl | IV-b | 6-Cl | IV-c |
| 6-MeO | VIII-a | 6-MeO | VIII-b | 6-MeO | VIII-c |
| 5,6-diF | XII-a | 5,6-diF | XII-b | 5,6-diF | XII-c |
| 6-F | XVII-a | 6-F | XVII-b | 6-F | XVII-c |

EXAMPLES 27 AND 28

Preparation of (−)-6-Chloro-4-cyclopropylethynyl-4-trifluoromethyl-3,4-dihydro-2(1H)-quinazolinone (Example 27) and (+)-6-Chloro-4-cyclopropylethynyl-4-trifluoromethyl-3,4-dihydro-2(1H)-quinazolinone (Example 28)

Resolution of IV-b,c from IV-a (R⁴=Cyclopropyl).

Chiral HPLC utilizing a Chiralcel OD column, 3% isopropanol, 5% $CH_2Cl_2$ and 92% hexanes at ambient temperature with a 1.0 mL/min flow rate and detection at 250 nm afforded seperation of IV-b from IV-c with enan tiomeric excesses of 99% and 99.4%, respectively. IV-b: mp 106–109° C.; $[\alpha]_D^{25}$ −60.34° (c=0.274, MeOH). IV-c: mp 105–107° C.; $[\alpha]_D^{25}$ +58.33° (c=0.288, MeOH).

EXAMPLES 29 AND 30

Preparation of (+)-4-Cyclopropylethynyl-5,6-difluoro-4-trifluoromethyl-3,4-dihydro-2(1H)-quinazolinone (Example 29) and (−)-4-Cyclopropylethynyl-5,6-difluoro-4-trifluoromethyl-3,4-dihydro-2(1H)-quinazolinone (Example 30)

Resolution of XII-b,c from XII-a ($R^4$=Cyclopropyl).

Chiral HPLC utilizing a Chiralpak AD column, 5% water and 95% methanol at ambient temperature with a 0.8 mL/min flow rate and detection at 250 nm afforded seperation of XII-b from XII-c with enantiomeric excesses of 100% and 99%, respectively. XII-b: mp 187° C.; $[\alpha]_D^{25}$ +1.46° (c=0.274, MeOH). XII-c: mp 187.5–188.8° C.; $[\alpha]_D^{25}$ −1.45° (c=0.278, MeOH).

EXAMPLES 31 AND 32

Preparation of (−)-5,6-Difluoro-4-isopropylethynyl-4-trifluoromethyl-3,4-dihydro-2(1H)-quinazolinone (Example 31) and (+)-5,6-Difluoro-4-isopropylethynyl-4-trifluoromethyl-3,4-dihydro-2(1H)-quinazolinone (Example 32)

Resolution of XII-b,c from XII-a ($R^4$=Isopropyl).

Chiral HPLC utilizing a Chiralpak AD column, 5% water and 95% methanol at ambient temperature with 0.5 mL/min flow rate and detection at 250 nm afforded seperation of XII-b from XII-c with enantiomeric excesses of 100% and 99%, respectively. XII-b: mp 155° C.; $[\alpha]_D^{25}$ −2.14° (c=0.280, MeOH). XII-c: 98° C.; $[\alpha]_D^{25}$ +4.45° (c=0.292, MeOH).

EXAMPLES 33 AND 34

Preparation of (−)-5,6-Difluoro-4-ethylethynyl-4-trifluoromethyl-3,4-dihydro-2(1H)-quinazolinone (Example 33) and (+)-5,6-Difluoro-4-ethylethynyl-4-trifluoromethyl-3,4-dihydro-2(1H)-quinazolinone (Example 34)

Resolution of XII-b,c from XII-a ($R^4$=Ethyl).

Chiral HPLC utilizing a AS column, 20% ethanol and 80% hexanes at ambient temperature with a 1.0 mL/min flow rate and detection at 250 nm afforded seperation of XII-b from XII-c with enantiomeric excesses of 100% and 99%, respectively. XII-b: mp 165–167° C. XII-c: mp 157–159° C.

EXAMPLES 35 AND 36

Preparation of 5,6-Difluoro-4-(2-hydroxyethyl)ethynyl-4-trifluoromethyl-3,4-dihydro-2(1H)-quinazolinone (Example 35) and 5,6-Difluoro-4-(1-hydroxyethyl)ethynyl-4-trifluoromethyl-3,4-dihydro-2(1H)-quinazolinone (Example 36)

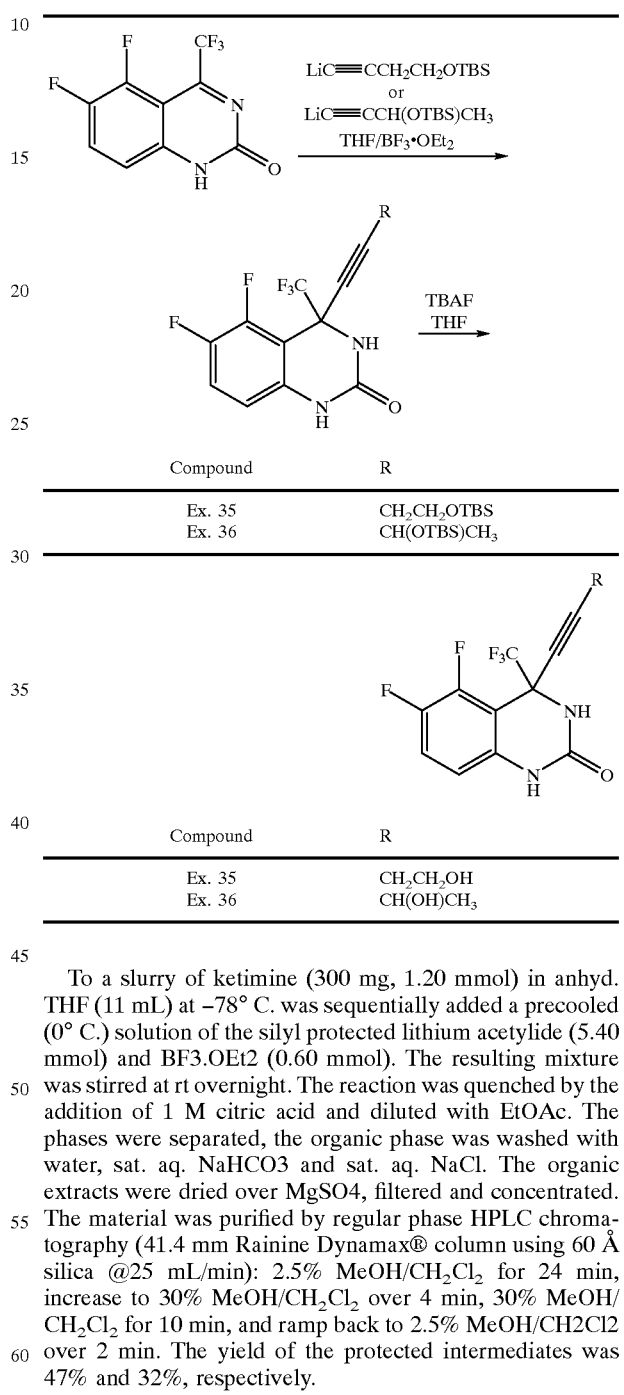

| Compound | R |
|---|---|
| Ex. 35 | $CH_2CH_2OTBS$ |
| Ex. 36 | $CH(OTBS)CH_3$ |

| Compound | R |
|---|---|
| Ex. 35 | $CH_2CH_2OH$ |
| Ex. 36 | $CH(OH)CH_3$ |

To a slurry of ketimine (300 mg, 1.20 mmol) in anhyd. THF (11 mL) at −78° C. was sequentially added a precooled (0° C.) solution of the silyl protected lithium acetylide (5.40 mmol) and BF3.OEt2 (0.60 mmol). The resulting mixture was stirred at rt overnight. The reaction was quenched by the addition of 1 M citric acid and diluted with EtOAc. The phases were separated, the organic phase was washed with water, sat. aq. NaHCO3 and sat. aq. NaCl. The organic extracts were dried over MgSO4, filtered and concentrated. The material was purified by regular phase HPLC chromatography (41.4 mm Rainine Dynamax® column using 60 Å silica @25 mL/min): 2.5% MeOH/$CH_2Cl_2$ for 24 min, increase to 30% MeOH/$CH_2Cl_2$ over 4 min, 30% MeOH/$CH_2Cl_2$ for 10 min, and ramp back to 2.5% MeOH/CH2Cl2 over 2 min. The yield of the protected intermediates was 47% and 32%, respectively.

Example 35-intermediate. Mp 62.9–64° C.; $^1$H NMR (300 MHz, acetone-$d_6$) δ 8.98 (br s, 1H), 7.41–7.32 (m, 2H), 6.83–6.78 (m, 1H), 3.74 (t, J=6.6 Hz, 2H), 2.47 (t, J=6.6 Hz, 2H), 0.81 (s, 9H), 0.00 (s, 6H); $^{19}$F NMR (282 MHz, acetone-$d_6$) δ −83.17, −135.16−−135.31, −148.09−−148.22; MS (CI) calc'd for C19H24F4N2O2Si: m/z 435.152723, found 435.151149; 435 (MH+, 94), 452 (M+NH4+, 100); Analysis calc'd for $C_{19}H_{23}F_5N_2O_2Si$: C, 52.52; H, 5.35; N, 6.46; found: C, 52.65; H, 5.29; N, 6.31.

Example 36-intermediate. $^1$H NMR (300 MHz, acetone-$d_6$) δ 8.96 (br s, 1H), 7.50 (br s, 1H), 7.37–7.28 (m, 1H), 6.79–6.74 (m, 1H), 4.61 (q, J=1.32, 6.6 Hz, 1H), 1.30 (d, J=6.6 Hz, 3H), 0.78 (s, 9H), 0.01 (s, 6H); $^{19}$F NMR (282 MHz, acetone-$d_6$) d −82.88—−82.95, −135.20—−135.42, −148.06—−148.23; MS (CI) calc'd for C19H24F5N2O2Si: m/z 435.152723, found 435.152927; 435 (MH+, 51), 452 (M+NH4+, 100); Analysis calc'd for $C_{19}H_{23}F_5N_2O_2Si$: C, 52.52; H, 5.35; N, 6.46; found: C, 52.54; H, 5.34; N, 6.69.

To a solution of the protected intermediate for Example 35 (0.56 mmol) in THF (1.1 mL) was added TBAF (0.62 mL of 1.0 M solution in THF). The resulting mixture was stirred at rt for 1 h, diluted with EtOAc, washed 1 N HCl, sat. aq. NaHCO$_3$, and sat. aq. NaCl. The organic extract was dried over MgSO$_4$, filtered and concentrated. The material was purified by regular phase HPLC chromatography (41.4 mm Rainin Dynamax® column using 60 Å silica @25 mL/min): 2.5% MeOH/CH$_2$Cl$_2$ for 24 min, increase to 30% MeOH/CH$_2$Cl$_2$ over 4 min, 30% MeOH/CH$_2$Cl$_2$ for 10 min, and ramp back to 2.5% MeOH/CH$_2$Cl$_2$ over 2 min. Example 35 was isolated in 82% yield.

Example 35. Mp 190–192° C.; $^1$H NMR (300 MHz, acetone-$d_6$) δ 9.05 (br s, 1H), 7.53 (br s, 1H), 7.45–7.36 (m, 1H), 6.88–6.83 (m, 1H), 4.01–3.98 (m, 1H), 3.68–3.64 (m, 2H), 2.50 (t, J=6.6 Hz, 2H); $^{19}$F NMR (282 MHz, acetone-$d_6$) δ −83.3, −135.68—−135.88, −148.10—−148.22; MS (CI) calc'd for $C_{13}H_{10}F_5N_2O_2$: m/z 321.066244, found 321.066479; 321 (MH+, 100); Analysis calc'd for $C_{13}H_9F_5N_2O_2$: C, 48.76; H, 2.83; N, 8.76; found: C, 49.05; H, 3.23; N, 8.38.

Example 36 was synthesized in an analogous manner to deliver the title compound in 88% yield. Mp 190–191° C.; $^1$H NMR (300 MHz, acetone-$d_6$) δ 9.06 (br s, 1H), 7.56 (br s, 1H), 7.46–7.37 (m, 1H), 6.88–6.83 (m, 1H), 4.58–4.57 (m, 2H), 1.39 (d, J=5.5 Hz, 3H); $^{19}$F NMR (282 MHz, acetone-$d_6$) δ −83.15, −135.40, −135.60, −148.08—−148.20; MS (CI) calc'd for $C_{13}H_{10}F_5N_2O_2$: m/z 321.066244, found 321.065983; 321 (MH+, 58), 338 (M+NH4+, 100); Analysis calc'd for $C_{13}H_9F_5N_2O_2$: C, 48.76; H, 2.83; N, 8.76; found: C, 48.84, H, 2.76; N, 8.63.

EXAMPLE 37

Preparation of (+)-4-E-Cyclopropylethenyl-5,6-difluoro-4-trifluoromethyl-3,4-dihydro-2(1H)-quinazolinone To a solution of XII-b (200 mg, 0.632 mmol) in anhyd. THF (1.3 mL) at rt was added a solution of lithium aluminium hydride (1.3 mL of 1.0 M solution in THF). The resulting mixture was stirred at rt overnight. The reaction was quenched by addition of 10% NaOH (3 mL) and water (3 mL). The mixture was diluted with EtOAc (30 mL) and the phases were separated. The organic phase was washed with sat. aq. NaCl, dried over MgSO$_4$, filtered and concentrated. The title compound was purified by regular phase HPLC (41.4 mm Rainin Dynamax® column using 60 Å silica): 2.5% MeOH/CH$_2$Cl$_2$ for 24 min, increase to 30% MeOH/CH$_2$Cl$_2$ over 4 min, 30% MeOH/CH$_2$Cl$_2$ for 10 min, and ramp back to 2.5% MeOH/CH$_2$Cl$_2$ over 2 min. Mp 80–83° C.; $^1$H NMR (300 MHz, acetone-$d_6$) d 9.07 (br s, 1H), 7.33 (q, J=8.8 Hz, 1H), 6.94 (br s, 1H), 6.84–6.79 (m, 1H), 6.27 (dd, J=15.6, 7.5 Hz, 1H), 5.67 (dd, J=15.2, 9.4 Hz, 1H), 1.65–1.56 (m, 1H), 0.80–0.71 (m, 2H), 0.50–0.42 (m, 2H); $^{19}$F NMR (282 MHz, acetone-$d_6$) d −82.68, −135.05, −148.49; MS (CI) calc'd for $C_{14}H_{12}F_5N_2O$: m/z 319.086979, found 319.087755; 319 (MH+, 100): $[α]_D^{20}$ +72.77° (c=0.382, MeOH); Analysis calc'd for $C_{14}H_{11}F_5N_2O$: C, 52.84; H, 3.48; N, 8.80; found: C, 53.02; H, 3.48; N, 8.61.

EXAMPLE 38

Preparation of (−)-6-Chloro-4-E-cyclopropylethenyl-4-trifluoromethyl-3,4-dihydro-2 (1H)-quinazolinone The title compound was prepared as described for Example 37 (starting from IV-b), except that it was purified using a Chiralcel OD column at 1.5 mL/min in 0.5% EtOH/20% CH$_2$Cl$_2$/79.5% hexanes. Mp 87–89° C.; $^1$H NMR (300 MHz, acetone-$d_6$) d 9.08 (br s, 1H), 7.40–7.25 (m, 2H), 7.04–6.90 (m, 2H), 6.28–6.18 (m, 1H), 5.64–5.52 (m, 1H), 1.68–1.55 (m, 1H), 0.83–0.71 (m, 2H), 0.53–0.41 (m, 2H); $^{19}$F NMR (282 MHz, acetone-$d_6$) d −81.67; MS (CI) calc'd for $C_{14}H_{13}ClF_3N_2O$: m/z 317.066851, found 317.065857; 317 (MH+, 100); $[α]_D^{20}$ −6.81° (c=0.382, MeOH); Analysis calc'd for $C_{14}H_{12}ClF_3N_2O$. 0.27 $C_3H_6O$: C, 53.52; H, 4.13; N, 8.43; found: C, 53.90; H, 4.07; N, 8.80.

TABLE 1*

| Ex.# | R$^3$ | R$^1$ | R$^2$ | R$^8$ | m.p. (° C.) | Mass Spec |
|---|---|---|---|---|---|---|
| 1 | 6-Cl | CF$_3$ | C≡C-cycPr | H | 86.6–88 | 332 (M+NH$_4^+$) |
| 2 | 6-Cl | CF$_3$ | C≡-iPr | H | 180 | 334 (M+NH$_4^+$) |
| 3 | 6-Cl | CF$_3$ | C≡C-2-Pyridyl | H | 105 | 352 (MH$^+$) |
| 4 | 6-Cl | CF$_3$ | C≡C—Et | H | 217–219 | 303 (MH$^+$) |
| 5 | 6-Cl | CF$_3$ | C≡C—Ph | H | 104–107 | 368 (M+NH$_4^+$) |
| 6 | 6-MeO | CF$_3$ | C≡C-cycPr | H | 208 | 311 (MH$^+$) |
| 7 | 6-MeO | CF$_3$ | C≡C-iPr | H | 228–229 | 313 (MH$^+$) |
| 8 | 6-MeO | CF$_3$ | C≡C-2-Pyridyl | H | 97–98 | 348 (MH$^+$) |
| 9 | 6-MeO | CF$_3$ | C=C-Ph | H | 206.2–207.7 | 347 (MH$^+$) |
| 10 | 5,6-diF | CF$_3$ | C≡C-cycPr | H | 101 dec. | 317 (MH$^+$) |
| 11 | 5,6-diF | CF$_3$ | C≡C-iPr | H | 79–80 | 319 (MH$^+$) |
| 12 | 5,6-diF | CF$_3$ | C≡C-2-Pyridyl | H | 219–220 | 354 (MH$^+$) |
| 13 | 5,6-diF | CF$_3$ | C≡C—Et | H | 191–194 | 305 (MH$^+$) |
| 14 | 5,6-diF | CF$_3$ | C≡C—Ph | H | 215–217 | 370 (M+NH$_4^+$) |
| 15 | 5,6-diF | CF$_3$ | CH$_2$CH$_2$CH(CH$_3$)$_2$ | H | 192–193 | 323 (MH$^+$) |
| 16 | 5,6-diF | CF$_3$ | CH$_2$CH$_2$CH$_2$CH$_3$ | H |  | 309 (MH+) |
| 17 | 6-F | CF$_3$ | C≡C-cycPr | H | 155 | 299 (MH$^+$) |
| 18 | 6-F | CF$_3$ | C≡C-iPr | H | 158 | 301 (MH$^+$) |
| 19 | 6-F | CF$_3$ | C≡C-2-Pyridyl | H | 155 | 336 (MH$^+$) |
| 20 | 6-F | CF$_3$ | C≡C—Et | H | 190 | 287 (MH$^+$) |
| 21 | 6-F | CF$_3$ | C≡C—Ph | H | 107 | 352 (M+NH$_4^+$) |
| 22 | 6-F | CF$_3$ | CH$_2$CH$_2$CH(CH$_3$)$_2$ | H | 179 | 305 (MH$^+$) |
| 23 | 6-F | CF$_3$ | CH$_2$CH$_2$-2-Pyridyl | H | 88 | 340 (MH$^+$) |
| 24 | 6-F | CF$_3$ | CH$_2$CH$_2$CH$_2$CH$_3$ | H | 198 | 291 (MH$^+$) |
| 25 | 6-F | CF$_3$ | CH$_2$CH$_2$Ph | H | 98 | 339 (MH$^+$) |
| 26 | 6-F | CF$_3$ | CH$_2$C≡C—CH$_3$ | H | 181 | 304 (M+NH$_4^+$) |
| 27(−) | 6-Cl | CF$_3$ | C≡C-cycPr | H | 106–109 | 313 (M$^-$) |
| 28(+) | 6-Cl | CF$_3$ | C≡C-cycPr | H | 105–107 | 313 (M$^-$) |
| 29(+) | 5,6-diF | CF$_3$ | C≡C-cycPr | H | 187 | 315 (M$^-$) |

TABLE 1*-continued

| Ex.# | R³ | R¹ | R² | R⁸ | m.p. (° C.) | Mass Spec |
|---|---|---|---|---|---|---|
| 30(−) | 5,6-diF | CF₃ | C≡C-cycPr | H | 188–189 | 315 (M⁻) |
| 31(−) | 5,6-diF | CF₃ | C≡C-iPr | H | 155 | 317 (M⁻) |
| 32(+) | 5,6-diF | CF₃ | C≡C-iPr | H | 98 | 317 (M⁻) |
| 33(−) | 5,6-diF | CF₃ | C≡C—Et | H | 165–167 | 303 (M⁻) |
| 34(+) | 5,6-diF | CF₃ | C≡C—Et | H | 157–159 | 303 (M⁻) |
| 35 | 5,6-diF | CF₃ | C≡CCH₂CH₂OH | H | 190–192 | 321 (MH⁺) |
| 36 | 5,6-diF | CF₃ | C≡C—CH(OH)Me | H | 190–191 | 338 (M+NH₄⁺) |
| 37(+) | 5,6-diF | CF₃ | C≡C-cycPr (E) | H | 80–83 | 319 (MH⁺) |
| 38(−) | 6-Cl | CF₃ | C≡C-cycPr (E) | H | 87–89 | 317 (MH⁺) |

*Unless otherwise indicated, stereochemistry is (+/−)

TABLE 2*

| Ex. # | R³ | R¹ | R² | R⁸ |
|---|---|---|---|---|
| 1 | 6-Cl | CF₃ | C≡CCH₂CH₂OH | H |
| 2 | 6-Cl | CF₃ | C≡C—CH(OH)Me | H |
| 3 | 6-Cl | CF₃ | C≡C-(2-Cl)Ph | H |
| 4 | 6-Cl | CF₃ | C≡C-(3-Cl)Ph | H |
| 5 | 6-Cl | CF₃ | C≡C-(4-Cl)Ph | H |
| 6 | 6-Cl | CF₃ | C≡C-(2-F)Ph | H |
| 7 | 6-Cl | CF₃ | C≡C-(3-F)Ph | H |
| 8 | 6-Cl | CF₃ | C≡C-(4-F)Ph | H |
| 9 | 6-Cl | CF₃ | C≡C-(2-OH)Ph | H |
| 10 | 6-Cl | CF₃ | C≡C-(3-OH)Ph | H |
| 11 | 6-Cl | CF₃ | C≡C-(4-OH)Ph | H |
| 12 | 6-Cl | CF₃ | C≡C-(2-OMe)Ph | H |
| 13 | 6-Cl | CF₃ | C≡C-(3-OMe)Ph | H |
| 14 | 6-Cl | CF₃ | C≡C-(4-OMe)Ph | H |
| 15 | 6-Cl | CF₃ | C≡C-(2-CN)Ph | H |
| 16 | 6-Cl | CF₃ | C≡C-(3-CN)Ph | H |
| 17 | 6-Cl | CF₃ | C≡C-(4-CN)Ph | H |
| 18 | 6-Cl | CF₃ | C≡C-(2-NO₂)Ph | H |
| 19 | 6-Cl | CF₃ | C≡C-(3-NO₂)Ph | H |
| 20 | 6-Cl | CF₃ | C≡C-(4-NO₂)Ph | H |
| 21 | 6-Cl | CF₃ | C≡C-(2-NH₂)Ph | H |
| 22 | 6-Cl | CF₃ | C≡C-(3-NH₂)Ph | H |
| 23 | 6-Cl | CF₃ | C≡C-(4-NH₂)Ph | H |
| 24 | 6-Cl | CF₃ | C≡C-(2-NMe₂)Ph | H |
| 25 | 6-Cl | CF₃ | C≡C-(3-NMe₂)Ph | H |
| 26 | 6-Cl | CF₃ | C≡C-(4-NMe₂)Ph | H |
| 27 | 6-Cl | CF₃ | C≡C-3-Pyridyl | H |
| 28 | 6-Cl | CF₃ | C≡C-4-Pyridyl | H |
| 29 | 6-Cl | CF₃ | C≡C-2-furanyl | H |
| 30 | 6-Cl | CF₃ | C≡C-3-furanyl | H |
| 31 | 6-Cl | CF₃ | C≡C-2-thienyl | H |
| 32 | 6-Cl | CF₃ | C≡C-3-thienyl | H |
| 33 | 6-Cl | CF₃ | C≡C-2-oxazolyl | H |
| 34 | 6-Cl | CF₃ | C≡C-2-thiazolyl | H |
| 35 | 6-Cl | CF₃ | C≡C-4-isoxazolyl | H |
| 36 | 6-Cl | CF₃ | C≡C-2-imidazolyl | H |
| 37 | 6-Cl | CF₃ | C≡CCH₂CH₂OH | H |
| 38 | 6-Cl | CF₃ | C≡C—CH(OH)Me | H |
| 39 | 6-Cl | CF₃ | C≡C-(2-Cl)Ph | H |
| 40 | 6-Cl | CF₃ | C≡C-(3-Cl)Ph | H |
| 41 | 6-Cl | CF₃ | C≡C-(4-Cl)Ph | H |
| 42 | 6-Cl | CF₃ | C≡C-(2-F)Ph | H |
| 43 | 6-Cl | CF₃ | C≡C-(3-F)Ph | H |
| 44 | 6-Cl | CF₃ | C≡C-(4-F)Ph | H |
| 45 | 6-Cl | CF₃ | C≡C-(2-OH)Ph | H |

TABLE 2*-continued

| Ex. # | R³ | R¹ | R² | R⁸ |
|---|---|---|---|---|
| 46 | 6-Cl | CF₃ | C≡C-(3-OH)Ph | H |
| 47 | 6-Cl | CF₃ | C≡C-(4-OH)Ph | H |
| 48 | 6-Cl | CF₃ | C≡C-(2-OMe)Ph | H |
| 49 | 6-Cl | CF₃ | C≡C-(3-OMe)Ph | H |
| 50 | 6-Cl | CF₃ | C≡C-(4-OMe)Ph | H |
| 51 | 6-Cl | CF₃ | C≡C-(2-CN)Ph | H |
| 52 | 6-Cl | CF₃ | C≡C-(3-CN)Ph | H |
| 53 | 6-Cl | CF₃ | C≡C-(4-CN)Ph | H |
| 54 | 6-Cl | CF₃ | C≡C-(2-NO₂)Ph | H |
| 55 | 6-Cl | CF₃ | C≡C-(3-NO₂)Ph | H |
| 56 | 6-Cl | CF₃ | C≡C-(4-NO₂)Ph | H |
| 57 | 6-Cl | CF₃ | C≡C-(2-NH₂)Ph | H |
| 58 | 6-Cl | CF₃ | C≡C-(3-NH₂)Ph | H |
| 59 | 6-Cl | CF₃ | C≡C-(4-NH₂)Ph | H |
| 60 | 6-Cl | CF₃ | C≡C-(2-NMe₂)Ph | H |
| 61 | 6-Cl | CF₃ | C≡C-(3-NMe₂)Ph | H |
| 62 | 6-Cl | CF₃ | C≡C-(4-NMe₂)Ph | H |
| 63 | 6-Cl | CF₃ | C≡C-3-Pyridyl | H |
| 64 | 6-Cl | CF₃ | C≡C-4-Pyridyl | H |
| 65 | 6-Cl | CF₃ | C≡C-2-furanyl | H |
| 66 | 6-Cl | CF₃ | C≡C-3-furanyl | H |
| 67 | 6-Cl | CF₃ | C≡C-2-thienyl | H |
| 68 | 6-Cl | CF₃ | C≡C-3-thienyl | H |
| 69 | 6-Cl | CF₃ | C≡C-2-oxazolyl | H |
| 70 | 6-Cl | CF₃ | C≡C-2-thiazolyl | H |
| 71 | 6-Cl | CF₃ | C≡C-4-isoxazolyl | H |
| 72 | 6-Cl | CF₃ | C≡C-2-imidazolyl | H |
| 73 | 6-Cl | CF₃ | CH₂CH₂-cycPr | H |
| 74 | 6-Cl | CF₃ | CH₂CH₂CH₂CH₂OH | H |
| 75 | 6-Cl | CF₃ | CH₂CH₂—CH(OH)Me | H |
| 76 | 6-Cl | CF₃ | CH₂CH₂—Ph | H |
| 77 | 6-Cl | CF₃ | CH₂CH₂-(2-Cl)Ph | H |
| 78 | 6-Cl | CF₃ | CH₂CH₂-(3-Cl)Ph | H |
| 79 | 6-Cl | CF₃ | CH₂CH₂-(4-Cl)Ph | H |
| 80 | 6-Cl | CF₃ | CH₂CH₂-(2-F)Ph | H |
| 81 | 6-Cl | CF₃ | CH₂CH₂-(3-F)Ph | H |
| 82 | 6-Cl | CF₃ | CH₂CH₂-(4-F)Ph | H |
| 83 | 6-Cl | CF₃ | CH₂CH₂-(2-OH)Ph | H |
| 84 | 6-Cl | CF₃ | CH₂CH₂-(3-OH)Ph | H |
| 85 | 6-Cl | CF₃ | CH₂CH₂-(4-OH)Ph | H |
| 86 | 6-Cl | CF₃ | CH₂CH₂-(2-OMe)Ph | H |
| 87 | 6-Cl | CF₃ | CH₂CH₂-(3-OMe)Ph | H |
| 88 | 6-Cl | CF₃ | CH₂CH₂-(4-OMe)Ph | H |
| 89 | 6-Cl | CF₃ | CH₂CH₂-(2-CN)Ph | H |
| 90 | 6-Cl | CF₃ | CH₂CH₂-(3-CN)Ph | H |
| 91 | 6-Cl | CF₃ | CH₂CH₂-(4-CN)Ph | H |
| 92 | 6-Cl | CF₃ | CH₂CH₂-(2-NO₂)Ph | H |
| 93 | 6-Cl | CF₃ | CH₂CH₂-(3-NO₂)Ph | H |
| 94 | 6-Cl | CF₃ | CH₂CH₂-(4-NO₂)Ph | H |
| 95 | 6-Cl | CF₃ | CH₂CH₂-(2-NH₂)Ph | H |
| 96 | 6-Cl | CF₃ | CH₂CH₂-(3-NH₂)Ph | H |
| 97 | 6-Cl | CF₃ | CH₂CH₂-(4-NH₂)Ph | H |
| 98 | 6-Cl | CF₃ | CH₂CH₂-(2-NMe₂)Ph | H |
| 99 | 6-Cl | CF₃ | CH₂CH₂-(3-NMe₂)Ph | H |
| 100 | 6-Cl | CF₃ | CH₂CH₂-(4-NMe₂)Ph | H |
| 101 | 6-Cl | CF₃ | CH₂CH₂-2-Pyridyl | H |
| 102 | 6-Cl | CF₃ | CH₂CH₂-3-Pyridyl | H |
| 103 | 6-Cl | CF₃ | CH₂CH₂-4-Pyridyl | H |
| 104 | 6-Cl | CF₃ | CH₂CH₂-2-furanyl | H |
| 105 | 6-Cl | CF₃ | CH₂CH₂-3-furanyl | H |
| 106 | 6-Cl | CF₃ | CH₂CH₂-4-furanyl | H |
| 107 | 6-Cl | CF₃ | CH₂CH₂-3-thienyl | H |
| 108 | 6-Cl | CF₃ | CH₂CH₂-2-oxazolyl | H |
| 109 | 6-Cl | CF₃ | CH₂CH₂-2-thiazolyl | H |
| 110 | 6-Cl | CF₃ | CH₂CH₂-4-isoxazolyl | H |
| 111 | 6-Cl | CF₃ | CH₂CH₂-2-imidazolyl | H |
| 112 | 6-Cl | CF₃ | C≡C-cycPr | CH₃ |
| 113 | 6-Cl | CF₃ | C≡C—Ph | CH₃ |

TABLE 2*-continued

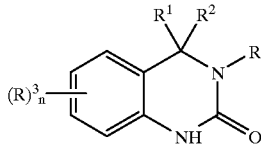

| Ex. # | R³ | R¹ | R² | R⁸ |
|---|---|---|---|---|
| 114 | 6-Cl | CF₃ | C≡C-2-Pyridyl | CH₃ |
| 115 | 6-Cl | CF₃ | C≡C-3-Pyridyl | CH₃ |
| 116 | 6-Cl | CF₃ | C≡C-4-Pyridyl | CH₃ |
| 117 | 6-Cl | CF₃ | C≡C-2-furanyl | CH₃ |
| 118 | 6-Cl | CF₃ | C≡C-3-furanyl | CH₃ |
| 119 | 6-Cl | CF₃ | C≡C-2-thienyl | CH₃ |
| 120 | 6-Cl | CF₃ | C≡C-3-thienyl | CH₃ |
| 121 | 6-Cl | CF₃ | C≡C-cycPr | CH₃ |
| 122 | 6-Cl | CF₃ | C≡C—Ph | CH₃ |
| 123 | 6-Cl | CF₃ | C≡C-2-Pyridyl | CH₃ |
| 124 | 6-Cl | CF₃ | C≡C-3-Pyridyl | CH₃ |
| 125 | 6-Cl | CF₃ | C≡C-4-Pyridyl | CH₃ |
| 126 | 6-Cl | CF₃ | C≡C-2-furanyl | CH₃ |
| 127 | 6-Cl | CF₃ | C≡C-3-furanyl | CH₃ |
| 128 | 6-Cl | CF₃ | C≡C-2-thienyl | CH₃ |
| 129 | 6-Cl | CF₃ | C≡C-3-thienyl | CH₃ |
| 130 | 6-Cl | CF₃ | CH₂CH₂-cycPr | CH₃ |
| 131 | 6-Cl | CF₃ | CH₂CH₂—Ph | CH₃ |
| 132 | 6-Cl | CF₃ | CH₂CH₂-2-Pyridyl | CH₃ |
| 133 | 6-Cl | CF₃ | CH₂CH₂-3-Pyridyl | CH₃ |
| 134 | 6-Cl | CF₃ | CH₂CH₂-4-Pyridyl | CH₃ |
| 135 | 6-Cl | CF₃ | CH₂CH₂-2-furanyl | CH₃ |
| 136 | 6-Cl | CF₃ | CH₂CH₂-3-furanyl | CH₃ |
| 137 | 6-Cl | CF₃ | CH₂CH₂-2-thienyl | CH₃ |
| 138 | 6-Cl | CF₃ | CH₂CH₂-3-thienyl | CH₃ |
| 139 | 6-Cl | CF₃ | C≡C-cycPr | CH₂CH₃ |
| 140 | 6-Cl | CF₃ | C≡C—Ph | CH₂CH₃ |
| 141 | 6-Cl | CF₃ | C≡C-2-Pyridyl | CH₂CH₃ |
| 142 | 6-Cl | CF₃ | C≡C-3-Pyridyl | CH₂CH₃ |
| 143 | 6-Cl | CF₃ | C≡C-4-Pyridyl | CH₂CH₃ |
| 144 | 6-Cl | CF₃ | C≡C-2-furanyl | CH₂CH₃ |
| 145 | 6-Cl | CF₃ | C≡C-3-furanyl | CH₂CH₃ |
| 146 | 6-Cl | CF₃ | C≡C-2-thienyl | CH₂CH₃ |
| 147 | 6-Cl | CF₃ | C≡C-3-thienyl | CH₂CH₃ |
| 148 | 6-Cl | CF₃ | C≡C-cycPr | CH₂CH₃ |
| 149 | 6-Cl | CF₃ | C≡C—Ph | CH₂CH₃ |
| 150 | 6-Cl | CF₃ | C≡C-2-Pyridyl | CH₂CH₃ |
| 151 | 6-Cl | CF₃ | C≡C-3-Pyridyl | CH₂CH₃ |
| 152 | 6-Cl | CF₃ | C≡C-4-Pyridyl | CH₂CH₃ |
| 153 | 6-Cl | CF₃ | C≡C-2-furanyl | CH₂CH₃ |
| 154 | 6-Cl | CF₃ | C≡C-3-furanyl | CH₂CH₃ |
| 155 | 6-Cl | CF₃ | C≡C-2-thienyl | CH₂CH₃ |
| 156 | 6-Cl | CF₃ | C≡C-3-thienyl | CH₂CH₃ |
| 157 | 6-Cl | CF₃ | CH₂CH₂-cycPr | CH₂CH₃ |
| 158 | 6-Cl | CF₃ | CH₂CH₂—Ph | CH₂CH₃ |
| 159 | 6-Cl | CF₃ | CH₂CH₂-2-Pyridyl | CH₂CH₃ |
| 160 | 6-Cl | CF₃ | CH₂CH₂-3-Pyridyl | CH₂CH₃ |
| 161 | 6-Cl | CF₃ | CH₂CH₂-4-Pyridyl | CH₂CH₃ |
| 162 | 6-Cl | CF₃ | CH₂CH₂-2-furanyl | CH₂CH₃ |
| 163 | 6-Cl | CF₃ | CH₂CH₂-3-furanyl | CH₂CH₃ |
| 164 | 6-Cl | CF₃ | CH₂CH₂-2-thienyl | CH₂CH₃ |
| 165 | 6-Cl | CF₃ | CH₂CH₂-3-thienyl | CH₂CH₃ |
| 166 | 6-MeO | CF₃ | C≡CCH₂CH₂OH | H |
| 167 | 6-MeO | CF₃ | C≡C—CH(OH)Me | H |
| 168 | 6-MeO | CF₃ | C≡C-(2-Cl)Ph | H |
| 169 | 6-MeO | CF₃ | C≡C-(3-Cl)Ph | H |
| 170 | 6-MeO | CF₃ | C≡C-(4-Cl)Ph | H |
| 171 | 6-MeO | CF₃ | C≡C-(2-F)Ph | H |
| 172 | 6-MeO | CF₃ | C≡C-(3-F)Ph | H |
| 173 | 6-MeO | CF₃ | C≡C-(4-F)Ph | H |
| 174 | 6-MeO | CF₃ | C≡C-(2-OH)Ph | H |
| 175 | 6-MeO | CF₃ | C≡C-(3-OH)Ph | H |
| 176 | 6-MeO | CF₃ | C≡C-(4-OH)Ph | H |
| 177 | 6-MeO | CF₃ | C≡C-(2-OMe)Ph | H |
| 178 | 6-MeO | CF₃ | C≡C-(3-OMe)Ph | H |
| 179 | 6-MeO | CF₃ | C≡C-(4-OMe)Ph | H |
| 180 | 6-MeO | CF₃ | C≡C-(2-CN)Ph | H |
| 181 | 6-MeO | CF₃ | C≡C-(3-CN)Ph | H |

TABLE 2*-continued

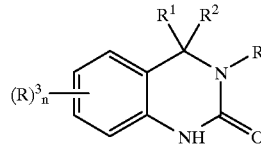

| Ex. # | R³ | R¹ | R² | R⁸ |
|---|---|---|---|---|
| 182 | 6-MeO | CF₃ | C≡C-(4-CN)Ph | H |
| 183 | 6-MeO | CF₃ | C≡C-(2-NO₂)Ph | H |
| 184 | 6-MeO | CF₃ | C≡C-(3-NO₂)Ph | H |
| 185 | 6-MeO | CF₃ | C≡C-(4-NO₂)Ph | H |
| 186 | 6-MeO | CF₃ | C≡C-(2-NH₂)Ph | H |
| 187 | 6-MeO | CF₃ | C≡C-(3-NH₂)Ph | H |
| 188 | 6-MeO | CF₃ | C≡C-(4-NH₂)Ph | H |
| 189 | 6-MeO | CF₃ | C≡C-(2-NMe₂)Ph | H |
| 190 | 6-MeO | CF₃ | C≡C-(3-NMe₂)Ph | H |
| 191 | 6-MeO | CF₃ | C≡C-(4-NMe₂)Ph | H |
| 192 | 6-MeO | CF₃ | C≡C-3-Pyridyl | H |
| 193 | 6-MeO | CF₃ | C≡C-4-Pyridyl | H |
| 194 | 6-MeO | CF₃ | C≡C-2-furanyl | H |
| 195 | 6-MeO | CF₃ | C≡C-3-furanyl | H |
| 196 | 6-MeO | CF₃ | C≡C-2-thienyl | H |
| 197 | 6-MeO | CF₃ | C≡C-3-thienyl | H |
| 198 | 6-MeO | CF₃ | C≡C-2-oxazolyl | H |
| 199 | 6-MeO | CF₃ | C≡-C-2-thiazolyl | H |
| 200 | 6-MeO | CF₃ | C≡C-4-isoxazolyl | H |
| 201 | 6-MeO | CF₃ | C≡C-2-imidazolyl | H |
| 202 | 6-MeO | CF₃ | C≡CCH₂CH₂OH | H |
| 203 | 6-MeO | CF₃ | C≡C—CH(OH)Me | H |
| 204 | 6-MeO | CF₃ | C≡C-(2-Cl)Ph | H |
| 205 | 6-MeO | CF₃ | C≡C-(3-Cl)Ph | H |
| 206 | 6-MeO | CF₃ | C≡C-(4-Cl)Ph | H |
| 207 | 6-MeO | CF₃ | C≡C-(2-F)Ph | H |
| 208 | 6-MeO | CF₃ | C≡C-(3-F)Ph | H |
| 209 | 6-MeO | CF₃ | C≡C-(4-F)Ph | H |
| 210 | 6-MeO | CF₃ | C≡C-(2-OH)Ph | H |
| 211 | 6-MeO | CF₃ | C≡C-(3-OH)Ph | H |
| 212 | 6-MeO | CF₃ | C≡C-(4-OH)Ph | H |
| 213 | 6-MeO | CF₃ | C≡C-(2-OMe)Ph | H |
| 214 | 6-MeO | CF₃ | C≡C-(3-OMe)Ph | H |
| 215 | 6-MeO | CF₃ | C≡C-(4-OMe)Ph | H |
| 216 | 6-MeO | CF₃ | C≡C-(2-CN)Ph | H |
| 217 | 6-MeO | CF₃ | C≡C-(3-CN)Ph | H |
| 218 | 6-MeO | CF₃ | C≡C-(4-CN)Ph | H |
| 219 | 6-MeO | CF₃ | C≡C-(2-NO₂)Ph | H |
| 220 | 6-MeO | CF₃ | C≡C-(3-NO₂)Ph | H |
| 221 | 6-MeO | CF₃ | C≡C-(4-NO₂)Ph | H |
| 222 | 6-MeO | CF₃ | C≡C-(2-NH₂)Ph | H |
| 223 | 6-MeO | CF₃ | C≡C-(3-NH₂)Ph | H |
| 224 | 6-MeO | CF₃ | C≡C-(4-NH₂)Ph | H |
| 225 | 6-MeO | CF₃ | C≡C-(2-NMe₂)Ph | H |
| 226 | 6-MeO | CF₃ | C≡C-(3-NMe₂)Ph | H |
| 227 | 6-MeO | CF₃ | C≡C-(4-NMe₂)Ph | H |
| 228 | 6-MeO | CF₃ | C≡C-3-Pyridyl | H |
| 229 | 6-MeO | CF₃ | C≡C-4-Pyridyl | H |
| 230 | 6-MeO | CF₃ | C≡C-2-furanyl | H |
| 231 | 6-MeO | CF₃ | C≡C-3-furanyl | H |
| 232 | 6-MeO | CF₃ | C≡C-2-thienyl | H |
| 233 | 6-MeO | CF₃ | C≡C-3-thienyl | H |
| 234 | 6-MeO | CF₃ | C≡C-2-oxazolyl | H |
| 235 | 6-MeO | CF₃ | C≡C-2-thiazolyl | H |
| 236 | 6-MeO | CF₃ | C≡C-4-isoxazolyl | H |
| 237 | 6-MeO | CF₃ | C≡C-2-imidazolyl | H |
| 238 | 6-MeO | CF₃ | CH₂CH₂-cycPr | H |
| 239 | 6-MeO | CF₃ | CH₂CH₂CH₂CH₂OH | H |
| 240 | 6-MeO | CF₃ | CH₂CH₂—CH(OH)Me | H |
| 241 | 6-MeO | CF₃ | CH₂CH₂—Ph | H |
| 242 | 6-MeO | CF₃ | CH₂CH₂-(2-Cl)Ph | H |
| 243 | 6-MeO | CF₃ | CH₂CH₂-(3-Cl)Ph | H |
| 244 | 6-MeO | CF₃ | CH₂CH₂-(4-Cl)Ph | H |
| 245 | 6-MeO | CF₃ | CH₂CH₂-(2-F)Ph | H |
| 246 | 6-MeO | CF₃ | CH₂CH₂-(3-F)Ph | H |
| 247 | 6-MeO | CF₃ | CH₂CH₂-(4-F)Ph | H |
| 248 | 6-MeO | CF₃ | CH₂CH₂-(2-OH)Ph | H |
| 249 | 6-MeO | CF₃ | CH₂CH₂-(3-OH)Ph | H |

TABLE 2*-continued

| Ex. # | R³ | R¹ | R² | R⁸ |
|---|---|---|---|---|
| 250 | 6-MeO | $CF_3$ | $CH_2CH_2$-(4-OH)Ph | H |
| 251 | 6-MeO | $CF_3$ | $CH_2CH_2$-(2-OMe)Ph | H |
| 252 | 6-MeO | $CF_3$ | $CH_2CH_2$-(3-OMe)Ph | H |
| 253 | 6-MeO | $CF_3$ | $CH_2CH_2$-(4-OMe)Ph | H |
| 254 | 6-MeO | $CF_3$ | $CH_2CH_2$-(2-CN)Ph | H |
| 255 | 6-MeO | $CF_3$ | $CH_2CH_2$-(3-CN)Ph | H |
| 256 | 6-MeO | $CF_3$ | $CH_2CH_2$-(4-CN)Ph | H |
| 257 | 6-MeO | $CF_3$ | $CH_2CH_2$-(2-$NO_2$)Ph | H |
| 258 | 6-MeO | $CF_3$ | $CH_2CH_2$-(3-$NO_2$)Ph | H |
| 259 | 6-MeO | $CF_3$ | $CH_2CH_2$-(4-$NO_2$)Ph | H |
| 260 | 6-MeO | $CF_3$ | $CH_2CH_2$-(2-$NH_2$)Ph | H |
| 261 | 6-MeO | $CF_3$ | $CH_2CH_2$-(3-$NH_2$)Ph | H |
| 262 | 6-MeO | $CF_3$ | $CH_2CH_2$-(4-$NH_2$)Ph | H |
| 263 | 6-MeO | $CF_3$ | $CH_2CH_2$-(2-$NMe_2$)Ph | H |
| 264 | 6-MeO | $CF_3$ | $CH_2CH_2$-(3-$NMe_2$)Ph | H |
| 265 | 6-MeO | $CF_3$ | $CH_2CH_2$-(4-$NMe_2$)Ph | H |
| 266 | 6-MeO | $CF_3$ | $CH_2CH_2$-2-Pyridyl | H |
| 267 | 6-MeO | $CF_3$ | $CH_2CH_2$-3-Pyridyl | H |
| 268 | 6-MeO | $CF_3$ | $CH_2CH_2$-4-Pyridyl | H |
| 269 | 6-MeO | $CF_3$ | $CH_2CH_2$-2-furanyl | H |
| 270 | 6-MeO | $CF_3$ | $CH_2CH_2$-3-furanyl | H |
| 271 | 6-MeO | $CF_3$ | $CH_2CH_2$-4-furanyl | H |
| 272 | 6-MeO | $CF_3$ | $CH_2CH_2$-3-thienyl | H |
| 273 | 6-MeO | $CF_3$ | $CH_2CH_2$-2-oxazolyl | H |
| 274 | 6-MeO | $CF_3$ | $CH_2CH_2$-2-thiazolyl | H |
| 275 | 6-MeO | $CF_3$ | $CH_2CH_2$-4-isoxazolyl | H |
| 276 | 6-MeO | $CF_3$ | $CH_2CH_2$-2-imidazolyl | H |
| 277 | 6-MeO | $CF_3$ | C≡C-cycPr | $CH_3$ |
| 278 | 6-MeO | $CF_3$ | C≡C—Ph | $CH_3$ |
| 279 | 6-MeO | $OF_3$ | C≡C-2-Pyridyl | $CH_3$ |
| 280 | 6-MeO | $CF_3$ | C≡C-3-Pyridyl | $CH_3$ |
| 281 | 6-MeO | $CF_3$ | C≡C-4-Pyridyl | $CH_3$ |
| 282 | 6-MeO | $CF_3$ | C≡C-2-furanyl | $CH_3$ |
| 283 | 6-MeO | $CF_3$ | C≡C-3-furanyl | $CH_3$ |
| 284 | 6-MeO | $CF_3$ | C≡C-2-thienyl | $CH_3$ |
| 285 | 6-MeO | $CF_3$ | C≡C-3-thienyl | $CH_3$ |
| 286 | 6-MeO | $CF_3$ | C≡C-cycPr | $CH_3$ |
| 287 | 6-MeO | $CF_3$ | C≡C—Ph | $CH_3$ |
| 288 | 6-MeO | $CF_3$ | C≡C-2-Pyridyl | $CH_3$ |
| 289 | 6-MeO | $CF_3$ | C≡C-3-Pyridyl | $CH_3$ |
| 290 | 6-MeO | $CF_3$ | C≡C-4-Pyridyl | $CH_3$ |
| 291 | 6-MeO | $CF_3$ | C≡C-2-furanyl | $CH_3$ |
| 292 | 6-MeO | $CF_3$ | C≡C-3-furanyl | $CH_3$ |
| 293 | 6-MeO | $CF_3$ | C≡C-2-thienyl | $CH_3$ |
| 294 | 6-MeO | $CF_3$ | C≡C-3-thienyl | $CH_3$ |
| 295 | 6-MeO | $CF_3$ | $CH_2CH_2$-cycPr | $CH_3$ |
| 296 | 6-MeO | $CF_3$ | $CH_2CH_2$—Ph | $CH_3$ |
| 297 | 6-MeO | $CF_3$ | $CH_2CH_2$-2-Pyridyl | $CH_3$ |
| 298 | 6-MeO | $CF_3$ | $CH_2CH_2$-3-Pyridyl | $CH_3$ |
| 299 | 6-MeO | $CF_3$ | $CH_2CH_2$-4-Pyridyl | $CH_3$ |
| 300 | 6-MeO | $CF_3$ | $CH_2CH_2$-2-furanyl | $CH_3$ |
| 301 | 6-MeO | $CF_3$ | $CH_2CH_2$-3-furanyl | $CH_3$ |
| 302 | 6-MeO | $CF_3$ | $CH_2CH_2$-2-thienyl | $CH_3$ |
| 303 | 6-MeO | $CF_3$ | $CH_2CH_2$-3-thienyl | $CH_3$ |
| 304 | 6-MeO | $CF_3$ | C≡C-cycPr | $CH_2CH_3$ |
| 305 | 6-MeO | $CF_3$ | C≡C—Ph | $CH_2CH_3$ |
| 306 | 6-MeO | $CF_3$ | C≡C-2-Pyridyl | $CH_2CH_3$ |
| 307 | 6-MeO | $CF_3$ | C≡C-3-Pyridyl | $CH_2CH_3$ |
| 308 | 6-MeO | $CF_3$ | C≡C-4-Pyridyl | $CH_2CH_3$ |
| 309 | 6-MeO | $CF_3$ | C≡C-2-furanyl | $CH_2CH_3$ |
| 310 | 6-MeO | $CF_3$ | C≡C-3-furanyl | $CH_2CH_3$ |
| 311 | 6-MeO | $CF_3$ | C≡C-2-thienyl | $CH_2CH_3$ |
| 312 | 6-MeO | $CF_3$ | C≡C-3-thienyl | $CH_2CH_3$ |
| 313 | 6-MeO | $CF_3$ | C≡C-cycPr | $CH_2CH_3$ |
| 314 | 6-MeO | $CF_3$ | C≡C—Ph | $CH_2CH_3$ |
| 315 | 6-MeO | $CF_3$ | C≡C-2-Pyridyl | $CH_2CH_3$ |
| 316 | 6-MeO | $CF_3$ | C≡C-3-Pyridyl | $CH_2CH_3$ |
| 317 | 6-MeO | $CF_3$ | C≡C-4-Pyridyl | $CH_2CH_3$ |
| 318 | 6-MeO | $CF_3$ | C≡C-2-furanyl | $CH_2CH_3$ |
| 319 | 6-MeO | $CF_3$ | C≡C-3-furanyl | $CH_2CH_3$ |
| 320 | 6-MeO | $CF_3$ | C≡C-2-thienyl | $CH_2CH_3$ |
| 321 | 6-MeO | $CF_3$ | C≡C-3-thienyl | $CH_2CH_3$ |
| 322 | 6-MeO | $CF_3$ | $CH_2CH_2$-cycPr | $CH_2CH_3$ |
| 323 | 6-MeO | $CF_3$ | $CH_2CH_2$—Ph | $CH_2CH_3$ |
| 324 | 6-MeO | $CF_3$ | $CH_2CH_2$-2-Pyridyl | $CH_2CH_3$ |
| 325 | 6-MeO | $CF_3$ | $CH_2CH_2$-3-Pyridyl | $CH_2CH_3$ |
| 326 | 6-MeO | $CF_3$ | $CH_2CH_2$-4-Pyridyl | $CH_2CH_3$ |
| 327 | 6-MeO | $CF_3$ | $CH_2CH_2$-2-furanyl | $CH_2CH_3$ |
| 328 | 6-MeO | $CF_3$ | $CH_2CH_2$-3-furanyl | $CH_2CH_3$ |
| 329 | 6-MeO | $CF_3$ | $CH_2CH_2$-2-thienyl | $CH_2CH_3$ |
| 330 | 6-MeO | $CF_3$ | $CH_2CH_2$-3-thienyl | $CH_2CH_3$ |
| 331 | 5,6-diF | $CF_3$ | C≡C-(2-Cl)Ph | H |
| 332 | 5,6-diF | $CF_3$ | C≡C-(3-Cl)Ph | H |
| 333 | 5,6-diF | $CF_3$ | C≡C-(4-Cl)Ph | H |
| 334 | 5,6-diF | $CF_3$ | C≡C-(2-F)Ph | H |
| 335 | 5,6-diF | $CF_3$ | C≡C-(3-F)Ph | H |
| 336 | 5,6-diF | $CF_3$ | C≡C-(4-F)Ph | H |
| 337 | 5,6-diF | $CF_3$ | C≡C-(2-OH)Ph | H |
| 338 | 5,6-diF | $CF_3$ | C≡C-(3-OH)Ph | H |
| 339 | 5,6-diF | $CF_3$ | C≡C-(4-OH)Ph | H |
| 340 | 5,6-diF | $CF_3$ | C≡C-(2-OMe)Ph | H |
| 341 | 5,6-diF | $CF_3$ | C≡C-(3-OMe)Ph | H |
| 342 | 5,6-diF | $CF_3$ | C≡C-(4-OMe)Ph | H |
| 343 | 5,6-diF | $CF_3$ | C≡C-(2-CN)Ph | H |
| 344 | 5,6-diF | $CF_3$ | C≡C-(3-CN)Ph | H |
| 345 | 5,6-diF | $CF_3$ | C≡C-(4-CN)Ph | H |
| 346 | 5,6-diF | $CF_3$ | C≡C-(2-$NO_2$)Ph | H |
| 347 | 5,6-diF | $CF_3$ | C≡C-(3-$NO_2$)Ph | H |
| 348 | 5,6-diF | $CF_3$ | C≡C-(4-$NO_2$)Ph | H |
| 349 | 5,6-diF | $CF_3$ | C≡C-(2-$NH_2$)Ph | H |
| 350 | 5,6-diF | $CF_3$ | C≡C-(3-$NH_2$)Ph | H |
| 351 | 5,6-diF | $CF_3$ | C≡C-(4-$NH_2$)Ph | H |
| 352 | 5,6-diF | $CF_3$ | C≡C-(2-$NMe_2$)Ph | H |
| 353 | 5,6-diF | $CF_3$ | C≡C-(3-$NMe_2$)Ph | H |
| 354 | 5,6-diF | $CF_3$ | C≡C-(4-$NMe_2$)Ph | H |
| 355 | 5,6-diF | $CF_3$ | C≡C-3-Pyridyl | H |
| 356 | 5,6-diF | $CF_3$ | C≡C-4-Pyridyl | H |
| 357 | 5,6-diF | $CF_3$ | C≡C-2-furanyl | H |
| 358 | 5,6-diF | $CF_3$ | C≡C-3-furanyl | H |
| 359 | 5,6-diF | $CF_3$ | C≡C-2-thienyl | H |
| 360 | 5,6-diF | $CF_3$ | C≡C-3-thienyl | H |
| 361 | 5,6-diF | $CF_3$ | C≡C-2-oxazolyl | H |
| 362 | 5,6-diF | $CF_3$ | C≡C-2-thiazolyl | H |
| 363 | 5,6-diF | $CF_3$ | C≡C-4-isoxazolyl | H |
| 364 | 5,6-diF | $CF_3$ | C≡C-2-imidazolyl | H |
| 365 | 5,6-diF | $CF_3$ | C≡C-(2-Cl)Ph | H |
| 366 | 5,6-diF | $CF_3$ | C≡C-(3-Cl)Ph | H |
| 367 | 5,6-diF | $CF_3$ | C≡C-(4-Cl)Ph | H |
| 368 | 5,6-diF | $CF_3$ | C≡C-(2-F)Ph | H |
| 369 | 5,6-diF | $CF_3$ | C≡C-(3-F)Ph | H |
| 370 | 5,6-diF | $CF_3$ | C≡C-(4-F)Ph | H |
| 371 | 5,6-diF | $CF_3$ | C≡C-(2-OH)Ph | H |
| 372 | 5,6-diF | $CF_3$ | C≡C-(3-OH)Ph | H |
| 373 | 5,6-diF | $CF_3$ | C≡C-(4-OH)Ph | H |
| 374 | 5,6-diF | $CF_3$ | C≡C-(2-OMe)Ph | H |
| 375 | 5,6-diF | $CF_3$ | C≡C-(3-OMe)Ph | H |
| 376 | 5,6-diF | $CF_3$ | C≡C-(4-OMe)Ph | H |
| 377 | 5,6-diF | $CF_3$ | C≡C-(2-CN)Ph | H |
| 378 | 5,6-diF | $CF_3$ | C≡C-(3-CN)Ph | H |
| 379 | 5,6-diF | $CF_3$ | C≡C-(4-CN)Ph | H |
| 380 | 5,6-diF | $CF_3$ | C≡C-(2-$NO_2$)Ph | H |
| 381 | 5,6-diF | $CF_3$ | C≡C-(3-$NO_2$)Ph | H |
| 382 | 5,6-diF | $CF_3$ | C≡C-(4-$NO_2$)Ph | H |
| 383 | 5,6-diF | $CF_3$ | C≡C-(2-$NH_2$)Ph | H |
| 384 | 5,6-diF | $CF_3$ | C≡C-(3-$NH_2$)Ph | H |
| 385 | 5,6-diF | $CF_3$ | C≡C-(4-$NH_2$)Ph | H |

TABLE 2*-continued

![Structure: quinazolinone with R1, R2 at 4-position, R8 on N3, NH-C=O, (R)3n on benzene ring]

| Ex. # | R³ | R¹ | R² | R⁸ |
|---|---|---|---|---|
| 386 | 5,6-diF | CF₃ | C≡C-(2-NMe₂)Ph | H |
| 387 | 5,6-diF | CF₃ | C≡C-(3-NMe₂)Ph | H |
| 388 | 5,6-diF | CF₃ | C≡C-(4-NMe₂)Ph | H |
| 389 | 5,6-diF | CF₃ | C≡C-3-Pyridyl | H |
| 390 | 5,6-diF | CF₃ | C≡C-4-Pyridyl | H |
| 391 | 5,6-diF | CF₃ | C≡C-2-furanyl | H |
| 392 | 5,6-diF | CF₃ | C≡C-3-furanyl | H |
| 393 | 5,6-diF | CF₃ | C≡C-2-thienyl | H |
| 394 | 5,6-diF | CF₃ | C≡C-3-thienyl | H |
| 395 | 5,6-diF | CF₃ | C≡C-2-oxazolyl | H |
| 396 | 5,6-diF | CF₃ | C≡C-2-thiazolyl | H |
| 397 | 5,6-diF | CF₃ | C≡C-4-isoxazolyl | H |
| 398 | 5,6-diF | CF₃ | C≡C-2-imidazolyl | H |
| 399 | 5,6-diF | CF₃ | CH₂CH₂-cycPr | H |
| 400 | 5,6-diF | CF₃ | CH₂CH₂CH₂CH₂OH | H |
| 401 | 5,6-diF | CF₃ | CH₂CH₂—CH(OH)Me | H |
| 402 | 5,6-diF | CF₃ | CH₂CH₂—Ph | H |
| 403 | 5,6-diF | CF₃ | CH₂CH₂-(2-Cl)Ph | H |
| 404 | 5,6-diF | CF₃ | CH₂CH₂-(3-Cl)Ph | H |
| 405 | 5,6-diF | CF₃ | CH₂CH₂-(4-Cl)Ph | H |
| 406 | 5,6-diF | CF₃ | CH₂CH₂-(2-F)Ph | H |
| 407 | 5,6-diF | CF₃ | CH₂CH₂-(3-F)Ph | H |
| 408 | 5,6-diF | CF₃ | CH₂CH₂-(4-F)Ph | H |
| 409 | 5,6-diF | CF₃ | CH₂CH₂-(2-OH)Ph | H |
| 410 | 5,6-diF | CF₃ | CH₂CH₂-(3-OH)Ph | H |
| 411 | 5,6-diF | CF₃ | CH₂CH₂-(4-OH)Ph | H |
| 412 | 5,6-diF | CF₃ | CH₂CH₂-(2-OMe)Ph | H |
| 413 | 5,6-diF | CF₃ | CH₂CH₂-(3-OMe)Ph | H |
| 414 | 5,6-diF | CF₃ | CH₂CH₂-(4-OMe)Ph | H |
| 415 | 5,6-diF | CF₃ | CH₂CH₂-(2-CN)Ph | H |
| 416 | 5,6-diF | CF₃ | CH₂CH₂-(3-CN)Ph | H |
| 417 | 5,6-diF | CF₃ | CH₂CH₂-(4-CN)Ph | H |
| 418 | 5,6-diF | CF₃ | CH₂CH₂-(2-NO₂)Ph | H |
| 419 | 5,6-diF | CF₃ | CH₂CH₂-(3-NO₂)Ph | H |
| 420 | 5,6-diF | CF₃ | CH₂CH₂-(4-NO₂)Ph | H |
| 421 | 5,6-diF | CF₃ | CH₂CH₂-(2-NH₂)Ph | H |
| 422 | 5,6-diF | CF₃ | CH₂CH₂-(3-NH₂)Ph | H |
| 423 | 5,6-diF | CF₃ | CH₂CH₂-(4-NH₂)Ph | H |
| 424 | 5,6-diF | CF₃ | CH₂CH₂-(2-NMe₂)Ph | H |
| 425 | 5,6-diF | CF₃ | CH₂CH₂-(3-NMe₂)Ph | H |
| 426 | 5,6-diF | CF₃ | CH₂CH₂-(4-NMe₂)Ph | H |
| 427 | 5,6-diF | CF₃ | CH₂CH₂-2-Pyridyl | H |
| 428 | 5,6-diF | CF₃ | CH₂CH₂-3-Pyridyl | H |
| 429 | 5,6-diF | CF₃ | CH₂CH₂-4-Pyridyl | H |
| 430 | 5,6-diF | CF₃ | CH₂CH₂-2-furanyl | H |
| 431 | 5,6-diF | CF₃ | CH₂CH₂-3-furanyl | H |
| 432 | 5,6-diF | CF₃ | CH₂CH₂-2-thienyl | H |
| 433 | 5,6-diF | CF₃ | CH₂CH₂-3-thienyl | H |
| 434 | 5,6-diF | CF₃ | CH₂CH₂-2-oxazolyl | H |
| 435 | 5,6-diF | CF₃ | CH₂CH₂-2-thiazolyl | H |
| 436 | 5,6-diF | CF₃ | CH₂CH₂-4-isoxazolyl | H |
| 437 | 5,6-diF | CF₃ | CH₂CH₂-2-imidazolyl | H |
| 438 | 5,6-diF | CF₃ | C≡C-cycPr | CH₃ |
| 439 | 5,6-diF | CF₃ | C≡C-2-Pyridyl | CH₃ |
| 440 | 5,6-diF | CF₃ | C≡C-3-Pyridyl | CH₃ |
| 441 | 5,6-diF | CF₃ | C≡C-4-Pyridyl | CH₃ |
| 442 | 5,6-diF | CF₃ | C≡C-2-furanyl | CH₃ |
| 443 | 5,6-diF | CF₃ | C≡C-3-furanyl | CH₃ |
| 444 | 5,6-diF | CF₃ | C≡C-2-thienyl | CH₃ |
| 445 | 5,6-diF | CF₃ | C≡C-3-thienyl | CH₃ |
| 446 | 5,6-diF | CF₃ | C≡C-cycPr | CH₃ |
| 447 | 5,6-diF | CF₃ | C≡C-2-Pyridyl | CH₃ |
| 448 | 5,6-diF | CF₃ | C≡C-3-Pyridyl | CH₃ |
| 449 | 5,6-diF | CF₃ | C≡C-4-Pyridyl | CH₃ |
| 450 | 5,6-diF | CF₃ | C≡C-2-furanyl | CH₃ |
| 451 | 5,6-diF | CF₃ | C≡C-3-furanyl | CH₃ |
| 452 | 5,6-diF | CF₃ | C≡C-2-thienyl | CH₃ |
| 453 | 5,6-diF | CF₃ | C≡C-3-thienyl | CH₃ |
| 454 | 5,6-diF | CF₃ | CH₂CH₂-cycPr | CH₃ |
| 455 | 5,6-diF | CF₃ | CH₂CH₂—Ph | CH₃ |
| 456 | 5,6-diF | CF₃ | CH₂CH₂-2-Pyridyl | CH₃ |
| 457 | 5,6-diF | CF₃ | CH₂CH₂-3-Pyridyl | CH₃ |
| 458 | 5,6-diF | CF₃ | CH₂CH₂-4-Pyridyl | CH₃ |
| 459 | 5,6-diF | CF₃ | CH₂CH₂-2-furanyl | CH₃ |
| 460 | 5,6-diF | CF₃ | CH₂CH₂-3-furanyl | CH₃ |
| 461 | 5,6-diF | CF₃ | CH₂CH₂-2-thienyl | CH₃ |
| 462 | 5,6-diF | CF₃ | CH₂CH₂-3-thienyl | CH₃ |
| 463 | 5,6-diF | CF₃ | C≡C-cycPr | CH₂CH₃ |
| 464 | 5,6-diF | CF₃ | C≡C—Ph | CH₂CH₃ |
| 465 | 5,6-diF | CF₃ | C≡C-2-Pyridyl | CH₂CH₃ |
| 466 | 5,6-diF | CF₃ | C≡C-3-Pyridyl | CH₂CH₃ |
| 467 | 5,6-diF | CF₃ | C≡C-4-Pyridyl | CH₂CH₃ |
| 468 | 5,6-diF | CF₃ | C≡C-2-furanyl | CH₂CH₃ |
| 469 | 5,6-diF | CF₃ | C≡C-3-furanyl | CH₂CH₃ |
| 470 | 5,6-diF | CF₃ | C≡C-2-thienyl | CH₂CH₃ |
| 471 | 5,6-diF | CF₃ | C≡C-3-thienyl | CH₂CH₃ |
| 472 | 5,6-diF | CF₃ | C≡C-cycPr | CH₂CH₃ |
| 473 | 5,6-diF | CF₃ | C≡C—Ph | CH₂CH₃ |
| 474 | 5,6-diF | CF₃ | C≡C-2-Pyridyl | CH₂CH₃ |
| 475 | 5,6-diF | CF₃ | C≡C-3-Pyridyl | CH₂CH₃ |
| 476 | 5,6-diF | CF₃ | C≡C-4-Pyridyl | CH₂CH₃ |
| 477 | 5,6-diF | CF₃ | C≡C-2-furanyl | CH₂CH₃ |
| 478 | 5,6-diF | CF₃ | C≡C-3-furanyl | CH₂CH₃ |
| 479 | 5,6-diF | CF₃ | C≡C-2-thienyl | CH₂CH₃ |
| 480 | 5,6-diF | CF₃ | C≡C-3-thienyl | CH₂CH₃ |
| 481 | 5,6-diF | CF₃ | CH₂CH₂-cycPr | CH₂CH₃ |
| 482 | 5,6-diF | CF₃ | CH₂CH₂—Ph | CH₂CH₃ |
| 483 | 5,6-diF | CF₃ | CH₂CH₂-2-Pyridyl | CH₂CH₃ |
| 484 | 5,6-diF | CF₃ | CH₂CH₂-3-Pyridyl | CH₂CH₃ |
| 485 | 5,6-diF | CF₃ | CH₂CH₂-4-Pyridyl | CH₂CH₃ |
| 486 | 5,6-diF | CF₃ | CH₂CH₂-2-furanyl | CH₂CH₃ |
| 487 | 5,6-diF | CF₃ | CH₂CH₂-3-furanyl | CH₂CH₃ |
| 488 | 5,6-diF | CF₃ | CH₂CH₂-2-thienyl | CH₂CH₃ |
| 489 | 5,6-diF | CF₃ | CH₂CH₂-3-thienyl | CH₂CH₃ |
| 490 | 5,6-diCl | CF₃ | C≡C-(2-Cl)Ph | H |
| 491 | 5,6-diCl | CF₃ | C≡C-(3-Cl)Ph | H |
| 492 | 5,6-diCl | CF₃ | C≡C-(4-Cl)Ph | H |
| 493 | 5,6-diCl | CF₃ | C≡C-(2-F)Ph | H |
| 494 | 5,6-diCl | CF₃ | C≡C-(3-F)Ph | H |
| 495 | 5,6-diCl | CF₃ | C≡C-(4-F)Ph | H |
| 496 | 5,6-diCl | CF₃ | C≡C-(2-OH)Ph | H |
| 497 | 5,6-diCl | CF₃ | C≡C-(3-OH)Ph | H |
| 498 | 5,6-diCl | CF₃ | C≡C-(4-OH)Ph | H |
| 499 | 5,6-diCl | CF₃ | C≡C-(2-OMe)Ph | H |
| 500 | 5,6-diCl | CF₃ | C≡C-(3-OMe)Ph | H |
| 501 | 5,6-diCl | CF₃ | C≡C-(4-OMe)Ph | H |
| 502 | 5,6-diCl | CF₃ | C≡C-(2-CN)Ph | H |
| 503 | 5,6-diCl | CF₃ | C≡C-(3-CN)Ph | H |
| 504 | 5,6-diCl | CF₃ | C≡C-(4-CN)Ph | H |
| 505 | 5,6-diCl | CF₃ | C≡C-(2-NO₂)Ph | H |
| 506 | 5,6-diCl | CF₃ | C≡C-(3-NO₂)Ph | H |
| 507 | 5,6-diCl | CF₃ | C≡C-(4-NO₂)Ph | H |
| 508 | 5,6-diCl | CF₃ | C≡C-(2-NH₂)Ph | H |
| 509 | 5,6-diCl | CF₃ | C≡C-(3-NH₂)Ph | H |
| 510 | 5,6-diCl | CF₃ | C≡C-(4-NH₂)Ph | H |
| 511 | 5,6-diCl | CF₃ | C≡C-(2-NMe₂)Ph | H |
| 512 | 5,6-diCl | CF₃ | C≡C-(3-NMe₂)Ph | H |
| 513 | 5,6-diCl | CF₃ | C≡C-(4-NMe₂)Ph | H |
| 514 | 5,6-diCl | CF₃ | C≡C-3-Pyridyl | H |
| 515 | 5,6-diCl | CF₃ | C≡C-4-Pyridyl | H |
| 516 | 5,6-diCl | CF₃ | C≡C-2-furanyl | H |
| 517 | 5,6-diCl | CF₃ | C≡C-3-furanyl | H |
| 518 | 5,6-diCl | CF₃ | C≡C-2-thienyl | H |
| 519 | 5,6-diCl | CF₃ | C≡C-3-thienyl | H |
| 520 | 5,6-diCl | CF₃ | C≡C-2-oxazolyl | H |
| 521 | 5,6-diCl | CF₃ | C≡C-2-thiazolyl | H |

TABLE 2*-continued

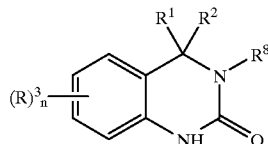

| Ex. # | R³ | R¹ | R² | R⁸ |
|---|---|---|---|---|
| 522 | 5,6-diCl | CF₃ | C≡C-4-isoxazolyl | H |
| 523 | 5,6-diCl | CF₃ | C≡C-2-imidazolyl | H |
| 524 | 5,6-diCl | CF₃ | C≡C-(2-Cl)Ph | H |
| 525 | 5,6-diCl | CF₃ | C≡C-(3-Cl)Ph | H |
| 526 | 5,6-diCl | CF₃ | C≡C-(4-Cl)Ph | H |
| 527 | 5,6-diCl | CF₃ | C≡C-(2-F)Ph | H |
| 528 | 5,6-diCl | CF₃ | C≡C-(3-F)Ph | H |
| 529 | 5,6-diCl | CF₃ | C≡C-(4-F)Ph | H |
| 530 | 5,6-diCl | CF₃ | C≡C-(2-OH)Ph | H |
| 531 | 5,6-diCl | CF₃ | C≡C-(3-OH)Ph | H |
| 532 | 5,6-diCl | CF₃ | C≡C-(4-OH)Ph | H |
| 533 | 5,6-diCl | CF₃ | C≡C-(2-OMe)Ph | H |
| 534 | 5,6-diCl | CF₃ | C≡C-(3-OMe)Ph | H |
| 535 | 5,6-diCl | CF₃ | C≡C-(4-OMe)Ph | H |
| 536 | 5,6-diCl | CF₃ | C≡C-(2-CN)Ph | H |
| 537 | 5,6-diCl | CF₃ | C≡C-(3-CN)Ph | H |
| 538 | 5,6-diCl | CF₃ | C≡C-(4-CN)Ph | H |
| 539 | 5,6-diCl | CF₃ | C≡C-(2-NO₂)Ph | H |
| 540 | 5,6-diCl | CF₃ | C≡C-(3-NO₂)Ph | H |
| 541 | 5,6-diCl | CF₃ | C≡C-(4-NO₂)Ph | H |
| 542 | 5,6-diCl | CF₃ | C≡C-(2-NH₂)Ph | H |
| 543 | 5,6-diCl | CF₃ | C≡C-(3-NH₂)Ph | H |
| 544 | 5,6-diCl | CF₃ | C≡C-(4-NH₂)Ph | H |
| 545 | 5,6-diCl | CF₃ | C≡C-(2-NMe₂)Ph | H |
| 546 | 5,6-diCl | CF₃ | C≡C-(3-NMe₂)Ph | H |
| 547 | 5,6-diCl | CF₃ | C≡C-(4-NMe₂)Ph | H |
| 548 | 5,6-diCl | CF₃ | C≡C-3-Pyridyl | H |
| 549 | 5,6-diCl | CF₃ | C≡C-4-Pyridyl | H |
| 550 | 5,6-diCl | CF₃ | C≡C-2-furanyl | H |
| 551 | 5,6-diCl | CF₃ | C≡C-3-furanyl | H |
| 552 | 5,6-diCl | CF₃ | C≡C-2-thienyl | H |
| 553 | 5,6-diCl | CF₃ | C≡C-3-thienyl | H |
| 554 | 5,6-diCl | CF₃ | C≡C-2-oxazolyl | H |
| 555 | 5,6-diCl | CF₃ | C≡C-2-thiazolyl | H |
| 556 | 5,6-diCl | CF₃ | C≡C-4-isoxazolyl | H |
| 557 | 5,6-diCl | CF₃ | C≡C-2-imidazolyl | H |
| 558 | 5,6-diCl | CF₃ | CH₂CH₂-cycPr | H |
| 559 | 5,6-diCl | CF₃ | CH₂CH₂CH₂CH₂OH | H |
| 560 | 5,6-diCl | CF₃ | CH₂CH₂—CH(OH)Me | H |
| 561 | 5,6-diCl | CF₃ | CH₂CH₂—Ph | H |
| 562 | 5,6-diCl | CF₃ | CH₂CH₂-(2-Cl)Ph | H |
| 563 | 5,6-diCl | CF₃ | CH₂CH₂-(3-Cl)Ph | H |
| 564 | 5,6-diCl | CF₃ | CH₂CH₂-(4-Cl)Ph | H |
| 565 | 5,6-diCl | CF₃ | CH₂CH₂-(2-F)Ph | H |
| 566 | 5,6-diCl | CF₃ | CH₂CH₂-(3-F)Ph | H |
| 567 | 5,6-diCl | CF₃ | CH₂CH₂-(4-F)Ph | H |
| 568 | 5,6-diCl | CF₃ | CH₂CH₂-(2-OH)Ph | H |
| 569 | 5,6-diCl | CF₃ | CH₂CH₂-(3-OH)Ph | H |
| 570 | 5,6-diCl | CF₃ | CH₂CH₂-(4-OH)Ph | H |
| 571 | 5,6-diCl | CF₃ | CH₂CH₂-(2-OMe)Ph | H |
| 572 | 5,6-diCl | CF₃ | CH₂CH₂-(3-OMe)Ph | H |
| 573 | 5,6-diCl | CF₃ | CH₂CH₂-(4-OMe)Ph | H |
| 574 | 5,6-diCl | CF₃ | CH₂CH₂-(2-CN)Ph | H |
| 575 | 5,6-diCl | CF₃ | CH₂CH₂-(3-CN)Ph | H |
| 576 | 5,6-diCl | CF₃ | CH₂CH₂-(4-CN)Ph | H |
| 577 | 5,6-diCl | CF₃ | CH₂CH₂-(2-NO₂)Ph | H |
| 578 | 5,6-diCl | CF₃ | CH₂CH₂-(3-NO₂)Ph | H |
| 579 | 5,6-diCl | CF₃ | CH₂CH₂-(4-NO₂)Ph | H |
| 580 | 5,6-diCl | CF₃ | CH₂CH₂-(2-NH₂)Ph | H |
| 581 | 5,6-diCl | CF₃ | CH₂CH₂-(3-NH₂)Ph | H |
| 582 | 5,6-diCl | CF₃ | CH₂CH₂-(4-NH₂)Ph | H |
| 583 | 5,6-diCl | CF₃ | CH₂CH₂-(2-NMe₂)Ph | H |
| 584 | 5,6-diCl | CF₃ | CH₂CH₂-(3-NMe₂)Ph | H |
| 585 | 5,6-diCl | CF₃ | CH₂CH₂-(4-NMe₂)Ph | H |
| 586 | 5,6-diCl | CF₃ | CH₂CH₂-2-Pyridyl | H |
| 587 | 5,6-diCl | CF₃ | CH₂CH₂-3-Pyridyl | H |
| 588 | 5,6-diCl | CF₃ | CH₂CH₂-4-Pyridyl | H |
| 589 | 5,6-diCl | CF₃ | CH₂CH₂-2-furanyl | H |

TABLE 2*-continued

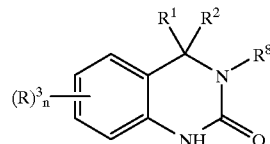

| Ex. # | R³ | R¹ | R² | R⁸ |
|---|---|---|---|---|
| 590 | 5,6-diCl | CF₃ | CH₂CH₂-3-furanyl | H |
| 591 | 5,6-diCl | CF₃ | CH₂CH₂-2-thienyl | H |
| 592 | 5,6-diCl | CF₃ | CH₂CH₂-3-thienyl | H |
| 593 | 5,6-diCl | CF₃ | CH₂CH₂-2-oxazolyl | H |
| 594 | 5,6-diCl | CF₃ | CH₂CH₂-2-thiazolyl | H |
| 595 | 5,6-diCl | CF₃ | CH₂CH₂-4-isoxazolyl | H |
| 596 | 5,6-diCl | CF₃ | CH₂CH₂-2-imidazolyl | H |
| 597 | 5,6-diCl | CF₃ | C≡C-cycPr | CH₃ |
| 598 | 5,6-diCl | CF₃ | C≡C-2-Pyridyl | CH₃ |
| 599 | 5,6-diCl | CF₃ | C≡C-3-Pyridyl | CH₃ |
| 600 | 5,6-diCl | CF₃ | C≡C-4-Pyridyl | CH₃ |
| 601 | 5,6-diCl | CF₃ | C≡C-2-furanyl | CH₃ |
| 602 | 5,6-diCl | CF₃ | C≡C-3-furanyl | CH₃ |
| 603 | 5,6-diCl | CF₃ | C≡C-2-thienyl | CH₃ |
| 604 | 5,6-diCl | CF₃ | C≡C-3-thienyl | CH₃ |
| 605 | 5,6-diCl | CF₃ | C≡C-cycPr | CH₃ |
| 606 | 5,6-diCl | CF₃ | C≡C-2-Pyridyl | CH₃ |
| 607 | 5,6-diCl | CF₃ | C≡C-3-Pyridyl | CH₃ |
| 608 | 5,6-diCl | CF₃ | C≡C-4-Pyridyl | CH₃ |
| 609 | 5,6-diCl | CF₃ | C≡C-2-furanyl | CH₃ |
| 610 | 5,6-diCl | CF₃ | C≡C-3-furanyl | CH₃ |
| 611 | 5,6-diCl | CF₃ | C≡C-2-thienyl | CH₃ |
| 612 | 5,6-diCl | CF₃ | C≡C-3-thienyl | CH₃ |
| 613 | 5,6-diCl | CF₃ | CH₂CH₂-cycPr | CH₃ |
| 614 | 5,6-diCl | CF₃ | CH₂CH₂—Ph | CH₃ |
| 615 | 5,6-diCl | CF₃ | CH₂CH₂-2-Pyridyl | CH₃ |
| 616 | 5,6-diCl | CF₃ | CH₂CH₂-3-Pyridyl | CH₃ |
| 617 | 5,6-diCl | CF₃ | CH₂CH₂-4-Pyridyl | CH₃ |
| 618 | 5,6-diCl | CF₃ | CH₂CH₂-2-furanyl | CH₃ |
| 619 | 5,6-diCl | CF₃ | CH₂CH₂-3-furanyl | CH₃ |
| 620 | 5,6-diCl | CF₃ | CH₂CH₂-2-thienyl | CH₃ |
| 621 | 5,6-diCl | CF₃ | CH₂CH₂-3-thienyl | CH₃ |
| 622 | 5,6-diCl | CF₃ | C≡C-cycPr | CH₂CH₃ |
| 623 | 5,6-diCl | CF₃ | C≡C—Ph | CH₂CH₃ |
| 624 | 5,6-diCl | CF₃ | C≡C-2-Pyridyl | CH₂CH₃ |
| 625 | 5,6-diCl | CF₃ | C≡C-3-Pyridyl | CH₂CH₃ |
| 626 | 5,6-diCl | CF₃ | C≡C-4-Pyridyl | CH₂CH₃ |
| 627 | 5,6-diCl | CF₃ | C≡C-2-furanyl | CH₂CH₃ |
| 628 | 5,6-diCl | CF₃ | C≡C-3-furanyl | CH₂CH₃ |
| 629 | 5,6-diCl | CF₃ | C≡C-2-thienyl | CH₂CH₃ |
| 630 | 5,6-diCl | CF₃ | C≡C-3-thienyl | CH₂CH₃ |
| 631 | 5,6-diCl | CF₃ | C≡C-cycPr | CH₂CH₃ |
| 632 | 5,6-diCl | CF₃ | C≡C—Ph | CH₂CH₃ |
| 633 | 5,6-diCl | CF₃ | C≡C-2-Pyridyl | CH₂CH₃ |
| 634 | 5,6-diCl | CF₃ | C≡C-3-Pyridyl | CH₂CH₃ |
| 635 | 5,6-diCl | CF₃ | C≡C-4-Pyridyl | CH₂CH₃ |
| 636 | 5,6-diCl | CF₃ | C≡C-2-furanyl | CH₂CH₃ |
| 637 | 5,6-diCl | CF₃ | C≡C-3-furanyl | CH₂CH₃ |
| 638 | 5,6-diCl | CF₃ | C≡C-2-thienyl | CH₂CH₃ |
| 639 | 5,6-diCl | CF₃ | C≡C-3-thienyl | CH₂CH₃ |
| 640 | 5,6-diCl | CF₃ | CH₂CH₂-cycPr | CH₂CH₃ |
| 641 | 5,6-diCl | CF₃ | CH₂CH₂—Ph | CH₂CH₃ |
| 642 | 5,6-diCl | CF₃ | CH₂CH₂-2-Pyridyl | CH₂CH₃ |
| 643 | 5,6-diCl | CF₃ | CH₂CH₂-3-Pyridyl | CH₂CH₃ |
| 644 | 5,6-diCl | CF₃ | CH₂CH₂-4-Pyridyl | CH₂CH₃ |
| 645 | 5,6-diCl | CF₃ | CH₂CH₂-2-furanyl | CH₂CH₃ |
| 646 | 5,6-diCl | CF₃ | CH₂CH₂-3-furanyl | CH₂CH₃ |
| 647 | 5,6-diCl | CF₃ | CH₂CH₂-2-thienyl | CH₂CH₃ |
| 648 | 5,6-diCl | CF₃ | CH₂CH₂-3-thienyl | CH₂CH₃ |
| 649 | 6-F | CF₃ | C≡CCH₂CH₂OH | H |
| 650 | 6-F | CF₃ | C≡C—CH(OH)Me | H |
| 651 | 6-F | CF₃ | C≡C-(2-Cl)Ph | H |
| 652 | 6-F | CF₃ | C≡C-(3-Cl)Ph | H |
| 653 | 6-F | CF₃ | C≡C-(4-Cl)Ph | H |
| 654 | 6-F | CF₃ | C≡C-(2-F)Ph | H |
| 655 | 6-F | CF₃ | C≡C-(3-F)Ph | H |
| 656 | 6-F | CF₃ | C≡C-(4-F)Ph | H |
| 657 | 6-F | CF₃ | C≡C-(2-OH)Ph | H |

TABLE 2*-continued

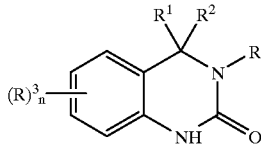

| Ex. # | R³ | R¹ | R² | R⁸ |
|---|---|---|---|---|
| 658 | 6-F | CF₃ | C≡C-(3-OH)Ph | H |
| 659 | 6-F | CF₃ | C≡C-(4-OH)Ph | H |
| 660 | 6-F | CF₃ | C≡C-(2-OMe)Ph | H |
| 661 | 6-F | CF₃ | C≡C-(3-OMe)Ph | H |
| 662 | 6-F | CF₃ | C≡C-(4-OMe)Ph | H |
| 663 | 6-F | CF₃ | C≡C-(2-CN)Ph | H |
| 664 | 6-F | CF₃ | C≡C-(3-CN)Ph | H |
| 665 | 6-F | CF₃ | C≡C-(4-CN)Ph | H |
| 666 | 6-F | CF₃ | C≡C-(2-NO₂)Ph | H |
| 667 | 6-F | CF₃ | C≡C-(3-NO₂)Ph | H |
| 668 | 6-F | CF₃ | C≡C-(4-NO₂)Ph | H |
| 669 | 6-F | CF₃ | C≡C-(2-NH₂)Ph | H |
| 670 | 6-F | CF₃ | C≡C-(3-NH₂)Ph | H |
| 671 | 6-F | CF₃ | C≡C-(4-NH₂)Ph | H |
| 672 | 6-F | CF₃ | C≡C-(2-NMe₂)Ph | H |
| 673 | 6-F | CF₃ | C≡C-(3-NMe₂)Ph | H |
| 674 | 6-F | CF₃ | C≡C-(4-NMe₂)Ph | H |
| 675 | 6-F | CF₃ | C≡C-3-Pyridyl | H |
| 676 | 6-F | CF₃ | C≡C-4-Pyridyl | H |
| 677 | 6-F | CF₃ | C≡C-2-furanyl | H |
| 678 | 6-F | CF₃ | C≡C-3-furanyl | H |
| 679 | 6-F | CF₃ | C≡C-2-thienyl | H |
| 680 | 6-F | CF₃ | C≡C-3-thienyl | H |
| 681 | 6-F | CF₃ | C≡C-2-oxazolyl | H |
| 682 | 6-F | CF₃ | C≡C-2-thiazolyl | H |
| 683 | 6-F | CF₃ | C≡C-4-isoxazolyl | H |
| 684 | 6-F | CF₃ | C≡C-2-imidazolyl | H |
| 685 | 6-F | CF₃ | C≡CCH₂CH₂OH | H |
| 686 | 6-F | CF₃ | C≡C—CH(OH)Me | H |
| 687 | 6-F | CF₃ | C=C-(2-Cl)Ph | H |
| 688 | 6-F | CF₃ | C=C-(3-Cl)Ph | H |
| 689 | 6-F | CF₃ | C=C-(4-Cl)Ph | H |
| 690 | 6-F | CF₃ | C=C-(2-F)Ph | H |
| 691 | 6-F | CF₃ | C=C-(3-F)Ph | H |
| 692 | 6-F | CF₃ | C=C-(4-F)Ph | H |
| 693 | 6-F | CF₃ | C=C-(2-OH)Ph | H |
| 694 | 6-F | CF₃ | C=C-(3-OH)Ph | H |
| 695 | 6-F | CF₃ | C=C-(4-OH)Ph | H |
| 696 | 6-F | CF₃ | C=C-(2-OMe)Ph | H |
| 697 | 6-F | CF₃ | C=C-(3-OMe)Ph | H |
| 698 | 6-F | CF₃ | C=C-(4-OMe)Ph | H |
| 699 | 6-F | CF₃ | C=C-(2-CN)Ph | H |
| 700 | 6-F | CF₃ | C=C-(3-CN)Ph | H |
| 701 | 6-F | CF₃ | C=C-(4-CN)Ph | H |
| 702 | 6-F | CF₃ | C=C-(2-NO₂)Ph | H |
| 703 | 6-F | CF₃ | C=C-(3-NO₂)Ph | H |
| 704 | 6-F | CF₃ | C=C-(4-NO₂)Ph | H |
| 705 | 6-F | CF₃ | C=C-(2-NH₂)Ph | H |
| 706 | 6-F | CF₃ | C=C-(3-NH₂)Ph | H |
| 707 | 6-F | CF₃ | C=C-(4-NH₂)Ph | H |
| 708 | 6-F | CF₃ | C=C-(2-NMe₂)Ph | H |
| 709 | 6-F | CF₃ | C=C-(3-NMe₂)Ph | H |
| 710 | 6-F | CF₃ | C=C-(4-NMe₂)Ph | H |
| 711 | 6-F | CF₃ | C=C-3-Pyridyl | H |
| 712 | 6-F | CF₃ | C=C-4-Pyridyl | H |
| 713 | 6-F | CF₃ | C=C-2-furanyl | H |
| 714 | 6-F | CF₃ | C=C-3-furanyl | H |
| 715 | 6-F | CF₃ | C=C-2-thienyl | H |
| 716 | 6-F | CF₃ | C=C-3-thienyl | H |
| 717 | 6-F | CF₃ | C=C-2-oxazolyl | H |
| 718 | 6-F | CF₃ | C=C-2-thiazolyl | H |
| 719 | 6-F | CF₃ | C=C-4-isoxazolyl | H |
| 720 | 6-F | CF₃ | C=C-2-imidazolyl | H |
| 721 | 6-F | CF₃ | CH₂CH₂-cycPr | H |
| 722 | 6-F | CF₃ | CH₂CH₂CH₂CH₂OH | H |
| 723 | 6-F | CF₃ | CH₂CH₂—CH(OH)Me | H |
| 724 | 6-F | CF₃ | CH₂CH₂-(2-Cl)Ph | H |
| 725 | 6-F | CF₃ | CH₂CH₂-(3-Cl)Ph | H |

TABLE 2*-continued

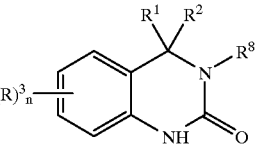

| Ex. # | R³ | R¹ | R² | R⁸ |
|---|---|---|---|---|
| 726 | 6-F | CF₃ | CH₂CH₂-(4-Cl)Ph | H |
| 727 | 6-F | CF₃ | CH₂CH₂-(2-F)Ph | H |
| 728 | 6-F | CF₃ | CH₂CH₂-(3-F)Ph | H |
| 729 | 6-F | CF₃ | CH₂CH₂-(4-F)Ph | H |
| 730 | 6-F | CF₃ | CH₂CH₂-(2-OH)Ph | H |
| 731 | 6-F | CF₃ | CH₂CH₂-(3-OH)Ph | H |
| 732 | 6-F | CF₃ | CH₂CH₂-(4-OH)Ph | H |
| 733 | 6-F | CF₃ | CH₂CH₂-(2-OMe)Ph | H |
| 734 | 6-F | CF₃ | CH₂CH₂-(3-OMe)Ph | H |
| 735 | 6-F | CF₃ | CH₂CH₂-(4-OMe)Ph | H |
| 736 | 6-F | CF₃ | CH₂CH₂-(2-CN)Ph | H |
| 737 | 6-F | CF₃ | CH₂CH₂-(3-CN)Ph | H |
| 738 | 6-F | CF₃ | CH₂CH₂-(4-CN)Ph | H |
| 739 | 6-F | CF₃ | CH₂CH₂-(2-NO₂)Ph | H |
| 740 | 6-F | CF₃ | CH₂CH₂-(3-NO₂)Ph | H |
| 741 | 6-F | CF₃ | CH₂CH₂-(4-NO₂)Ph | H |
| 742 | 6-F | CF₃ | CH₂CH₂-(2-NH₂)Ph | H |
| 743 | 6-F | CF₃ | CH₂CH₂-(3-NH₂)Ph | H |
| 744 | 6-F | CF₃ | CH₂CH₂-(4-NH₂)Ph | H |
| 745 | 6-F | CF₃ | CH₂CH₂-(2-NMe₂)Ph | H |
| 746 | 6-F | CF₃ | CH₂CH₂-(3-NMe₂)Ph | H |
| 747 | 6-F | CF₃ | CH₂CH₂-(4-NMe₂)Ph | H |
| 748 | 6-F | CF₃ | CH₂CH₂-3-Pyridyl | H |
| 749 | 6-F | CF₃ | CH₂CH₂-4-Pyridyl | H |
| 750 | 6-F | CF₃ | CH₂CH₂-2-furanyl | H |
| 751 | 6-F | CF₃ | CH₂CH₂-3-furanyl | H |
| 752 | 6-F | CF₃ | CH₂CH₂-2-thienyl | H |
| 753 | 6-F | CF₃ | CH₂CH₂-3-thienyl | H |
| 754 | 6-F | CF₃ | CH₂CH₂-2-oxazolyl | H |
| 755 | 6-F | CF₃ | CH₂CH₂-2-thiazolyl | H |
| 756 | 6-F | CF₃ | CH₂CH₂-4-isoxazolyl | H |
| 757 | 6-F | CF₃ | CH₂CH₂-2-imidazolyl | H |
| 758 | 6-F | CF₃ | C≡C-cycPr | CH₃ |
| 759 | 6-F | CF₃ | C≡C-iPr | CH₃ |
| 760 | 6-F | CF₃ | C≡C—Pr | CH₃ |
| 761 | 6-F | CF₃ | C≡C—Bu | CH₃ |
| 762 | 6-F | CF₃ | C≡C-iBu | CH₃ |
| 763 | 6-F | CF₃ | C≡C-tBu | CH₃ |
| 764 | 6-F | CF₃ | C≡C—Et | CH₃ |
| 765 | 6-F | CF₃ | C≡C—Me | CH₃ |
| 766 | 6-F | CF₃ | C≡C—Ph | CH₃ |
| 767 | 6-F | CF₃ | C≡C-2-Pyridyl | CH₃ |
| 768 | 6-F | CF₃ | C≡C-3-Pyridyl | CH₃ |
| 769 | 6-F | CF₃ | C≡C-4-Pyridyl | CH₃ |
| 770 | 6-F | CF₃ | C≡C-2-furanyl | CH₃ |
| 771 | 6-F | CF₃ | C≡C-3-furanyl | CH₃ |
| 772 | 6-F | CF₃ | C≡C-2-thienyl | CH₃ |
| 773 | 6-F | CF₃ | C≡C-3-thienyl | CH₃ |
| 774 | 6-F | CF₃ | C=C-cycPr | CH₃ |
| 775 | 6-F | CF₃ | C=C-iPr | CH₃ |
| 776 | 6-F | CF₃ | C=C—Pr | CH₃ |
| 777 | 6-F | CF₃ | C=C—Bu | CH₃ |
| 778 | 6-F | CF₃ | C=C-iBu | CH₃ |
| 779 | 6-F | CF₃ | C=C-tBu | CH₃ |
| 780 | 6-F | CF₃ | C=C—Et | CH₃ |
| 781 | 6-F | CF₃ | C=C—Me | CH₃ |
| 782 | 6-F | CF₃ | C=C—Ph | CH₃ |
| 783 | 6-F | CF₃ | C=C-2-Pyridyl | CH₃ |
| 784 | 6-F | CF₃ | C=C-3-Pyridyl | CH₃ |
| 785 | 6-F | CF₃ | C=C-4-Pyridyl | CH₃ |
| 786 | 6-F | CF₃ | C=C-2-furanyl | CH₃ |
| 787 | 6-F | CF₃ | C=C-3-furanyl | CH₃ |
| 788 | 6-F | CF₃ | C=C-2-thienyl | CH₃ |
| 789 | 6-F | CF₃ | C=C-3-thienyl | CH₃ |
| 790 | 6-F | CF₃ | CH₂CH₂-cycPr | CH₃ |
| 791 | 6-F | CF₃ | CH₂CH₂—Ph | CH₃ |
| 792 | 6-F | CF₃ | CH₂CH₂-2-Pyridyl | CH₃ |
| 793 | 6-F | CF₃ | CH₂CH₂-3-Pyridyl | CH₃ |

TABLE 2*-continued

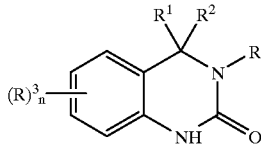

| Ex. # | R³ | R¹ | R² | R⁸ |
|---|---|---|---|---|
| 794 | 6-F | CF₃ | CH₂CH₂-4-Pyridyl | CH₃ |
| 795 | 6-F | CF₃ | CH₂CH₂-2-furanyl | CH₃ |
| 796 | 6-F | CF₃ | CH₂CH₂-3-furanyl | CH₃ |
| 797 | 6-F | CF₃ | CH₂CH₂-2-thienyl | CH₃ |
| 798 | 6-F | CF₃ | CH₂CH₂-3-thienyl | CH₃ |
| 799 | 6-F | CF₃ | C≡C-cycPr | CH₂CH₃ |
| 800 | 6-F | CF₃ | C≡C—Ph | CH₂CH₃ |
| 801 | 6-F | CF₃ | C≡C-2-Pyridyl | CH₂CH₃ |
| 802 | 6-F | CF₃ | C≡C-3-Pyridyl | CH₂CH₃ |
| 803 | 6-F | CF₃ | C≡C-4-Pyridyl | CH₂CH₃ |
| 804 | 6-F | CF₃ | C≡C-2-furanyl | CH₂CH₃ |
| 805 | 6-F | CF₃ | C≡C-3-furanyl | CH₂CH₃ |
| 806 | 6-F | CF₃ | C≡C-2-thienyl | CH₂CH₃ |
| 807 | 6-F | CF₃ | C≡C-3-thienyl | CH₂CH₃ |
| 808 | 6-F | CF₃ | C≡C-cycPr | CH₂CH₃ |
| 809 | 6-F | CF₃ | C≡C—Ph | CH₂CH₃ |
| 810 | 6-F | CF₃ | C≡C-2-Pyridyl | CH₂CH₃ |
| 811 | 6-F | CF₃ | C≡C-3-Pyridyl | CH₂CH₃ |
| 812 | 6-F | CF₃ | C≡C-4-Pyridyl | CH₂CH₃ |
| 813 | 6-F | CF₃ | C≡C-2-furanyl | CH₂CH₃ |
| 814 | 6-F | CF₃ | C≡C-3-furanyl | CH₂CH₃ |
| 815 | 6-F | CF₃ | C≡C-2-thienyl | CH₂CH₃ |
| 816 | 6-F | CF₃ | C≡C-3-thienyl | CH₂CH₃ |
| 817 | 6-F | CF₃ | CH₂CH₂-cycPr | CH₂CH₃ |
| 818 | 6-F | CF₃ | CH₂CH₂—Ph | CH₂CH₃ |
| 819 | 6-F | CF₃ | CH₂CH₂-2-Pyridyl | CH₂CH₃ |
| 820 | 6-F | CF₃ | CH₂CH₂-3-Pyridyl | CH₂CH₃ |
| 821 | 6-F | CF₃ | CH₂CH₂-4-Pyridyl | CH₂CH₃ |
| 822 | 6-F | CF₃ | CH₂CH₂-2-furanyl | CH₂CH₃ |
| 823 | 6-F | CF₃ | CH₂CH₂-3-furanyl | CH₂CH₃ |
| 824 | 6-F | CF₃ | CH₂CH₂-2-thienyl | CH₂CH₃ |
| 825 | 6-F | CF₃ | CH₂CH₂-3-thienyl | CH₂CH₃ |
| 826 | 5-Cl | CF₃ | C≡C-cycPr | H |
| 827 | 5-Cl | CF₃ | C≡CCH₂CH₂OH | H |
| 828 | 5-Cl | CF₃ | C≡C—CH(OH)Me | H |
| 829 | 5-Cl | CF₃ | C≡C—Ph | H |
| 830 | 5-Cl | CF₃ | C≡C-(2-Cl)Ph | H |
| 831 | 5-Cl | CF₃ | C≡C-(3-Cl)Ph | H |
| 832 | 5-Cl | CF₃ | C≡C-(4-Cl)Ph | H |
| 833 | 5-Cl | CF₃ | C≡C-(2-F)Ph | H |
| 834 | 5-Cl | CF₃ | C≡C-(3-F)Ph | H |
| 835 | 5-Cl | CF₃ | C≡C-(4-F)Ph | H |
| 836 | 5-Cl | CF₃ | C≡C-(2-OH)Ph | H |
| 837 | 5-Cl | CF₃ | C≡C-(3-OH)Ph | H |
| 838 | 5-Cl | CF₃ | C≡C-(4-OH)Ph | H |
| 839 | 5-Cl | CF₃ | C≡C-(2-OMe)Ph | H |
| 840 | 5-Cl | CF₃ | C≡C-(3-OMe)Ph | H |
| 841 | 5-Cl | CF₃ | C≡C-(4-OMe)Ph | H |
| 842 | 5-Cl | CF₃ | C≡C-(2-CN)Ph | H |
| 843 | 5-Cl | CF₃ | C≡C-(3-CN)Ph | H |
| 844 | 5-Cl | CF₃ | C≡C-(4-CN)Ph | H |
| 845 | 5-Cl | CF₃ | C≡C-(2-NO₂)Ph | H |
| 846 | 5-Cl | CF₃ | C≡C-(3-NO₂)Ph | H |
| 847 | 5-Cl | CF₃ | C≡C-(4-NO₂)Ph | H |
| 848 | 5-Cl | CF₃ | C≡C-(2-NH₂)Ph | H |
| 849 | 5-Cl | CF₃ | C≡C-(3-NH₂)Ph | H |
| 850 | 5-Cl | CF₃ | C≡C-(4-NH₂)Ph | H |
| 851 | 5-Cl | CF₃ | C≡C-(2-NMe₂)Ph | H |
| 852 | 5-Cl | CF₃ | C≡C-(3-NMe₂)Ph | H |
| 853 | 5-Cl | CF₃ | C≡C-(4-NMe₂)Ph | H |
| 854 | 5-Cl | CF₃ | C≡C-2-Pyridyl | H |
| 855 | 5-Cl | CF₃ | C≡C-2-Pyridyl | H |
| 856 | 5-Cl | CF₃ | C≡C-3-Pyridyl | H |
| 857 | 5-Cl | CF₃ | C≡C-4-Pyridyl | H |
| 858 | 5-Cl | CF₃ | C≡C-2-furanyl | H |
| 859 | 5-Cl | CF₃ | C≡C-3-furanyl | H |
| 860 | 5-Cl | CF₃ | C≡C-2-thienyl | H |
| 861 | 5-Cl | CF₃ | C≡C-3-thienyl | H |

TABLE 2*-continued

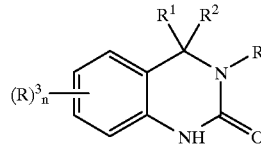

| Ex. # | R³ | R¹ | R² | R⁸ |
|---|---|---|---|---|
| 862 | 5-Cl | CF₃ | C≡C-2-oxazolyl | H |
| 863 | 5-Cl | CF₃ | C≡C-2-thiazolyl | H |
| 864 | 5-Cl | CF₃ | C≡C-4-isoxazolyl | H |
| 865 | 5-Cl | CF₃ | C≡C-2-imidazolyl | H |
| 866 | 5-Cl | CF₃ | C≡C-cycPr | H |
| 867 | 5-Cl | CF₃ | C≡CCH₂CH₂OH | H |
| 868 | 5-Cl | CF₃ | C≡C—CH(OH)Me | H |
| 869 | 5-Cl | CF₃ | C≡C—Ph | H |
| 870 | 5-Cl | CF₃ | C≡C-(2-Cl)Ph | H |
| 871 | 5-Cl | CF₃ | C≡C-(3-Cl)Ph | H |
| 872 | 5-Cl | CF₃ | C≡C-(4-Cl)Ph | H |
| 873 | 5-Cl | CF₃ | C≡C-(2-F)Ph | H |
| 874 | 5-Cl | CF₃ | C≡C-(3-F)Ph | H |
| 875 | 5-Cl | CF₃ | C≡C-(4-F)Ph | H |
| 876 | 5-Cl | CF₃ | C≡C-(2-OH)Ph | H |
| 877 | 5-Cl | CF₃ | C≡C-(3-OH)Ph | H |
| 878 | 5-Cl | CF₃ | C≡C-(4-OH)Ph | H |
| 879 | 5-Cl | CF₃ | C≡C-(2-OMe)Ph | H |
| 880 | 5-Cl | CF₃ | C≡C-(3-OMe)Ph | H |
| 881 | 5-Cl | CF₃ | C≡C-(4-OMe)Ph | H |
| 882 | 5-Cl | CF₃ | C≡C-(2-CN)Ph | H |
| 883 | 5-Cl | CF₃ | C≡C-(3-CN)Ph | H |
| 884 | 5-Cl | CF₃ | C≡C-(4-CN)Ph | H |
| 885 | 5-Cl | CF₃ | C≡C-(2-NO₂)Ph | H |
| 886 | 5-Cl | CF₃ | C≡C-(3-NO₂)Ph | H |
| 887 | 5-Cl | CF₃ | C≡C-(4-NO₂)Ph | H |
| 888 | 5-Cl | CF₃ | C≡C-(2-NH₂)Ph | H |
| 889 | 5-Cl | CF₃ | C≡C-(3-NH₂)Ph | H |
| 890 | 5-Cl | CF₃ | C≡C-(4-NH₂)Ph | H |
| 891 | 5-Cl | CF₃ | C≡C-(2-NMe₂)Ph | H |
| 892 | 5-Cl | CF₃ | C≡C-(3-NMe₂)Ph | H |
| 893 | 5-Cl | CF₃ | C≡C-(4-NMe₂)Ph | H |
| 894 | 5-Cl | CF₃ | C≡C-2-Pyridyl | H |
| 895 | 5-Cl | CF₃ | C≡C-2-Pyridyl | H |
| 896 | 5-Cl | CF₃ | C≡C-3-Pyridyl | H |
| 897 | 5-Cl | CF₃ | C≡C-4-Pyridyl | H |
| 898 | 5-Cl | CF₃ | C≡C-2-furanyl | H |
| 899 | 5-Cl | CF₃ | C≡C-3-furanyl | H |
| 900 | 5-Cl | CF₃ | C≡C-2-thienyl | H |
| 901 | 5-Cl | CF₃ | C≡C-3-thienyl | H |
| 902 | 5-Cl | CF₃ | C≡C-2-oxazolyl | H |
| 903 | 5-Cl | CF₃ | C≡C-2-thiazolyl | H |
| 904 | 5-Cl | CF₃ | C≡C-4-isoxazolyl | H |
| 905 | 5-Cl | CF₃ | C≡C-2-imidazolyl | H |
| 906 | 5-Cl | CF₃ | CH₂CH₂-cycPr | H |
| 907 | 5-Cl | CF₃ | CH₂CH₂CH₂CH₂OH | H |
| 908 | 5-Cl | CF₃ | CH₂CH₂—CH(OH)Me | H |
| 909 | 5-Cl | CF₃ | CH₂CH₂Ph | H |
| 910 | 5-Cl | CF₃ | CH₂CH₂-(2-Cl)Ph | H |
| 911 | 5-Cl | CF₃ | CH₂CH₂-(3-Cl)Ph | H |
| 912 | 5-Cl | CF₃ | CH₂CH₂-(4-Cl)Ph | H |
| 913 | 5-Cl | CF₃ | CH₂CH₂-(2-F)Ph | H |
| 914 | 5-Cl | CF₃ | CH₂CH₂-(3-F)Ph | H |
| 915 | 5-Cl | CF₃ | CH₂CH₂-(4-F)Ph | H |
| 916 | 5-Cl | CF₃ | CH₂CH₂-(2-OH)Ph | H |
| 917 | 5-Cl | CF₃ | CH₂CH₂-(3-OH)Ph | H |
| 918 | 5-Cl | CF₃ | CH₂CH₂-(4-OH)Ph | H |
| 919 | 5-Cl | CF₃ | CH₂CH₂-(2-OMe)Ph | H |
| 920 | 5-Cl | CF₃ | CH₂CH₂-(3-OMe)Ph | H |
| 921 | 5-Cl | CF₃ | CH₂CH₂-(4-OMe)Ph | H |
| 922 | 5-Cl | CF₃ | CH₂CH₂-(2-CN)Ph | H |
| 923 | 5-Cl | CF₃ | CH₂CH₂-(3-CN)Ph | H |
| 924 | 5-Cl | CF₃ | CH₂CH₂-(4-CN)Ph | H |
| 925 | 5-Cl | CF₃ | CH₂CH₂-(2-NO₂)Ph | H |
| 926 | 5-Cl | CF₃ | CH₂CH₂-(3-NO₂)Ph | H |
| 927 | 5-Cl | CF₃ | CH₂CH₂-(4-NO₂)Ph | H |
| 928 | 5-Cl | CF₃ | CH₂CH₂-(2-NH₂)Ph | H |
| 929 | 5-Cl | CF₃ | CH₂CH₂-(3-NH₂)Ph | H |

TABLE 2*-continued

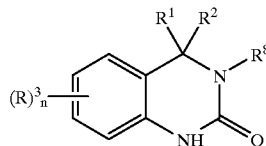

| Ex. # | R³ | R¹ | R² | R⁸ |
|---|---|---|---|---|
| 930 | 5-Cl | $CF_3$ | $CH_2CH_2$-(4-$NH_2$)Ph | H |
| 931 | 5-Cl | $CF_3$ | $CH_2CH_2$-(2-$NMe_2$)Ph | H |
| 932 | 5-Cl | $CF_3$ | $CH_2CH_2$-(3-$NMe_2$)Ph | H |
| 933 | 5-Cl | $CF_3$ | $CH_2CH_2$-(4-$NMe_2$)Ph | H |
| 934 | 5-Cl | $CF_3$ | $CH_2CH_2$-2-Pyridyl | H |
| 935 | 5-Cl | $CF_3$ | $CH_2CH_2$-3-Pyridyl | H |
| 936 | 5-Cl | $CF_3$ | $CH_2CH_2$-4-Pyridyl | H |
| 937 | 5-Cl | $CF_3$ | $CH_2CH_2$-2-furanyl | H |
| 938 | 5-Cl | $CF_3$ | $CH_2CH_2$-3-furanyl | H |
| 939 | 5-Cl | $CF_3$ | $CH_2CH_2$-2-thienyl | H |
| 940 | 5-Cl | $CF_3$ | $CH_2CH_2$-3-thienyl | H |
| 941 | 5-Cl | $CF_3$ | $CH_2CH_2$-2-oxazolyl | H |
| 942 | 5-Cl | $CF_3$ | $CH_2CH_2$-2-thiazolyl | H |
| 943 | 5-Cl | $CF_3$ | $CH_2CH_2$-4-isoxazolyl | H |
| 944 | 5-Cl | $CF_3$ | $CH_2CH_2$-2-imidazolyl | H |
| 945 | 5-Cl | $CF_3$ | C≡C-cycPr | $CH_3$ |
| 946 | 5-Cl | $CF_3$ | C≡C—Ph | $CH_3$ |
| 947 | 5-Cl | $CF_3$ | C≡C-2-Pyridyl | $CH_3$ |
| 948 | 5-Cl | $CF_3$ | C≡C-3-Pyridyl | $CH_3$ |
| 949 | 5-Cl | $CF_3$ | C≡C-4-Pyridyl | $CH_3$ |
| 950 | 5-Cl | $CF_3$ | C≡C-2-furanyl | $CH_3$ |
| 951 | 5-Cl | $CF_3$ | C≡C-3-furanyl | $CH_3$ |
| 952 | 5-Cl | $CF_3$ | C≡C-2-thienyl | $CH_3$ |
| 953 | 5-Cl | $CF_3$ | C≡C-3-thienyl | $CH_3$ |
| 954 | 5-Cl | $CF_3$ | C≡C-cycPr | $CH_3$ |
| 955 | 5-Cl | $CF_3$ | C≡C—Ph | $CH_3$ |
| 956 | 5-Cl | $CF_3$ | C≡C-2-Pyridyl | $CH_3$ |
| 957 | 5-Cl | $CF_3$ | C≡C-3-Pyridyl | $CH_3$ |
| 958 | 5-Cl | $CF_3$ | C≡C-4-Pyridyl | $CH_3$ |
| 959 | 5-Cl | $CF_3$ | C≡C-2-furanyl | $CH_3$ |
| 960 | 5-Cl | $CF_3$ | C≡C-3-furanyl | $CH_3$ |
| 961 | 5-Cl | $CF_3$ | C≡C-2-thienyl | $CH_3$ |
| 962 | 5-Cl | $CF_3$ | C≡C-3-thienyl | $CH_3$ |
| 963 | 5-Cl | $CF_3$ | $CH_2CH_2$-cycPr | $CH_3$ |
| 964 | 5-Cl | $CF_3$ | $CH_2CH_2$—Ph | $CH_3$ |
| 965 | 5-Cl | $CF_3$ | $CH_2CH_2$-2-Pyridyl | $CH_3$ |
| 966 | 5-Cl | $CF_3$ | $CH_2CH_2$-3-Pyridyl | $CH_3$ |
| 967 | 5-Cl | $CF_3$ | $CH_2CH_2$-4-Pyridyl | $CH_3$ |
| 968 | 5-Cl | $CF_3$ | $CH_2CH_2$-2-furanyl | $CH_3$ |
| 969 | 5-Cl | $CF_3$ | $CH_2CH_2$-3-furanyl | $CH_3$ |
| 970 | 5-Cl | $CF_3$ | $CH_2CH_2$-2-thienyl | $CH_3$ |
| 971 | 5-Cl | $CF_3$ | $CH_2CH_2$-3-thienyl | $CH_3$ |
| 972 | 5-Cl | $CF_3$ | C≡C-cycPr | $CH_2CH_3$ |
| 973 | 5-Cl | $CF_3$ | C≡C—Ph | $CH_2CH_3$ |
| 974 | 5-Cl | $CF_3$ | C≡C-2-Pyridyl | $CH_2CH_3$ |
| 975 | 5-Cl | $CF_3$ | C≡C-3-Pyridyl | $CH_2CH_3$ |
| 976 | 5-Cl | $CF_3$ | C≡C-4-Pyridyl | $CH_2CH_3$ |
| 977 | 5-Cl | $CF_3$ | C≡C-2-furanyl | $CH_2CH_3$ |
| 978 | 5-Cl | $CF_3$ | C≡C-3-furanyl | $CH_2CH_3$ |
| 979 | 5-Cl | $CF_3$ | C≡C-2-thienyl | $CH_2CH_3$ |
| 980 | 5-Cl | $CF_3$ | C≡C-3-thienyl | $CH_2CH_3$ |
| 981 | 5-Cl | $CF_3$ | C≡C-cycPr | $CH_2CH_3$ |
| 982 | 5-Cl | $CF_3$ | C≡C—Ph | $CH_2CH_3$ |
| 983 | 5-Cl | $CF_3$ | C≡C-2-Pyridyl | $CH_2CH_3$ |
| 984 | 5-Cl | $CF_3$ | C≡C-3-Pyridyl | $CH_2CH_3$ |
| 985 | 5-Cl | $CF_3$ | C≡C-4-Pyridyl | $CH_2CH_3$ |
| 986 | 5-Cl | $CF_3$ | C≡C-2-furanyl | $CH_2CH_3$ |
| 987 | 5-Cl | $CF_3$ | C≡C-3-furanyl | $CH_2CH_3$ |
| 988 | 5-Cl | $CF_3$ | C≡C-2-thienyl | $CH_2CH_3$ |
| 989 | 5-Cl | $CF_3$ | C≡C-3-thienyl | $CH_2CH_3$ |
| 990 | 5-Cl | $CF_3$ | $CH_2CH_2$-cycPr | $CH_2CH_3$ |
| 991 | 5-Cl | $CF_3$ | $CH_2CH_2$—Ph | $CH_2CH_3$ |
| 992 | 5-Cl | $CF_3$ | $CH_2CH_2$-2-Pyridyl | $CH_2CH_3$ |
| 993 | 5-Cl | $CF_3$ | $CH_2CH_2$-3-Pyridyl | $CH_2CH_3$ |
| 994 | 5-Cl | $CF_3$ | $CH_2CH_2$-4-Pyridyl | $CH_2CH_3$ |
| 995 | 5-Cl | $CF_3$ | $CH_2CH_2$-2-furanyl | $CH_2CH_3$ |
| 996 | 5-Cl | $CF_3$ | $CH_2CH_2$-3-furanyl | $CH_2CH_3$ |
| 997 | 5-Cl | $CF_3$ | $CH_2CH_2$-2-thienyl | $CH_2CH_3$ |

TABLE 2*-continued

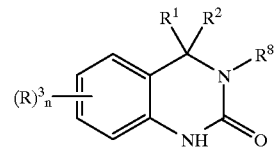

| Ex. # | R³ | R¹ | R² | R⁸ |
|---|---|---|---|---|
| 998 | 5-Cl | $CF_3$ | $CH_2CH_2$-3-thienyl | $CH_2CH_3$ |
| 999 | 5-F | $CF_3$ | C≡C-cycPr | H |
| 1000 | 5-F | $CF_3$ | C≡C$CH_2CH_2$OH | H |
| 1001 | 5-F | $CF_3$ | C≡C—CH(OH)Me | H |
| 1002 | 5-F | $CF_3$ | C≡C—Ph | H |
| 1003 | 5-F | $CF_3$ | C≡C-(2-Cl)Ph | H |
| 1004 | 5-F | $CF_3$ | C≡C-(3-Cl)Ph | H |
| 1005 | 5-F | $CF_3$ | C≡C-(4-Cl)Ph | H |
| 1006 | 5-F | $CF_3$ | C≡C-(2-F)Ph | H |
| 1007 | 5-F | $CF_3$ | C≡C-(3-F)Ph | H |
| 1008 | 5-F | $CF_3$ | C≡C-(4-F)Ph | H |
| 1009 | 5-F | $CF_3$ | C≡C-(2-OH)Ph | H |
| 1010 | 5-F | $CF_3$ | C≡C-(3-OH)Ph | H |
| 1011 | 5-F | $CF_3$ | C≡C-(4-OH)Ph | H |
| 1012 | 5-F | $CF_3$ | C≡C-(2-OMe)Ph | H |
| 1013 | 5-F | $CF_3$ | C≡C-(3-OMe)Ph | H |
| 1014 | 5-F | $CF_3$ | C≡C-(4-OMe)Ph | H |
| 1015 | 5-F | $CF_3$ | C≡C-(2-CN)Ph | H |
| 1016 | 5-F | $CF_3$ | C≡C-(3-CN)Ph | H |
| 1017 | 5-F | $CF_3$ | C≡C-(4-CN)Ph | H |
| 1018 | 5-F | $CF_3$ | C≡C-(2-$NO_2$)Ph | H |
| 1019 | 5-F | $CF_3$ | C≡C-(3-$NO_2$)Ph | H |
| 1020 | 5-F | $CF_3$ | C≡C-(4-$NO_2$)Ph | H |
| 1021 | 5-F | $CF_3$ | C≡C-(2-$NH_2$)Ph | H |
| 1022 | 5-F | $CF_3$ | C≡C-(3-$NH_2$)Ph | H |
| 1023 | 5-F | $CF_3$ | C≡C-(4-$NH_2$)Ph | H |
| 1024 | 5-F | $CF_3$ | C≡C-(2-$NMe_2$)Ph | H |
| 1025 | 5-F | $CF_3$ | C≡C-(3-$NMe_2$)Ph | H |
| 1026 | 5-F | $CF_3$ | C≡C-(4-$NMe_2$)Ph | H |
| 1027 | 5-F | $CF_3$ | C≡C-2-Pyridyl | H |
| 1028 | 5-F | $CF_3$ | C≡C-2-Pyridyl | H |
| 1029 | 5-F | $CF_3$ | C≡C-3-Pyridyl | H |
| 1030 | 5-F | $CF_3$ | C≡C-4-Pyridyl | H |
| 1031 | 5-F | $CF_3$ | C≡C-2-furanyl | H |
| 1032 | 5-F | $CF_3$ | C≡C-3-furanyl | H |
| 1033 | 5-F | $CF_3$ | C≡C-2-thienyl | H |
| 1034 | 5-F | $CF_3$ | C≡C-3-thienyl | H |
| 1035 | 5-F | $CF_3$ | C≡C-2-oxazolyl | H |
| 1036 | 5-F | $CF_3$ | C≡C-2-thiazolyl | H |
| 1037 | 5-F | $CF_3$ | C≡C-4-isoxazolyl | H |
| 1038 | 5-F | $CF_3$ | C≡C-2-imidazolyl | H |
| 1039 | 5-F | $CF_3$ | C≡C-cycPr | H |
| 1040 | 5-F | $CF_3$ | C≡C$CH_2CH_2$OH | H |
| 1041 | 5-F | $CF_3$ | C≡C—CH(OH)Me | H |
| 1042 | 5-F | $CF_3$ | C≡C—Ph | H |
| 1043 | 5-F | $CF_3$ | C≡C-(2-Cl)Ph | H |
| 1044 | 5-F | $CF_3$ | C≡C-(3-Cl)Ph | H |
| 1045 | 5-F | $CF_3$ | C≡C-(4-Cl)Ph | H |
| 1046 | 5-F | $CF_3$ | C≡C-(2-F)Ph | H |
| 1047 | 5-F | $CF_3$ | C≡C-(3-F)Ph | H |
| 1048 | 5-F | $CF_3$ | C≡C-(4-F)Ph | H |
| 1049 | 5-F | $CF_3$ | C≡C-(2-OH)Ph | H |
| 1050 | 5-F | $CF_3$ | C≡C-(3-OH)Ph | H |
| 1051 | 5-F | $CF_3$ | C≡C-(4-OH)Ph | H |
| 1052 | 5-F | $CF_3$ | C≡C-(2-OMe)Ph | H |
| 1053 | 5-F | $CF_3$ | C≡C-(3-OMe)Ph | H |
| 1054 | 5-F | $CF_3$ | C≡C-(4-OMe)Ph | H |
| 1055 | 5-F | $CF_3$ | C≡C-(2-CN)Ph | H |
| 1056 | 5-F | $CF_3$ | C≡C-(3-CN)Ph | H |
| 1057 | 5-F | $CF_3$ | C≡C-(4-CN)Ph | H |
| 1058 | 5-F | $CF_3$ | C≡C-(2-$NO_2$)Ph | H |
| 1059 | 5-F | $CF_3$ | C≡C-(3-$NO_2$)Ph | H |
| 1060 | 5-F | $CF_3$ | C≡C-(4-$NO_2$)Ph | H |
| 1061 | 5-F | $CF_3$ | C≡C-(2-$NH_2$)Ph | H |
| 1062 | 5-F | $CF_3$ | C≡C-(3-$NH_2$)Ph | H |
| 1063 | 5-F | $CF_3$ | C≡C-(4-$NH_2$)Ph | H |
| 1064 | 5-F | $CF_3$ | C≡C-(2-$NMe_2$)Ph | H |
| 1065 | 5-F | $CF_3$ | C≡C-(3-$NMe_2$)Ph | H |

TABLE 2*-continued

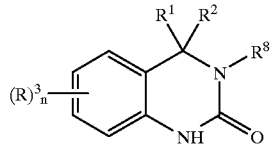

| Ex. # | R³ | R¹ | R² | R⁸ |
|---|---|---|---|---|
| 1066 | 5-F | CF₃ | C≡C-(4-NMe₂)Ph | H |
| 1067 | 5-F | CF₃ | C≡C-2-Pyridyl | H |
| 1068 | 5-F | CF₃ | C≡C-2-Pyridyl | H |
| 1069 | 5-F | CF₃ | C≡C-3-Pyridyl | H |
| 1070 | 5-F | CF₃ | C≡C-4-Pyridyl | H |
| 1071 | 5-F | CF₃ | C≡C-2-furanyl | H |
| 1072 | 5-F | CF₃ | C≡C-3-furanyl | H |
| 1073 | 5-F | CF₃ | C≡C-2-thienyl | H |
| 1074 | 5-F | CF₃ | C≡C-3-thienyl | H |
| 1075 | 5-F | CF₃ | C≡C-2-oxazolyl | H |
| 1076 | 5-F | CF₃ | C≡C-2-thiazolyl | H |
| 1077 | 5-F | CF₃ | C≡C-4-isoxazolyl | H |
| 1078 | 5-F | CF₃ | C≡C-2-imidazolyl | H |
| 1079 | 5-F | CF₃ | CH₂CH₂-cycPr | H |
| 1080 | 5-F | CF₃ | CH₂CH₂CH₂CH₂OH | H |
| 1081 | 5-F | CF₃ | CH₂CH₂—CH(OH)Me | H |
| 1082 | 5-F | CF₃ | CH₂CH₂Ph | H |
| 1083 | 5-F | CF₃ | CH₂CH₂-(2-Cl)Ph | H |
| 1084 | 5-F | CF₃ | CH₂CH₂-(3-Cl)Ph | H |
| 1085 | 5-F | CF₃ | CH₂CH₂-(4-Cl)Ph | H |
| 1086 | 5-F | CF₃ | CH₂CH₂-(2-F)Ph | H |
| 1087 | 5-F | CF₃ | CH₂CH₂-(3-F)Ph | H |
| 1088 | 5-F | CF₃ | CH₂CH₂-(4-F)Ph | H |
| 1089 | 5-F | CF₃ | CH₂CH₂-(2-OH)Ph | H |
| 1090 | 5-F | CF₃ | CH₂CH₂-(3-OH)Ph | H |
| 1091 | 5-F | CF₃ | CH₂CH₂-(4-OH)Ph | H |
| 1092 | 5-F | CF₃ | CH₂CH₂-(2-OMe)Ph | H |
| 1093 | 5-F | CF₃ | CH₂CH₂-(3-OMe)Ph | H |
| 1094 | 5-F | CF₃ | CH₂CH₂-(4-OMe)Ph | H |
| 1095 | 5-F | CF₃ | CH₂CH₂-(2-CN)Ph | H |
| 1096 | 5-F | CF₃ | CH₂CH₂-(3-CN)Ph | H |
| 1097 | 5-F | CF₃ | CH₂CH₂-(4-CN)Ph | H |
| 1098 | 5-F | CF₃ | CH₂CH₂-(2-NO₂)Ph | H |
| 1099 | 5-F | CF₃ | CH₂CH₂-(3-NO₂)Ph | H |
| 1100 | 5-F | CF₃ | CH₂CH₂-(4-NO₂)Ph | H |
| 1101 | 5-F | CF₃ | CH₂CH₂-(2-NH₂)Ph | H |
| 1102 | 5-F | CF₃ | CH₂CH₂-(3-NH₂)Ph | H |
| 1103 | 5-F | CF₃ | CH₂CH₂-(4-NH₂)Ph | H |
| 1104 | 5-F | CF₃ | CH₂CH₂-(2-NMe₂)Ph | H |
| 1105 | 5-F | CF₃ | CH₂CH₂-(3-NMe₂)Ph | H |
| 1106 | 5-F | CF₃ | CH₂CH₂-(4-NMe₂)Ph | H |
| 1107 | 5-F | CF₃ | CH₂CH₂-2-Pyridyl | H |
| 1108 | 5-F | CF₃ | CH₂CH₂-3-Pyridyl | H |
| 1109 | 5-F | CF₃ | CH₂CH₂-4-Pyridyl | H |
| 1110 | 5-F | CF₃ | CH₂CH₂-2-furanyl | H |
| 1111 | 5-F | CF₃ | CH₂CH₂-3-furanyl | H |
| 1112 | 5-F | CF₃ | CH₂CH₂-2-thienyl | H |
| 1113 | 5-F | CF₃ | CH₂CH₂-3-thienyl | H |
| 1114 | 5-F | CF₃ | CH₂CH₂-2-oxazolyl | H |
| 1115 | 5-F | CF₃ | CH₂CH₂-2-thiazolyl | H |
| 1116 | 5-F | CF₃ | CH₂CH₂-4-isoxazolyl | H |
| 1117 | 5-F | CF₃ | CH₂CH₂-2-imidazolyl | H |
| 1118 | 5-F | CF₃ | C≡C-cycPr | CH₃ |
| 1119 | 5-F | CF₃ | C≡C—Ph | CH₃ |
| 1120 | 5-F | CF₃ | C≡C-2-Pyridyl | CH₃ |
| 1121 | 5-F | CF₃ | C≡C-3-Pyridyl | CH₃ |
| 1122 | 5-F | CF₃ | C≡C-4-Pyridyl | CH₃ |
| 1123 | 5-F | CF₃ | C≡C-2-furanyl | CH₃ |
| 1124 | 5-F | CF₃ | C≡C-3-furanyl | CH₃ |
| 1125 | 5-F | CF₃ | C≡C-2-thienyl | CH₃ |
| 1126 | 5-F | CF₃ | C≡C-3-thienyl | CH₃ |
| 1127 | 5-F | CF₃ | C=C-cycPr | CH₃ |
| 1128 | 5-F | CF₃ | C=C—Ph | CH₃ |
| 1129 | 5-F | CF₃ | C=C-2-Pyridyl | CH₃ |
| 1130 | 5-F | CF₃ | C=C-3-Pyridyl | CH₃ |
| 1131 | 5-F | CF₃ | C=C-4-Pyridyl | CH₃ |
| 1132 | 5-F | CF₃ | C=C-2-furanyl | CH₃ |
| 1133 | 5-F | CF₃ | C=C-3-furanyl | CH₃ |
| 1134 | 5-F | CF₃ | C=C-2-thienyl | CH₃ |
| 1135 | 5-F | CF₃ | C=C-3-thienyl | CH₃ |
| 1136 | 5-F | CF₃ | CH₂CH₂-cycPr | CH₃ |
| 1137 | 5-F | CF₃ | CH₂CH₂—Ph | CH₃ |
| 1138 | 5-F | CF₃ | CH₂CH₂-2-Pyridyl | CH₃ |
| 1139 | 5-F | CF₃ | CH₂CH₂-3-Pyridyl | CH₃ |
| 1140 | 5-F | CF₃ | CH₂CH₂-4-Pyridyl | CH₃ |
| 1141 | 5-F | CF₃ | CH₂CH₂-2-furanyl | CH₃ |
| 1142 | 5-F | CF₃ | CH₂CH₂-3-furanyl | CH₃ |
| 1143 | 5-F | CF₃ | CH₂CH₂-2-thienyl | CH₃ |
| 1144 | 5-F | CF₃ | CH₂CH₂-3-thienyl | CH₃ |
| 1145 | 5-F | CF₃ | C≡C-cycPr | CH₂CH₃ |
| 1146 | 5-F | CF₃ | C≡C—Ph | CH₂CH₃ |
| 1147 | 5-F | CF₃ | C≡C-2-Pyridyl | CH₂CH₃ |
| 1148 | 5-F | CF₃ | C≡C-3-Pyridyl | CH₂CH₃ |
| 1149 | 5-F | CF₃ | C≡C-4-Pyridyl | CH₂CH₃ |
| 1150 | 5-F | CF₃ | C≡C-2-furanyl | CH₂CH₃ |
| 1151 | 5-F | CF₃ | C≡C-3-furanyl | CH₂CH₃ |
| 1152 | 5-F | CF₃ | C≡C-2-thienyl | CH₂CH₃ |
| 1153 | 5-F | CF₃ | C≡C-3-thienyl | CH₂CH₃ |
| 1154 | 5-F | CF₃ | C=C-cycPr | CH₂CH₃ |
| 1155 | 5-F | CF₃ | C=C—Ph | CH₂CH₃ |
| 1156 | 5-F | CF₃ | C=C-2-Pyridyl | CH₂CH₃ |
| 1157 | 5-F | CF₃ | C=C-3-Pyridyl | CH₂CH₃ |
| 1158 | 5-F | CF₃ | C=C-4-Pyridyl | CH₂CH₃ |
| 1159 | 5-F | CF₃ | C=C-2-furanyl | CH₂CH₃ |
| 1160 | 5-F | CF₃ | C=C-3-furanyl | CH₂CH₃ |
| 1161 | 5-F | CF₃ | C=C-2-thienyl | CH₂CH₃ |
| 1162 | 5-F | CF₃ | C=C-3-thienyl | CH₂CH₃ |
| 1163 | 5-F | CF₃ | CH₂CH₂-cycPr | CH₂CH₃ |
| 1164 | 5-F | CF₃ | CH₂CH₂—Ph | CH₂CH₃ |
| 1165 | 5-F | CF₃ | CH₂CH₂-2-Pyridyl | CH₂CH₃ |
| 1166 | 5-F | CF₃ | CH₂CH₂-3-Pyridyl | CH₂CH₃ |
| 1167 | 5-F | CF₃ | CH₂CH₂-4-Pyridyl | CH₂CH₃ |
| 1168 | 5-F | CF₃ | CH₂CH₂-2-furanyl | CH₂CH₃ |
| 1169 | 5-F | CF₃ | CH₂CH₂-3-furanyl | CH₂CH₃ |
| 1170 | 5-F | CF₃ | CH₂CH₂-2-thienyl | CH₂CH₃ |
| 1171 | 5-F | CF₃ | CH₂CH₂-3-thienyl | CH₂CH₃ |
| 1172 | 5-Cl, 6-F | CF₃ | C≡C-cycPr | H |
| 1173 | 5-Cl, 6-F | CF₃ | C≡C—Ph | H |
| 1174 | 5-Cl, 6-F | CF₃ | C≡C-2-Pyridyl | H |
| 1175 | 5-Cl, 6-F | CF₃ | C≡C-3-Pyridyl | H |
| 1176 | 5-Cl, 6-F | CF₃ | C≡C-4-Pyridyl | H |
| 1177 | 5-Cl, 6-F | CF₃ | C≡C-2-furanyl | H |
| 1178 | 5-Cl, 6-F | CF₃ | C≡C-3-furanyl | H |
| 1179 | 5-Cl, 6-F | CF₃ | C≡C-2-thienyl | H |
| 1180 | 5-Cl, 6-F | CF₃ | C≡C-3-thienyl | H |
| 1181 | 5-Cl, 6-F | CF₃ | C=C-cycPr | H |
| 1182 | 5-Cl, 6-F | CF₃ | C=C—Ph | H |
| 1183 | 5-Cl, 6-F | CF₃ | C=C-2-Pyridyl | H |
| 1184 | 5-Cl, 6-F | CF₃ | C=C-3-Pyridyl | H |
| 1185 | 5-Cl, 6-F | CF₃ | C=C-4-Pyridyl | H |
| 1186 | 5-Cl, 6-F | CF₃ | C=C-2-furanyl | H |
| 1187 | 5-Cl, 6-F | CF₃ | C=C-3-furanyl | H |
| 1188 | 5-Cl, 6-F | CF₃ | C=C-2-thienyl | H |
| 1189 | 5-Cl, 6-F | CF₃ | C=C-3-thienyl | H |
| 1190 | 5-Cl, 6-F | CF₃ | CH₂CH₂-cycPr | H |
| 1191 | 5-Cl, 6-F | CF₃ | CH₂CH₂—Ph | H |
| 1192 | 5-Cl, 6-F | CF₃ | CH₂CH₂-2-Pyridyl | H |
| 1193 | 5-Cl, 6-F | CF₃ | CH₂CH₂-3-Pyridyl | H |
| 1194 | 5-Cl, 6-F | CF₃ | CH₂CH₂-4-Pyridyl | H |
| 1195 | 5-Cl, 6-F | CF₃ | CH₂CH₂-2-furanyl | H |
| 1196 | 5-Cl, 6-F | CF₃ | CH₂CH₂-3-furanyl | H |
| 1197 | 5-Cl, 6-F | CF₃ | CH₂CH₂-2-thienyl | H |
| 1198 | 5-Cl, 6-F | CF₃ | CH₂CH₂-3-thienyl | H |
| 1199 | 5-Cl, 6-F | CF₃ | C≡C-cycPr | CH₃ |
| 1200 | 5-Cl, 6-F | CF₃ | C≡C—Ph | CH₃ |
| 1201 | 5-Cl, 6-F | CF₃ | C≡C-2-Pyridyl | CH₃ |

TABLE 2*-continued

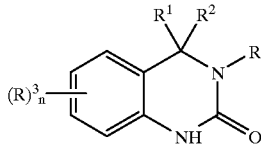

| Ex. # | R³ | R¹ | R² | R⁸ |
|---|---|---|---|---|
| 1202 | 5-Cl, 6-F | CF₃ | C≡C-3-Pyridyl | CH₃ |
| 1203 | 5-Cl, 6-F | CF₃ | C≡C-4-Pyridyl | CH₃ |
| 1204 | 5-Cl, 6-F | CF₃ | C≡C-2-furanyl | CH₃ |
| 1205 | 5-Cl, 6-F | CF₃ | C≡C-3-furanyl | CH₃ |
| 1206 | 5-Cl, 6-F | CF₃ | C≡C-2-thienyl | CH₃ |
| 1207 | 5-Cl, 6-F | CF₃ | C≡C-3-thienyl | CH₃ |
| 1208 | 5-Cl, 6-F | CF₃ | C=C-cycPr | CH₃ |
| 1209 | 5-Cl, 6-F | CF₃ | C=C—Ph | CH₃ |
| 1210 | 5-Cl, 6-F | CF₃ | C=C-2-Pyridyl | CH₃ |
| 1211 | 5-Cl, 6-F | CF₃ | C=C-3-Pyridyl | CH₃ |
| 1212 | 5-Cl, 6-F | CF₃ | C=C-4-Pyridyl | CH₃ |
| 1213 | 5-Cl, 6-F | CF₃ | C=C-2-furanyl | CH₃ |
| 1214 | 5-Cl, 6-F | CF₃ | C=C-3-furanyl | CH₃ |
| 1215 | 5-Cl, 6-F | CF₃ | C=C-2-thienyl | CH₃ |
| 1216 | 5-Cl, 6-F | CF₃ | C=C-3-thienyl | CH₃ |
| 1217 | 5-Cl, 6-F | CF₃ | CH₂CH₂-cycPr | CH₃ |
| 1218 | 5-Cl, 6-F | CF₃ | CH₂CH₂—Ph | CH₃ |
| 1219 | 5-Cl, 6-F | CF₃ | CH₂CH₂-2-Pyridyl | CH₃ |
| 1220 | 5-Cl, 6-F | CF₃ | CH₂CH₂-3-Pyridyl | CH₃ |
| 1221 | 5-Cl, 6-F | CF₃ | CH₂CH₂-4-Pyridyl | CH₃ |
| 1222 | 5-Cl, 6-F | CF₃ | CH₂CH₂-2-furanyl | CH₃ |
| 1223 | 5-Cl, 6-F | CF₃ | CH₂CH₂-3-furanyl | CH₃ |
| 1224 | 5-Cl, 6-F | CF₃ | CH₂CH₂-2-thienyl | CH₃ |
| 1225 | 5-Cl, 6-F | CF₃ | CH₂CH₂-3-thienyl | CH₃ |
| 1226 | 5-F, 6-Cl | CF₃ | C≡C-cycPr | H |
| 1227 | 5-F, 6-Cl | CF₃ | C≡C—Ph | H |
| 1228 | 5-F, 6-Cl | CF₃ | C≡C-2-Pyridyl | H |
| 1229 | 5-F, 6-Cl | CF₃ | C≡C-3-Pyridyl | H |
| 1230 | 5-F, 6-Cl | CF₃ | C≡C-4-Pyridyl | H |
| 1231 | 5-F, 6-Cl | CF₃ | C≡C-2-furanyl | H |
| 1232 | 5-F, 6-Cl | CF₃ | C≡C-3-furanyl | H |
| 1233 | 5-F, 6-Cl | CF₃ | C≡C-2-thienyl | H |
| 1234 | 5-F, 6-Cl | CF₃ | C≡C-3-thienyl | H |
| 1235 | 5-F, 6-Cl | CF₃ | C=C-cycPr | H |
| 1236 | 5-F, 6-Cl | CF₃ | C=C—Ph | H |
| 1237 | 5-F, 6-Cl | CF₃ | C=C-2-Pyridyl | H |
| 1238 | 5-F, 6-Cl | CF₃ | C=C-3-Pyridyl | H |
| 1239 | 5-F, 6-Cl | CF₃ | C=C-4-Pyridyl | H |
| 1240 | 5-F, 6-Cl | CF₃ | C=C-2-furanyl | H |
| 1241 | 5-F, 6-Cl | CF₃ | C=C-3-furanyl | H |
| 1242 | 5-F, 6-Cl | CF₃ | C=C-2-thienyl | H |
| 1243 | 5-F, 6-Cl | CF₃ | C=C-3-thienyl | H |
| 1244 | 5-F, 6-Cl | CF₃ | CH₂CH₂-cycPr | H |
| 1245 | 5-F, 6-Cl | CF₃ | CH₂CH₂—Ph | H |
| 1246 | 5-F, 6-Cl | CF₃ | CH₂CH₂-2-Pyridyl | H |
| 1247 | 5-F, 6-Cl | CF₃ | CH₂CH₂-3-Pyridyl | H |
| 1248 | 5-F, 6-Cl | CF₃ | CH₂CH₂-4-Pyridyl | H |
| 1249 | 5-F, 6-Cl | CF₃ | CH₂CH₂-2-furanyl | H |
| 1250 | 5-F, 6-Cl | CF₃ | CH₂CH₂-3-furanyl | H |
| 1251 | 5-F, 6-Cl | CF₃ | CH₂CH₂-2-thienyl | H |
| 1252 | 5-F, 6-Cl | CF₃ | CH₂CH₂-3-thienyl | H |
| 1253 | 5-F, 6-Cl | CF₃ | C≡C-cycPr | CH₃ |
| 1254 | 5-F, 6-Cl | CF₃ | C≡C—Ph | CH₃ |
| 1255 | 5-F, 6-Cl | CF₃ | C≡C-2-Pyridyl | CH₃ |
| 1256 | 5-F, 6-Cl | CF₃ | C≡C-3-Pyridyl | CH₃ |
| 1257 | 5-F, 6-Cl | CF₃ | C≡C-4-Pyridyl | CH₃ |
| 1258 | 5-F, 6-Cl | CF₃ | C≡C-2-furanyl | CH₃ |
| 1259 | 5-F, 6-Cl | CF₃ | C≡C-3-furanyl | CH₃ |
| 1260 | 5-F, 6-Cl | CF₃ | C≡C-2-thienyl | CH₃ |
| 1261 | 5-F, 6-Cl | CF₃ | C≡C-3-thienyl | CH₃ |
| 1262 | 5-F, 6-Cl | CF₃ | C=C-cycPr | CH₃ |
| 1263 | 5-F, 6-Cl | CF₃ | C=C—Ph | CH₃ |
| 1264 | 5-F, 6-Cl | CF₃ | C=C-2-Pyridyl | CH₃ |
| 1265 | 5-F, 6-Cl | CF₃ | C=C-3-Pyridyl | CH₃ |
| 1266 | 5-F, 6-Cl | CF₃ | C=C-4-Pyridyl | CH₃ |
| 1267 | 5-F, 6-Cl | CF₃ | C=C-2-furanyl | CH₃ |
| 1268 | 5-F, 6-Cl | CF₃ | C=C-3-furanyl | CH₃ |
| 1269 | 5-F, 6-Cl | CF₃ | C=C-2-thienyl | CH₃ |

TABLE 2*-continued

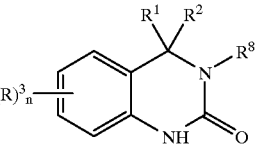

| Ex. # | R³ | R¹ | R² | R⁸ |
|---|---|---|---|---|
| 1270 | 5-F, 6-Cl | CF₃ | C=C-3-thienyl | CH₃ |
| 1271 | 5-F, 6-Cl | CF₃ | CH₂CH₂-cycPr | CH₃ |
| 1272 | 5-F, 6-Cl | CF₃ | CH₂CH₂—Ph | CH₃ |
| 1273 | 5-F, 6-Cl | CF₃ | CH₂CH₂-2-Pyridyl | CH₃ |
| 1274 | 5-F, 6-Cl | CF₃ | CH₂CH₂-3-Pyridyl | CH₃ |
| 1275 | 5-F, 6-Cl | CF₃ | CH₂CH₂-4-Pyridyl | CH₃ |
| 1276 | 5-F, 6-Cl | CF₃ | CH₂CH₂-2-furanyl | CH₃ |
| 1277 | 5-F, 6-Cl | CF₃ | CH₂CH₂-3-furanyl | CH₃ |
| 1278 | 5-F, 6-Cl | CF₃ | CH₂CH₂-2-thienyl | CH₃ |
| 1279 | 5-F, 6-Cl | CF₃ | CH₂CH₂-3-thienyl | CH₃ |
| 1280 | 6-Cl, 8-F | CF₃ | C≡C-cycPr | H |
| 1281 | 6-Cl, 8-F | CF₃ | C≡C—Ph | H |
| 1282 | 6-Cl, 8-F | CF₃ | C≡C-2-Pyridyl | H |
| 1283 | 6-Cl, 8-F | CF₃ | C≡C-3-Pyridyl | H |
| 1284 | 6-Cl, 8-F | CF₃ | C≡C-4-Pyridyl | H |
| 1285 | 6-Cl, 8-F | CF₃ | C≡C-2-furanyl | H |
| 1286 | 6-Cl, 8-F | CF₃ | C≡C-3-furanyl | H |
| 1287 | 6-Cl, 8-F | CF₃ | C≡C-2-thienyl | H |
| 1288 | 6-Cl, 8-F | CF₃ | C≡C-3-thienyl | H |
| 1289 | 6-Cl, 8-F | CF₃ | C=C-cycPr | H |
| 1290 | 6-Cl, 8-F | CF₃ | C=C—Ph | H |
| 1291 | 6-Cl, 8-F | CF₃ | C=C-2-Pyridyl | H |
| 1292 | 6-Cl, 8-F | CF₃ | C=C-3-Pyridyl | H |
| 1293 | 6-Cl, 8-F | CF₃ | C=C-4-Pyridyl | H |
| 1294 | 6-Cl, 8-F | CF₃ | C=C-2-furanyl | H |
| 1295 | 6-Cl, 8-F | CF₃ | C=C-3-furanyl | H |
| 1296 | 6-Cl, 8-F | CF₃ | C=C-2-thienyl | H |
| 1297 | 6-Cl, 8-F | CF₃ | C=C-3-thienyl | H |
| 1298 | 6-Cl, 8-F | CF₃ | CH₂CH₂-cycPr | H |
| 1299 | 6-Cl, 8-F | CF₃ | CH₂CH₂—Ph | H |
| 1300 | 6-Cl, 8-F | CF₃ | CH₂CH₂-2-Pyridyl | H |
| 1301 | 6-Cl, 8-F | CF₃ | CH₂CH₂-3-Pyridyl | H |
| 1302 | 6-Cl, 8-F | CF₃ | CH₂CH₂-4-Pyridyl | H |
| 1303 | 6-Cl, 8-F | CF₃ | CH₂CH₂-2-furanyl | H |
| 1304 | 6-Cl, 8-F | CF₃ | CH₂CH₂-3-furanyl | H |
| 1305 | 6-Cl, 8-F | CF₃ | CH₂CH₂-2-thienyl | H |
| 1306 | 6-Cl, 8-F | CF₃ | CH₂CH₂-3-thienyl | H |
| 1307 | 6-Cl, 8-F | CF₃ | C≡C-cycPr | CH₃ |
| 1308 | 6-Cl, 8-F | CF₃ | C≡C—Ph | CH₃ |
| 1309 | 6-Cl, 8-F | CF₃ | C≡C-2-Pyridyl | CH₃ |
| 1310 | 6-Cl, 8-F | CF₃ | C≡C-3-Pyridyl | CH₃ |
| 1311 | 6-Cl, 8-F | CF₃ | C≡C-4-Pyridyl | CH₃ |
| 1312 | 6-Cl, 8-F | CF₃ | C≡C-2-furanyl | CH₃ |
| 1313 | 6-Cl, 8-F | CF₃ | C≡C-3-furanyl | CH₃ |
| 1314 | 6-Cl, 8-F | CF₃ | C≡C-2-thienyl | CH₃ |
| 1315 | 6-Cl, 8-F | CF₃ | C≡C-3-thienyl | CH₃ |
| 1316 | 6-Cl, 8-F | CF₃ | C=C-cycPr | CH₃ |
| 1317 | 6-Cl, 8-F | CF₃ | C=C—Ph | CH₃ |
| 1318 | 6-Cl, 8-F | CF₃ | C=C-2-Pyridyl | CH₃ |
| 1319 | 6-Cl, 8-F | CF₃ | C=C-3-Pyridyl | CH₃ |
| 1320 | 6-Cl, 8-F | CF₃ | C=C-4-Pyridyl | CH₃ |
| 1321 | 6-Cl, 8-F | CF₃ | C=C-2-furanyl | CH₃ |
| 1322 | 6-Cl, 8-F | CF₃ | C=C-3-furanyl | CH₃ |
| 1323 | 6-Cl, 8-F | CF₃ | C=C-2-thienyl | CH₃ |
| 1324 | 6-Cl, 8-F | CF₃ | C=C-3-thienyl | CH₃ |
| 1325 | 6-Cl, 8-F | CF₃ | CH₂CH₂-cycPr | CH₃ |
| 1326 | 6-Cl, 8-F | CF₃ | CH₂CH₂—Ph | CH₃ |
| 1327 | 6-Cl, 8-F | CF₃ | CH₂CH₂-2-Pyridyl | CH₃ |
| 1328 | 6-Cl, 8-F | CF₃ | CH₂CH₂-3-Pyridyl | CH₃ |
| 1329 | 6-Cl, 8-F | CF₃ | CH₂CH₂-4-Pyridyl | CH₃ |
| 1330 | 6-Cl, 8-F | CF₃ | CH₂CH₂-2-furanyl | CH₃ |
| 1331 | 6-Cl, 8-F | CF₃ | CH₂CH₂-3-furanyl | CH₃ |
| 1332 | 6-Cl, 8-F | CF₃ | CH₂CH₂-2-thienyl | CH₃ |
| 1333 | 6-Cl, 8-F | CF₃ | CH₂CH₂-3-thienyl | CH₃ |
| 1334 | 6-CH₃ | CF₃ | C≡C-cycPr | H |
| 1335 | 6-CH₃ | CF₃ | C≡C—Ph | H |
| 1336 | 6-CH₃ | CF₃ | C≡C-2-Pyridyl | H |
| 1337 | 6-CH₃ | CF₃ | C≡C-3-Pyridyl | H |

TABLE 2*-continued

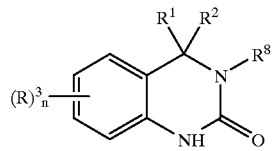

| Ex. # | R³ | R¹ | R² | R⁸ |
|---|---|---|---|---|
| 1338 | 6-CH₃ | CF₃ | C≡C-4-Pyridyl | H |
| 1339 | 6-CH₃ | CF₃ | C≡C-2-furanyl | H |
| 1340 | 6-CH₃ | CF₃ | C≡C-3-furanyl | H |
| 1341 | 6-CH₃ | CF₃ | C≡C-2-thienyl | H |
| 1342 | 6-CH₃ | CF₃ | C≡C-3-thienyl | H |
| 1343 | 6-CH₃ | CF₃ | C≡C-cycPr | H |
| 1344 | 6-CH₃ | CF₃ | C≡C—Ph | H |
| 1345 | 6-CH₃ | CF₃ | C≡C-2-Pyridyl | H |
| 1346 | 6-CH₃ | CF₃ | C≡C-3-Pyridyl | H |
| 1347 | 6-CH₃ | CF₃ | C≡C-4-Pyridyl | H |
| 1348 | 6-CH₃ | CF₃ | C≡C-2-furanyl | H |
| 1349 | 6-CH₃ | CF₃ | C≡C-3-furanyl | H |
| 1350 | 6-CH₃ | CF₃ | C≡C-2-thienyl | H |
| 1351 | 6-CH₃ | CF₃ | C≡C-3-thienyl | H |
| 1352 | 6-CH₃ | CF₃ | CH₂CH₂-cycPr | H |
| 1353 | 6-CH₃ | CF₃ | CH₂CH₂—Ph | H |
| 1354 | 6-CH₃ | CF₃ | CH₂CH₂-2-Pyridyl | H |
| 1355 | 6-CH₃ | CF₃ | CH₂CH₂-3-Pyridyl | H |
| 1356 | 6-CH₃ | CF₃ | CH₂CH₂-4-Pyridyl | H |
| 1357 | 6-CH₃ | CF₃ | CH₂CH₂-2-furanyl | H |
| 1358 | 6-CH₃ | CF₃ | CH₂CH₂-3-furanyl | H |
| 1359 | 6-CH₃ | CF₃ | CH₂CH₂-2-thienyl | H |
| 1360 | 6-CH₃ | CF₃ | CH₂CH₂-3-thienyl | H |
| 1361 | 6-CH₃ | CF₃ | C≡C-cycPr | CH₃ |
| 1362 | 6-CH₃ | CF₃ | C≡C—Ph | CH₃ |
| 1363 | 6-CH₃ | CF₃ | C≡C-2-Pyridyl | CH₃ |
| 1364 | 6-CH₃ | CF₃ | C≡C-3-Pyridyl | CH₃ |
| 1365 | 6-CH₃ | CF₃ | C≡C-4-Pyridyl | CH₃ |
| 1366 | 6-CH₃ | CF₃ | C≡C-2-furanyl | CH₃ |
| 1367 | 6-CH₃ | CF₃ | C≡C-3-furanyl | CH₃ |
| 1368 | 6-CH₃ | CF₃ | C≡C-2-thienyl | CH₃ |
| 1369 | 6-CH₃ | CF₃ | C≡C-3-thienyl | CH₃ |
| 1370 | 6-CH₃ | CF₃ | C≡C-cycPr | CH₃ |
| 1371 | 6-CH₃ | CF₃ | C≡C—Ph | CH₃ |
| 1372 | 6-CH₃ | CF₃ | C≡C-2-Pyridyl | CH₃ |
| 1373 | 6-CH₃ | CF₃ | C≡C-3-Pyridyl | CH₃ |
| 1374 | 6-CH₃ | CF₃ | C≡C-4-Pyridyl | CH₃ |
| 1375 | 6-CH₃ | CF₃ | C≡C-2-furanyl | CH₃ |
| 1376 | 6-CH₃ | CF₃ | C≡C-3-furanyl | CH₃ |
| 1377 | 6-CH₃ | CF₃ | C≡C-2-thienyl | CH₃ |
| 1378 | 6-CH₃ | CF₃ | C≡C-3-thienyl | CH₃ |
| 1379 | 6-CH₃ | CF₃ | CH₂CH₂-cycPr | CH₃ |
| 1380 | 6-CH₃ | CF₃ | CH₂CH₂—Ph | CH₃ |
| 1381 | 6-CH₃ | CF₃ | CH₂CH₂-2-Pyridyl | CH₃ |
| 1382 | 6-CH₃ | CF₃ | CH₂CH₂-3-Pyridyl | CH₃ |
| 1383 | 6-CH₃ | CF₃ | CH₂CH₂-4-Pyridyl | CH₃ |
| 1384 | 6-CH₃ | CF₃ | CH₂CH₂-2-furanyl | CH₃ |
| 1385 | 6-CH₃ | CF₃ | CH₂CH₂-3-furanyl | CH₃ |
| 1386 | 6-CH₃ | CF₃ | CH₂CH₂-2-thienyl | CH₃ |
| 1387 | 6-CH₃ | CF₃ | CH₂CH₂-3-thienyl | CH₃ |
| 1388 | 6-COCH₃ | CF₃ | C≡C-cycPr | H |
| 1389 | 6-COCH₃ | CF₃ | C≡C—Ph | H |
| 1390 | 6-COCH₃ | CF₃ | C≡C-2-Pyridyl | H |
| 1391 | 6-COCH₃ | CF₃ | C≡C-3-Pyridyl | H |
| 1392 | 6-COCH₃ | CF₃ | C≡C-4-Pyridyl | H |
| 1393 | 6-COCH₃ | CF₃ | C≡C-2-furanyl | H |
| 1394 | 6-COCH₃ | CF₃ | C≡C-3-furanyl | H |
| 1395 | 6-COCH₃ | CF₃ | C≡C-2-thienyl | H |
| 1396 | 6-COCH₃ | CF₃ | C≡C-3-thienyl | H |
| 1397 | 6-NH₂ | CF₃ | C≡C-cycPr | H |
| 1398 | 6-NH₂ | CF₃ | C≡C—Ph | H |
| 1399 | 6-NH₂ | CF₃ | C≡C-2-Pyridyl | H |
| 1400 | 6-NH₂ | CF₃ | C≡C-3-Pyridyl | H |
| 1401 | 6-NH₂ | CF₃ | C≡C-4-Pyridyl | H |
| 1402 | 6-NH₂ | CF₃ | C≡C-2-furanyl | H |
| 1403 | 6-NH₂ | CF₃ | C≡C-3-furanyl | H |
| 1404 | 6-NH₂ | CF₃ | C≡C-2-thienyl | H |
| 1405 | 6-NH₂ | CF₃ | C≡C-3-thienyl | H |

TABLE 2*-continued

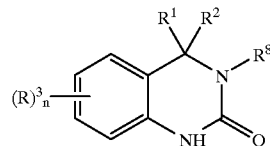

| Ex. # | R³ | R¹ | R² | R⁸ |
|---|---|---|---|---|
| 1406 | 6-NMe₂ | CF₃ | C≡C-cycPr | H |
| 1407 | 6-NMe₂ | CF₃ | C≡C—Ph | H |
| 1408 | 6-NMe₂ | CF₃ | C≡C-2-Pyridyl | H |
| 1409 | 6-NMe₂ | CF₃ | C≡C-3-Pyridyl | H |
| 1410 | 6-NMe₂ | CF₃ | C≡C-4-Pyridyl | H |
| 1411 | 6-NMe₂ | CF₃ | C≡C-2-furanyl | H |
| 1412 | 6-NMe₂ | CF₃ | C≡C-3-furanyl | H |
| 1413 | 6-NMe₂ | CF₃ | C≡C-2-thienyl | H |
| 1414 | 6-NMe₂ | CF₃ | C≡C-3-thienyl | H |
| 1415 | 7-Cl | CF₃ | C≡C-cycPr | H |
| 1416 | 7-Cl | CF₃ | C≡C—Ph | H |
| 1417 | 7-Cl | CF₃ | C≡C-2-Pyridyl | H |
| 1418 | 7-Cl | CF₃ | C≡C-3-Pyridyl | H |
| 1419 | 7-Cl | CF₃ | C≡C-4-Pyridyl | H |
| 1420 | 7-Cl | CF₃ | C≡C-2-furanyl | H |
| 1421 | 7-Cl | CF₃ | C≡C-3-furanyl | H |
| 1422 | 7-Cl | CF₃ | C≡C-2-thienyl | H |
| 1423 | 7-Cl | CF₃ | C≡C-3-thienyl | H |
| 1424 | 5,6-OCH₂O— | CF₃ | C≡C-cycPr | H |
| 1425 | 5,6-OCH₂O— | CF₃ | C≡CCH₂CH₂OH | H |
| 1426 | 5,6-OCH₂O— | CF₃ | C≡C—CH(OH)Me | H |
| 1427 | 5,6-OCH₂O— | CF₃ | C≡C—Ph | H |
| 1428 | 5,6-OCH₂O— | CF₃ | C≡C-(2-Cl)Ph | H |
| 1429 | 5,6-OCH₂O— | CF₃ | C≡C-(3-Cl)Ph | H |
| 1430 | 5,6-OCH₂O— | CF₃ | C≡C-(4-Cl)Ph | H |
| 1431 | 5,6-OCH₂O— | CF₃ | C≡C-(2-F)Ph | H |
| 1432 | 5,6-OCH₂O— | CF₃ | C≡C-(3-F)Ph | H |
| 1433 | 5,6-OCH₂O— | CF₃ | C≡C-(4-F)Ph | H |
| 1434 | 5,6-OCH₂O— | CF₃ | C≡C-(2-OH)Ph | H |
| 1435 | 5,6-OCH₂O— | CF₃ | C≡C-(3-OH)Ph | H |
| 1436 | 5,6-OCH₂O— | CF₃ | C≡C-(4-OH)Ph | H |
| 1437 | 5,6-OCH₂O— | CF₃ | C≡C-(2-OMe)Ph | H |
| 1438 | 5,6-OCH₂O— | CF₃ | C≡C-(3-OMe)Ph | H |
| 1439 | 5,6-OCH₂O— | CF₃ | C≡C-(4-OMe)Ph | H |
| 1440 | 5,6-OCH₂O— | CF₃ | C≡C-(2-CN)Ph | H |
| 1441 | 5,6-OCH₂O— | CF₃ | C≡C-(3-CN)Ph | H |
| 1442 | 5,6-OCH₂O— | CF₃ | C≡C-(4-CN)Ph | H |
| 1443 | 5,6-OCH₂O— | CF₃ | C≡C-(2-NO₂)Ph | H |
| 1444 | 5,6-OCH₂O— | CF₃ | C≡C-(3-NO₂)Ph | H |
| 1445 | 5,6-OCH₂O— | CF₃ | C≡C-(4-NO₂)Ph | H |
| 1446 | 5,6-OCH₂O— | CF₃ | C≡C-(2-NH₂)Ph | H |
| 1447 | 5,6-OCH₂O— | CF₃ | C≡C-(3-NH₂)Ph | H |
| 1448 | 5,6-OCH₂O— | CF₃ | C≡C-(4-NH₂)Ph | H |
| 1449 | 5,6-OCH₂O— | CF₃ | C≡C-(2-NMe₂)Ph | H |
| 1450 | 5,6-OCH₂O— | CF₃ | C≡C-(3-NMe₂)Ph | H |
| 1451 | 5,6-OCH₂O— | CF₃ | C≡C-(4-NMe₂)Ph | H |
| 1452 | 5,6-OCH₂O— | CF₃ | C≡C-2-Pyridyl | H |
| 1453 | 5,6-OCH₂O— | CF₃ | C≡C-2-Pyridyl | H |
| 1454 | 5,6-OCH₂O— | CF₃ | C≡C-3-Pyridyl | H |
| 1455 | 5,6-OCH₂O— | CF₃ | C≡C-4-Pyridyl | H |
| 1456 | 5,6-OCH₂O— | CF₃ | C≡C-2-furanyl | H |
| 1457 | 5,6-OCH₂O— | CF₃ | C≡C-3-furanyl | H |
| 1458 | 5,6-OCH₂O— | CF₃ | C≡C-2-thienyl | H |
| 1459 | 5,6-OCH₂O— | CF₃ | C≡C-3-thienyl | H |
| 1460 | 5,6-OCH₂O— | CF₃ | C≡C-2-oxazolyl | H |
| 1461 | 5,6-OCH₂O— | CF₃ | C≡C-2-thiazolyl | H |
| 1462 | 5,6-OCH₂O— | CF₃ | C≡C-4-isoxazolyl | H |
| 1463 | 5,6-OCH₂O— | CF₃ | C≡C-2-imidazolyl | H |
| 1464 | 6-COCH₃ | CF₃ | C≡C-cycPr | H |
| 1465 | 6-COCH₃ | CF₃ | C≡C—Ph | H |
| 1466 | 6-COCH₃ | CF₃ | C≡C-2-Pyridyl | H |
| 1467 | 6-COCH₃ | CF₃ | C≡C-3-Pyridyl | H |
| 1468 | 6-COCH₃ | CF₃ | C≡C-4-Pyridyl | H |
| 1469 | 6-COCH₃ | CF₃ | C≡C-2-furanyl | H |
| 1470 | 6-COCH₃ | CF₃ | C≡C-3-furanyl | H |
| 1471 | 6-COCH₃ | CF₃ | C≡C-2-thienyl | H |
| 1472 | 6-COCH₃ | CF₃ | C≡C-3-thienyl | H |
| 1473 | 6-NH₂ | CF₃ | C≡C-cycPr | H |

TABLE 2*-continued

| Ex. # | R³ | R¹ | R² | R⁸ |
|---|---|---|---|---|
| 1474 | 6-NH₂ | CF₃ | C≡C—Ph | H |
| 1475 | 6-NH₂ | CF₃ | C≡C-2-Pyridyl | H |
| 1476 | 6-NH₂ | CF₃ | C≡C-3-Pyridyl | H |
| 1477 | 6-NH₂ | CF₃ | C≡C-4-Pyridyl | H |
| 1478 | 6-NH₂ | CF₃ | C≡C-2-furanyl | H |
| 1479 | 6-NH₂ | CF₃ | C≡C-3-furanyl | H |
| 1480 | 6-NH₂ | CF₃ | C≡C-2-thienyl | H |
| 1481 | 6-NH₂ | CF₃ | C≡C-3-thienyl | H |
| 1482 | 6-NMe₂ | CF₃ | C≡C-cycPr | H |
| 1483 | 6-NMe₂ | CF₃ | C≡C—Ph | H |
| 1484 | 6-NMe₂ | CF₃ | C≡C-2-Pyridyl | H |
| 1485 | 6-NMe₂ | CF₃ | C≡C-3-Pyridyl | H |
| 1486 | 6-NMe₂ | CF₃ | C≡C-4-Pyridyl | H |
| 1487 | 6-NMe₂ | CF₃ | C≡C-2-furanyl | H |
| 1488 | 6-NMe₂ | CF₃ | C≡C-3-furanyl | H |
| 1489 | 6-NMe₂ | CF₃ | C≡C-2-thienyl | H |
| 1490 | 6-NMe₂ | CF₃ | C≡C-3-thienyl | H |
| 1491 | 7-Cl | CF₃ | C≡C-cycPr | H |
| 1492 | 7-Cl | CF₃ | C≡C—Ph | H |
| 1493 | 7-Cl | CF₃ | C≡C-2-Pyridyl | H |
| 1494 | 7-Cl | CF₃ | C≡C-3-Pyridyl | H |
| 1495 | 7-Cl | CF₃ | C≡C-4-Pyridyl | H |
| 1496 | 7-Cl | CF₃ | C≡C-2-furanyl | H |
| 1497 | 7-Cl | CF₃ | C≡C-3-furanyl | H |
| 1498 | 7-Cl | CF₃ | C≡C-2-thienyl | H |
| 1499 | 7-Cl | CF₃ | C≡C-3-thienyl | H |
| 1500 | 5,6-OCH₂O— | CF₃ | C≡C-cycPr | H |
| 1501 | 5,6-OCH₂O— | CF₃ | C≡CCH₂CH₂OH | H |
| 1502 | 5,6-OCH₂O— | CF₃ | C≡C—CH(OH)Me | H |
| 1503 | 5,6-OCH₂O— | CF₃ | C≡C—Ph | H |
| 1504 | 5,6-OCH₂O— | CF₃ | C≡C-(2-Cl)Ph | H |
| 1505 | 5,6-OCH₂O— | CF₃ | C≡C-(3-Cl)Ph | H |
| 1506 | 5,6-OCH₂O— | CF₃ | C≡C-(4-Cl)Ph | H |
| 1507 | 5,6-OCH₂O— | CF₃ | C≡C-(2-F)Ph | H |
| 1508 | 5,6-OCH₂O— | CF₃ | C≡C-(3-F)Ph | H |
| 1509 | 5,6-OCH₂O— | CF₃ | C≡C-(4-F)Ph | H |
| 1510 | 5,6-OCH₂O— | CF₃ | C≡C-(2-OH)Ph | H |
| 1511 | 5,6-OCH₂O— | CF₃ | C≡C-(3-OH)Ph | H |
| 1512 | 5,6-OCH₂O— | CF₃ | C≡C-(4-OH)Ph | H |
| 1513 | 5,6-OCH₂O— | CF₃ | C≡C-(2-OMe)Ph | H |
| 1514 | 5,6-OCH₂O— | CF₃ | C≡C-(3-OMe)Ph | H |
| 1515 | 5,6-OCH₂O— | CF₃ | C≡C-(4-OMe)Ph | H |
| 1516 | 5,6-OCH₂O— | CF₃ | C≡C-(2-CN)Ph | H |
| 1517 | 5,6-OCH₂O— | CF₃ | C≡C-(3-CN)Ph | H |
| 1518 | 5,6-OCH₂O— | CF₃ | C≡C-(4-CN)Ph | H |
| 1519 | 5,6-OCH₂O— | CF₃ | C≡C-(2-NO₂)Ph | H |
| 1520 | 5,6-OCH₂O— | CF₃ | C≡C-(3-NO₂)Ph | H |
| 1521 | 5,6-OCH₂O— | CF₃ | C≡C-(4-NO₂)Ph | H |
| 1522 | 5,6-OCH₂O— | CF₃ | C≡C-(2-NH₂)Ph | H |
| 1523 | 5,6-OCH₂O— | CF₃ | C≡C-(3-NH₂)Ph | H |
| 1524 | 5,6-OCH₂O— | CF₃ | C≡C-(4-NH₂)Ph | H |
| 1525 | 5,6-OCH₂O— | CF₃ | C≡C-(2-NMe₂)Ph | H |
| 1526 | 5,6-OCH₂O— | CF₃ | C≡C-(3-NMe₂)Ph | H |
| 1527 | 5,6-OCH₂O— | CF₃ | C≡C-(4-NMe₂)Ph | H |
| 1528 | 5,6-OCH₂O— | CF₃ | C≡C-2-Pyridyl | H |
| 1529 | 5,6-OCH₂O— | CF₃ | C≡C-2-Pyridyl | H |
| 1530 | 5,6-OCH₂O— | CF₃ | C≡C-3-Pyridyl | H |
| 1531 | 5,6-OCH₂O— | CF₃ | C≡C-4-Pyridyl | H |
| 1532 | 5,6-OCH₂O— | CF₃ | C≡C-2-furanyl | H |
| 1533 | 5,6-OCH₂O— | CF₃ | C≡C-3-furanyl | H |
| 1534 | 5,6-OCH₂O— | CF₃ | C≡C-2-thienyl | H |
| 1535 | 5,6-OCH₂O— | CF₃ | C≡C-3-thienyl | H |
| 1536 | 5,6-OCH₂O— | CF₃ | C≡C-2-oxazolyl | H |
| 1537 | 5,6-OCH₂O— | CF₃ | C≡C-2-thiazolyl | H |
| 1538 | 5,6-OCH₂O— | CF₃ | C≡C-4-isoxazolyl | H |
| 1539 | 5,6-OCH₂O— | CF₃ | C≡C-2-imidazolyl | H |
| 1540 | 5,6-OCH₂O— | CF₃ | CH₂CH₂-cycPr | H |
| 1541 | 5,6-OCH₂O— | CF₃ | CH₂CH₂CH₂CH₂OH | H |
| 1542 | 5,6-OCH₂O— | CF₃ | CH₂CH₂—CH(OH)Me | H |
| 1543 | 5,6-OCH₂O— | CF₃ | CH₂CH₂Ph | H |
| 1544 | 5,6-OCH₂O— | CF₃ | CH₂CH₂-(2-Cl)Ph | H |
| 1545 | 5,6-OCH₂O— | CF₃ | CH₂CH₂-(3-Cl)Ph | H |
| 1546 | 5,6-OCH₂O— | CF₃ | CH₂CH₂-(4-Cl)Ph | H |
| 1547 | 5,6-OCH₂O— | CF₃ | CH₂CH₂-(2-F)Ph | H |
| 1548 | 5,6-OCH₂O— | CF₃ | CH₂CH₂-(3-F)Ph | H |
| 1549 | 5,6-OCH₂O— | CF₃ | CH₂CH₂-(4-F)Ph | H |
| 1550 | 5,6-OCH₂O— | CF₃ | CH₂CH₂-(2-OH)Ph | H |
| 1551 | 5,6-OCH₂O— | CF₃ | CH₂CH₂-(3-OH)Ph | H |
| 1552 | 5,6-OCH₂O— | CF₃ | CH₂CH₂-(4-OH)Ph | H |
| 1553 | 5,6-OCH₂O— | CF₃ | CH₂CH₂-(2-OMe)Ph | H |
| 1554 | 5,6-OCH₂O— | CF₃ | CH₂CH₂-(3-OMe)Ph | H |
| 1555 | 5,6-OCH₂O— | CF₃ | CH₂CH₂-(4-OMe)Ph | H |
| 1556 | 5,6-OCH₂O— | CF₃ | CH₂CH₂-(2-CN)Ph | H |
| 1557 | 5,6-OCH₂O— | CF₃ | CH₂CH₂-(3-CN)Ph | H |
| 1558 | 5,6-OCH₂O— | CF₃ | CH₂CH₂-(4-CN)Ph | H |
| 1559 | 5,6-OCH₂O— | CF₃ | CH₂CH₂-(2-NO₂)Ph | H |
| 1560 | 5,6-OCH₂O— | CF₃ | CH₂CH₂-(3-NO₂)Ph | H |
| 1561 | 5,6-OCH₂O— | CF₃ | CH₂CH₂-(4-NO₂)Ph | H |
| 1562 | 5,6-OCH₂O— | CF₃ | CH₂CH₂-(2-NH₂)Ph | H |
| 1563 | 5,6-OCH₂O— | CF₃ | CH₂CH₂-(3-NH₂)Ph | H |
| 1564 | 5,6-OCH₂O— | CF₃ | CH₂CH₂-(4-NH₂)Ph | H |
| 1565 | 5,6-OCH₂O— | CF₃ | CH₂CH₂-(2-NMe₂)Ph | H |
| 1566 | 5,6-OCH₂O— | CF₃ | CH₂CH₂-(3-NMe₂)Ph. | H |
| 1567 | 5,6-OCH₂O— | CF₃ | CH₂CH₂-(4-NMe₂)Ph | H |
| 1568 | 5,6-OCH₂O— | CF₃ | CH₂CH₂-2-Pyridyl | H |
| 1569 | 5,6-OCH₂O— | CF₃ | CH₂CH₂-3-Pyridyl | H |
| 1570 | 5,6-OCH₂O— | CF₃ | CH₂CH₂-4-Pyridyl | H |
| 1571 | 5,6-OCH₂O— | CF₃ | CH₂CH₂-2-furanyl | H |
| 1572 | 5,6-OCH₂O— | CF₃ | CH₂CH₂-3-furanyl | H |
| 1573 | 5,6-OCH₂O— | CF₃ | CH₂CH₂-2-thienyl | H |
| 1574 | 5,6-OCH₂O— | CF₃ | CH₂CH₂-3-thienyl | H |
| 1575 | 5,6-OCH₂O— | CF₃ | CH₂CH₂-2-oxazolyl | H |
| 1576 | 5,6-OCH₂O— | CF₃ | CH₂CH₂-2-thiazolyl | H |
| 1577 | 5,6-OCH₂O— | CF₃ | CH₂CH₂-4-isoxazolyl | H |
| 1578 | 5,6-OCH₂O— | CF₃ | CH₂CH₂-2-imidazolyl | H |
| 1579 | 5,6-OCH₂O— | CF₃ | C≡C-cycPr | CH₃ |
| 1580 | 5,6-OCH₂O— | CF₃ | C≡C—Ph | CH₃ |
| 1581 | 5,6-OCH₂O— | CF₃ | C≡C-2-Pyridyl | CH₃ |
| 1582 | 5,6-OCH₂O— | CF₃ | C≡C-3-Pyridyl | CH₃ |
| 1583 | 5,6-OCH₂O— | CF₃ | C≡C-4-Pyridyl | CH₃ |
| 1584 | 5,6-OCH₂O— | CF₃ | C≡C-2-furanyl | CH₃ |
| 1585 | 5,6-OCH₂O— | CF₃ | C≡C-3-furanyl | CH₃ |
| 1586 | 5,6-OCH₂O— | CF₃ | C≡C-2-thienyl | CH₃ |
| 1587 | 5,6-OCH₂O— | CF₃ | C≡C-3-thienyl | CH₃ |
| 1588 | 5,6-OCH₂O— | CF₃ | C≡C-cycPr | CH₃ |
| 1589 | 5,6-OCH₂O— | CF₃ | C≡C—Ph | CH₃ |
| 1590 | 5,6-OCH₂O— | CF₃ | C≡C-2-Pyridyl | CH₃ |
| 1591 | 5,6-OCH₂O— | CF₃ | C≡C-3-Pyridyl | CH₃ |
| 1592 | 5,6-OCH₂O— | CF₃ | C≡C-4-Pyridyl | CH₃ |
| 1593 | 5,6-OCH₂O— | CF₃ | C≡C-2-furanyl | CH₃ |
| 1594 | 5,6-OCH₂O— | CF₃ | C≡C-3-furanyl | CH₃ |
| 1595 | 5,6-OCH₂O— | CF₃ | C≡C-2-thienyl | CH₃ |
| 1596 | 5,6-OCH₂O— | CF₃ | C≡C-3-thienyl | CH₃ |
| 1597 | 5,6-OCH₂O— | CF₃ | CH₂CH₂-cycPr | CH₃ |
| 1598 | 5,6-OCH₂O— | CF₃ | CH₂CH₂—Ph | CH₃ |
| 1599 | 5,6-OCH₂O— | CF₃ | CH₂CH₂-2-Pyridyl | CH₃ |
| 1600 | 5,6-OCH₂O— | CF₃ | CH₂CH₂-3-Pyridyl | CH₃ |
| 1601 | 5,6-OCH₂O— | CF₃ | CH₂CH₂-4-Pyridyl | CH₃ |
| 1602 | 5,6-OCH₂O— | CF₃ | CH₂CH₂-2-furanyl | CH₃ |
| 1603 | 5,6-OCH₂O— | CF₃ | CH₂CH₂-3-furanyl | CH₃ |
| 1604 | 5,6-OCH₂O— | CF₃ | CH₂CH₂-2-thienyl | CH₃ |
| 1605 | 5,6-OCH₂O— | CF₃ | CH₂CH₂-3-thienyl | CH₃ |
| 1606 | 5,6-OCH₂O— | CF₃ | C≡C-cycPr | CH₂CH₃ |
| 1607 | 5,6-OCH₂O— | CF₃ | C≡C—Ph | CH₂CH₃ |
| 1608 | 5,6-OCH₂O— | CF₃ | C≡C-2-Pyridyl | CH₂CH₃ |
| 1609 | 5,6-OCH₂O— | CF₃ | C≡C-3-Pyridyl | CH₂CH₃ |

TABLE 2*-continued

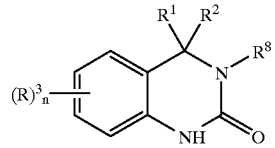

| Ex. # | R³ | R¹ | R² | R⁸ |
|---|---|---|---|---|
| 1610 | 5,6-OCH₂O— | CF₃ | C≡C-4-Pyridyl | CH₂CH₃ |
| 1611 | 5,6-OCH₂O— | CF₃ | C≡C-2-furanyl | CH₂CH₃ |
| 1612 | 5,6-OCH₂O— | CF₃ | C≡C-3-furanyl | CH₂CH₃ |
| 1613 | 5,6-OCH₂O— | CF₃ | C≡C-2-thienyl | CH₂CH₃ |
| 1614 | 5,6-OCH₂O— | CF₃ | C≡C-3-thienyl | CH₂CH₃ |
| 1615 | 5,6-OCH₂O— | CF₃ | C≡C-cycPr | CH₂CH₃ |
| 1616 | 5,6-OCH₂O— | CF₃ | C≡C—Ph | CH₂CH₃ |
| 1617 | 5,6-OCH₂O— | CF₃ | C≡C-2-Pyridyl | CH₂CH₃ |
| 1618 | 5,6-OCH₂O— | CF₃ | C≡C-3-Pyridyl | CH₂CH₃ |
| 1619 | 5,6-OCH₂O— | CF₃ | C≡C-4-Pyridyl | CH₂CH₃ |
| 1620 | 5,6-OCH₂O— | CF₃ | C≡C-2-furanyl | CH₂CH₃ |
| 1621 | 5,6-OCH₂O— | CF₃ | C≡C-3-furanyl | CH₂CH₃ |
| 1622 | 5,6-OCH₂O— | CF₃ | C≡C-2-thienyl | CH₂CH₃ |
| 1623 | 5,6-OCH₂O— | CF₃ | C≡C-3-thienyl | CH₂CH₃ |
| 1624 | 5,6-OCH₂O— | CF₃ | CH₂CH₂-cycPr | CH₂CH₃ |
| 1625 | 5,6-OCH₂O— | CF₃ | CH₂CH₂—Ph | CH₂CH₃ |
| 1626 | 5,6-OCH₂O— | CF₃ | CH₂CH₂-2-Pyridyl | CH₂CH₃ |
| 1627 | 5,6-OCH₂O— | CF₃ | CH₂CH₂-3-Pyridyl | CH₂CH₃ |
| 1628 | 5,6-OCH₂O— | CF₃ | CH₂CH₂-4-Pyridyl | CH₂CH₃ |
| 1629 | 5,6-OCH₂O— | CF₃ | CH₂CH₂-2-furanyl | CH₂CH₃ |
| 1630 | 5,6-OCH₂O— | CF₃ | CH₂CH₂-3-furanyl | CH₂CH₃ |
| 1631 | 5,6-OCH₂O— | CF₃ | CH₂CH₂-2-thienyl | CH₂CH₃ |
| 1632 | 5,6-OCH₂O— | CF₃ | CH₂CH₂-3-thienyl | CH₂CH₃ |

*Unless otherwise indicated, stereochemisty is (+/−)

TABLE 3*

| Ex. # | R³ | R¹ | R² | R⁸ |
|---|---|---|---|---|
| 1 | 6-Cl | CF₃ | C≡C-Pr | H |
| 2 | 6-Cl | CF₃ | C≡C-Bu | H |
| 3 | 6-Cl | CF₃ | C≡C-iBu | H |
| 4 | 6-Cl | CF₃ | C≡C-tBu | H |
| 5 | 6-Cl | CF₃ | C≡C—Me | H |
| 6 | 6-Cl | CF₃ | CH₂CH₂CH₂CH₂CH₃ | H |
| 7 | 6-Cl | CF₃ | CH₂CH₂CH(CH₃)₂ | H |
| 8 | 6-Cl | CF₃ | CH₂CH₂CH₂CH₃ | H |
| 9 | 6-Cl | CF₃ | CH₂CH₂CH₃ | H |
| 10 | 6-Cl | CF₃ | CH₂CH₂-tBu | H |
| 11 | 6-Cl | CF₃ | CH₂C≡C—CH₃ | H |
| 12 | 6-Cl | CF₃ | CH₂C≡C—CH₂CH₃ | H |
| 13 | 6-Cl | CF₃ | C≡C-iPr | CH₃ |
| 14 | 6-Cl | CF₃ | C≡C-Pr | CH₃ |
| 15 | 6-Cl | CF₃ | C≡C-Bu | CH₃ |
| 16 | 6-Cl | CF₃ | C≡C-iBu | CH₃ |
| 17 | 6-Cl | CF₃ | C≡C-tBu | CH₃ |
| 18 | 6-Cl | CF₃ | C≡C—Et | CH₃ |
| 19 | 6-Cl | CF₃ | C≡C—Me | CH₃ |
| 20 | 6-Cl | CF₃ | CH₂C≡C—CH₃ | CH₃ |
| 21 | 6-Cl | CF₃ | CH₂C≡C—CH₂CH₃ | CH₃ |
| 22 | 6-Cl | CF₃ | CH₂CH₂CH(CH₃)₂ | CH₃ |
| 23 | 6-Cl | CF₃ | CH₂CH₂CH₂CH₃ | CH₃ |
| 24 | 6-Cl | CF₃ | CH₂CH₂CH₃ | CH₃ |
| 25 | 6-Cl | CF₃ | CH₂CH₂-tBu | CH₃ |
| 26 | 6-Cl | CF₃ | C≡C-iPr | CH₂CH₃ |
| 27 | 6-Cl | CF₃ | C≡C-Pr | CH₂CH₃ |
| 28 | 6-Cl | CF₃ | C≡C-Bu | CH₂CH₃ |
| 29 | 6-Cl | CF₃ | C≡C-iBu | CH₂CH₃ |
| 30 | 6-Cl | CF₃ | C≡C-tBu | CH₂CH₃ |
| 31 | 6-Cl | CF₃ | C≡C—Et | CH₂CH₃ |
| 32 | 6-Cl | CF₃ | C≡C—Me | CH₂CH₃ |
| 33 | 6-Cl | CF₃ | CH₂C≡C—CH₃ | CH₂CH₃ |
| 34 | 6-Cl | CF₃ | CH₂C≡C—CH₂CH₃ | CH₂CH₃ |
| 35 | 6-Cl | CF₃ | CH₂CH₂CH(CH₃)₂ | CH₂CH₃ |
| 36 | 6-Cl | CF₃ | CH₂CH₂CH₂CH₃ | CH₂CH₃ |
| 37 | 6-Cl | CF₃ | CH₂CH₂CH₃ | CH₂CH₃ |

TABLE 3*-continued

| Ex. # | R³ | R¹ | R² | R⁸ |
|---|---|---|---|---|
| 38 | 6-Cl | CF₃ | CH₂CH₂-tBu | CH₂CH₃ |
| 39 | 6-MeO | CF₃ | C≡C-Pr | H |
| 40 | 6-MeO | CF₃ | C≡C-Bu | H |
| 41 | 6-MeO | CF₃ | C≡C-iBu | H |
| 42 | 6-MeO | CF₃ | C≡C-tBu | H |
| 43 | 6-MeO | CF₃ | C≡C—Et | H |
| 44 | 6-MeO | CF₃ | C≡C—Me | H |
| 45 | 6-MeO | CF₃ | CH₂C≡C—CH₃ | H |
| 46 | 6-MeO | CF₃ | CH₂C≡C—CH₂CH₃ | H |
| 47 | 6-MeO | CF₃ | CH₂CH₂CH₂CH₂CH₃ | H |
| 48 | 6-MeO | CF₃ | CH₂CH₂CH(CH₃)₂ | H |
| 49 | 6-MeO | CF₃ | CH₂CH₂CH₂CH₃ | H |
| 50 | 6-MeO | CF₃ | CH₂CH₂CH₃ | H |
| 51 | 6-MeO | CF₃ | CH₂CH₂-tBu | H |
| 52 | 6-MeO | CF₃ | CH₂C≡C—CH₃ | H |
| 53 | 6-MeO | CF₃ | CH₂C≡C—CH₂CH₃ | H |
| 54 | 6-MeO | CF₃ | C≡C-iPr | CH₃ |
| 55 | 6-MeO | CF₃ | C≡C-Pr | CH₃ |
| 56 | 6-MeO | CF₃ | C≡C-Bu | CH₃ |
| 57 | 6-MeO | CF₃ | C≡C-iBu | CH₃ |
| 58 | 6-MeO | CF₃ | C≡C-tBu | CH₃ |
| 59 | 6-MeO | CF₃ | C≡C—Et | CH₃ |
| 60 | 6-MeO | CF₃ | C≡C—Me | CH₃ |
| 61 | 6-MeO | CF₃ | CH₂C≡C—CH₃ | CH₃ |
| 62 | 6-MeO | CF₃ | CH₂C≡C—CH₂CH₃ | CH₃ |
| 63 | 6-MeO | CF₃ | CH₂CH₂CH(CH₃)₂ | CH₃ |
| 64 | 6-MeO | CF₃ | CH₂CH₂CH₂CH₃ | CH₃ |
| 65 | 6-MeO | CF₃ | CH₂CH₂CH₃ | CH₃ |
| 66 | 6-MeO | CF₃ | CH₂CH₂-tBu | CH₃ |
| 67 | 6-MeO | CF₃ | C≡C-iPr | CH₂CH₃ |
| 68 | 6-MeO | CF₃ | C≡C-Pr | CH₂CH₃ |
| 69 | 6-MeO | CF₃ | C≡C-Bu | CH₂CH₃ |
| 70 | 6-MeO | CF₃ | C≡C-iBu | CH₂CH₃ |
| 71 | 6-MeO | CF₃ | C≡C-tBu | CH₂CH₃ |
| 72 | 6-MeO | CF₃ | C≡C—Et | CH₂CH₃ |
| 73 | 6-MeO | CF₃ | C≡C—Me | CH₂CH₃ |
| 74 | 6-MeO | CF₃ | CH₂C≡C—CH₃ | CH₂CH₃ |
| 75 | 6-MeO | CF₃ | CH₂C≡C—CH₂CH₃ | CH₂CH₃ |
| 76 | 6-MeO | CF₃ | CH₂CH₂CH(CH₃)₂ | CH₂CH₃ |
| 77 | 6-MeO | CF₃ | CH₂CH₂CH₂CH₃ | CH₂CH₃ |
| 78 | 6-MeO | CF₃ | CH₂CH₂CH₃ | CH₂CH₃ |
| 79 | 6-MeO | CF₃ | CH₂CH₂-tBu | CH₂CH₃ |
| 80 | 5,6-diF | CF₃ | C≡C-Pr | H |
| 81 | 5,6-diF | CF₃ | C≡C-Bu | H |
| 82 | 5,6-diF | CF₃ | C≡C-iBu | H |
| 83 | 5,6-diF | CF₃ | C≡C-tBu | H |
| 84 | 5,6-diF | CF₃ | C≡C-Me | H |
| 85 | 5,6-diF | CF₃ | CH₂C≡C—CH₃ | H |
| 86 | 5,6-diF | CF₃ | CH₂C≡C—CH₂CH₃ | H |
| 87 | 5,6-diF | CF₃ | CH₂CH₂CH₂CH₂CH₃ | H |
| 88 | 5,6-diF | CF₃ | CH₂CH₂CH₃ | H |
| 89 | 5,6-diF | CF₃ | CH₂CH₂-tBu | H |
| 90 | 5,6-diF | CF₃ | C≡C-iPr | CH₃ |
| 91 | 5,6-diF | CF₃ | C≡C-Pr | CH₃ |
| 92 | 5,6-diF | CF₃ | C≡C-Bu | CH₃ |
| 93 | 5,6-diF | CF₃ | C≡C-iBu | CH₃ |
| 94 | 5,6-diF | CF₃ | C≡C-tBu | CH₃ |
| 95 | 5,6-diF | CF₃ | C≡C—Et | CH₃ |
| 96 | 5,6-diF | CF₃ | C≡C—Me | CH₃ |
| 97 | 5,6-diF | CF₃ | C≡C-Ph | CH₃ |
| 98 | 5,6-diF | CF₃ | CH₂C≡C—CH₃ | CH₃ |
| 99 | 5,6-diF | CF₃ | CH₂C≡C—CH₂CH₃ | CH₃ |
| 100 | 5,6-diF | CF₃ | CH₂CH₂CH(CH₃)₂ | CH₃ |
| 101 | 5,6-diF | CF₃ | CH₂CH₂CH₂CH₃ | CH₃ |
| 102 | 5,6-diF | CF₃ | CH₂CH₂CH₃ | CH₃ |
| 103 | 5,6-diF | CF₃ | CH₂CH₂-tBu | CH₃ |
| 104 | 5,6-diF | CF₃ | C≡C-iPr | CH₂CH₃ |
| 105 | 5,6-diF | CF₃ | C≡C-Pr | CH₂CH₃ |
| 106 | 5,6-diF | CF₃ | C≡C-Bu | CH₂CH₃ |
| 107 | 5,6-diF | CF₃ | C≡C-iBu | CH₂CH₃ |
| 108 | 5,6-diF | CF₃ | C≡C-tBu | CH₂CH₃ |
| 109 | 5,6-diF | CF₃ | C≡C—Et | CH₂CH₃ |
| 110 | 5,6-diF | CF₃ | C≡C—Me | CH₂CH₃ |
| 111 | 5,6-diF | CF₃ | CH₂C≡C—CH₃ | CH₂CH₃ |
| 112 | 5,6-diF | CF₃ | CH₂C≡C—CH₂CH₃ | CH₂CH₃ |
| 113 | 5,6-diF | CF₃ | CH₂CH₂CH(CH₃)₂ | CH₂CH₃ |
| 114 | 5,6-diF | CF₃ | CH₂CH₂CH₂CH₃ | CH₂CH₃ |

TABLE 3*-continued

| Ex. # | $R^3$ | $R^1$ | $R^2$ | $R^8$ |
|---|---|---|---|---|
| 115 | 5,6-diF | $CF_3$ | $CH_2CH_2CH_3$ | $CH_2CH_3$ |
| 116 | 5,6-diF | $CF_3$ | $CH_2CH_2$-tBu | $CH_2CH_3$ |
| 117 | 6-F | $CF_3$ | C≡C-Pr | H |
| 118 | 6-F | $CF_3$ | C≡C-Bu | H |
| 119 | 6-F | $CF_3$ | C≡C-iBu | H |
| 120 | 6-F | $CF_3$ | C≡C-tBu | H |
| 121 | 6-F | $CF_3$ | C≡C—Me | H |
| 122 | 6-F | $CF_3$ | $CH_2$C≡C—$CH_2CH_3$ | H |
| 123 | 6-F | $CF_3$ | $CH_2CH_2CH_2CH_3$ | H |
| 124 | 6-F | $CF_3$ | $CH_2CH_2CH_3$ | H |
| 125 | 6-F | $CF_3$ | $CH_2CH_2$-tBu | H |
| 126 | 6-F | $CF_3$ | C≡C-iPr | $CH_3$ |
| 127 | 6-F | $CF_3$ | C≡C-Pr | $CH_3$ |
| 128 | 6-F | $CF_3$ | C≡C-Bu | $CH_3$ |
| 129 | 6-F | $CF_3$ | C≡C-iBu | $CH_3$ |
| 130 | 6-F | $CF_3$ | C≡C-tBu | $CH_3$ |
| 131 | 6-F | $CF_3$ | C≡C—Et | $CH_3$ |
| 132 | 6-F | $CF_3$ | C≡C—Me | $CH_3$ |
| 133 | 6-F | $CF_3$ | $CH_2$C≡C—$CH_3$ | $CH_3$ |
| 134 | 6-F | $CF_3$ | $CH_2$C≡C—$CH_2CH_3$ | $CH_3$ |
| 135 | 6-F | $CF_3$ | $CH_2CH_2CH(CH_3)_2$ | $CH_3$ |
| 136 | 6-F | $CF_3$ | $CH_2CH_2CH_2CH_3$ | $CH_3$ |
| 137 | 6-F | $CF_3$ | $CH_2CH_2CH_3$ | $CH_3$ |
| 138 | 6-F | $CF_3$ | $CH_2CH_2$-tBu | $CH_3$ |
| 139 | 6-F | $CF_3$ | C≡-C-iPr | $CH_2CH_3$ |
| 140 | 6-F | $CF_3$ | C≡C-Pr | $CH_2CH_3$ |
| 141 | 6-F | $CF_3$ | C≡C-Bu | $CH_2CH_3$ |
| 142 | 6-F | $CF_3$ | C≡C-iBu | $CH_2CH_3$ |
| 143 | 6-F | $CF_3$ | C≡C-tBu | $CH_2CH_3$ |
| 144 | 6-F | $CF_3$ | C≡C—Et | $CH_2CH_3$ |
| 145 | 6-F | $CF_3$ | C≡C—Me | $CH_2CH_3$ |
| 146 | 6-F | $CF_3$ | $CH_2$C≡C—$CH_3$ | $CH_2CH_3$ |
| 147 | 6-F | $CF_3$ | $CH_2$C≡C—$CH_2CH_3$ | $CH_2CH_3$ |
| 148 | 6-F | $CF_3$ | $CH_2CH_2CH(CH_3)_2$ | $CH_2CH_3$ |
| 149 | 6-F | $CF_3$ | $CH_2CH_2CH_2CH_3$ | $CH_2CH_3$ |
| 150 | 6-F | $CF_3$ | $CH_2CH_2CH_3$ | $CH_2CH_3$ |
| 151 | 6-F | $CF_3$ | $CH_2CH_2$-tBu | $CH_2CH_3$ |
| 152 | 5-Cl | $CF_3$ | C≡C-iPr | H |
| 153 | 5-Cl | $CF_3$ | C≡C-Pr | H |
| 154 | 5-Cl | $CF_3$ | C≡C-Bu | H |
| 155 | 5-Cl | $CF_3$ | C≡-C-iBu | H |
| 156 | 5-Cl | $CF_3$ | C≡C-tBu | H |
| 157 | 5-Cl | $CF_3$ | C≡C—Et | H |
| 158 | 5-Cl | $CF_3$ | C≡C—Me | H |
| 159 | 5-Cl | $CF_3$ | $CH_2$C≡C—$CH_3$ | H |
| 160 | 5-Cl | $CF_3$ | $CH_2$C≡C—$CH_2CH_3$ | H |
| 161 | 5-Cl | $CF_3$ | $CH_2CH_2CH_2CH_3$ | H |
| 162 | 5-Cl | $CF_3$ | $CH_2CH_2CH(CH_3)_2$ | H |
| 163 | 5-Cl | $CF_3$ | $CH_2CH_2CH_2CH_3$ | H |
| 164 | 5-Cl | $CF_3$ | $CH_2CH_2CH_3$ | H |
| 165 | 5-Cl | $CF_3$ | $CH_2CH_2$-tBu | H |
| 166 | 5-Cl | $CF_3$ | C≡C-iPr | $CH_3$ |
| 167 | 5-Cl | $CF_3$ | C≡C-Pr | $CH_3$ |
| 168 | 5-Cl | $CF_3$ | C≡C-Bu | $CH_3$ |
| 169 | 5-Cl | $CF_3$ | C≡C-iBu | $CH_3$ |
| 170 | 5-Cl | $CF_3$ | C≡C-tBu | $CH_3$ |
| 171 | 5-Cl | $CF_3$ | C≡C—Et | $CH_3$ |
| 172 | 5-Cl | $CF_3$ | C≡C—Me | $CH_3$ |
| 173 | 5-Cl | $CF_3$ | $CH_2$C≡C—$CH_3$ | $CH_3$ |
| 174 | 5-Cl | $CF_3$ | $CH_2$C≡C—$CH_2CH_3$ | $CH_3$ |
| 175 | 5-Cl | $CF_3$ | $CH_2CH_2CH(CH_3)_2$ | $CH_3$ |
| 176 | 5-Cl | $CF_3$ | $CH_2CH_2CH_2CH_3$ | $CH_3$ |
| 177 | 5-Cl | $CF_3$ | $CH_2CH_2CH_3$ | $CH_3$ |
| 178 | 5-Cl | $CF_3$ | $CH_2CH_2$-tBu | $CH_3$ |
| 179 | 5-Cl | $CF_3$ | C≡C-iPr | $CH_2CH_3$ |
| 180 | 5-Cl | $CF_3$ | C≡-C-Pr | $CH_2CH_3$ |
| 181 | 5-Cl | $CF_3$ | C≡C-Bu | $CH_2CH_3$ |
| 182 | 5-Cl | $CF_3$ | C≡C-iBu | $CH_2CH_3$ |
| 183 | 5-Cl | $CF_3$ | C≡C-tBu | $CH_2CH_3$ |
| 184 | 5-Cl | $CF_3$ | C≡C—Et | $CH_2CH_3$ |
| 185 | 5-Cl | $CF_3$ | C≡C—Me | $CH_2CH_3$ |
| 186 | 5-Cl | $CF_3$ | $CH_2$C≡C—$CH_3$ | $CH_2CH_3$ |
| 187 | 5-Cl | $CF_3$ | $CH_2$C≡C—$CH_2CH_3$ | $CH_2CH_3$ |
| 188 | 5-Cl | $CF_3$ | $CH_2CH_2CH(CH_3)_2$ | $CH_2CH_3$ |
| 189 | 5-Cl | $CF_3$ | $CH_2CH_2CH_2CH_3$ | $CH_2CH_3$ |
| 190 | 5-Cl | $CF_3$ | $CH_2CH_2CH_3$ | $CH_2CH_3$ |
| 191 | 5-Cl | $CF_3$ | $CH_2CH_2$-tBu | $CH_2CH_3$ |
| 192 | 5-F | $CF_3$ | C≡C-iPr | H |
| 193 | 5-F | $CF_3$ | C≡C-Pr | H |
| 194 | 5-F | $CF_3$ | C≡C-Bu | H |
| 195 | 5-F | $CF_3$ | C≡C-iBu | H |
| 196 | 5-F | $CF_3$ | C≡C-tBu | H |
| 197 | 5-F | $CF_3$ | C≡C—Et | H |
| 198 | 5-F | $CF_3$ | C≡C—Me | H |
| 199 | 5-F | $CF_3$ | $CH_2$C≡C—$CH_3$ | H |
| 200 | 5-F | $CF_3$ | $CH_2$C≡C—$CH_2CH_3$ | H |
| 201 | 5-F | $CF_3$ | $CH_2CH_2CH_2CH_3$ | H |
| 202 | 5-F | $CF_3$ | $CH_2CH_2CH(CH_3)_2$ | H |
| 203 | 5-F | $CF_3$ | $CH_2CH_2CH_2CH_3$ | H |
| 204 | 5-F | $CF_3$ | $CH_2CH_2CH_3$ | H |
| 205 | 5-F | $CF_3$ | $CH_2CH_2$-tBu | H |
| 206 | 5-F | $CF_3$ | C≡C-iPr | $CH_3$ |
| 207 | 5-F | $CF_3$ | C≡C-Pr | $CH_3$ |
| 208 | 5-F | $CF_3$ | C≡C-Bu | $CH_3$ |
| 209 | 5-F | $CF_3$ | C≡C-iBu | $CH_3$ |
| 210 | 5-F | $CF_3$ | C≡C-tBu | $CH_3$ |
| 211 | 5-F | $CF_3$ | C≡C—Et | $CH_3$ |
| 212 | 5-F | $CF_3$ | C≡C—Me | $CH_3$ |
| 213 | 5-F | $CF_3$ | $CH_2$C≡C—$CH_3$ | $CH_3$ |
| 214 | 5-F | $CF_3$ | $CH_2$C≡C—$CH_2CH_3$ | $CH_3$ |
| 215 | 5-F | $CF_3$ | $CH_2CH_2CH(CH_3)_2$ | $CH_3$ |
| 216 | 5-F | $CF_3$ | $CH_2CH_2CH_2CH_3$ | $CH_3$ |
| 217 | 5-F | $CF_3$ | $CH_2CH_2CH_3$ | $CH_3$ |
| 218 | 5-F | $CF_3$ | $CH_2CH_2$-tBu | $CH_3$ |
| 219 | 5-F | $CF_3$ | C≡C-iPr | $CH_2CH_3$ |
| 220 | 5-F | $CF_3$ | C≡C-Pr | $CH_2CH_3$ |
| 221 | 5-F | $CF_3$ | C≡C-Bu | $CH_2CH_3$ |
| 222 | 5-F | $CF_3$ | C≡C-iBu | $CH_2CH_3$ |
| 223 | 5-F | $CF_3$ | C≡C-tBu | $CH_2CH_3$ |
| 224 | 5-F | $CF_3$ | C≡C—Et | $CH_2CH_3$ |
| 225 | 5-F | $CF_3$ | C≡-C-Me | $CH_2CH_3$ |
| 226 | 5-F | $CF_3$ | $CH_2$C≡C—$CH_3$ | $CH_2CH_3$ |
| 227 | 5-F | $CF_3$ | $CH_2$C≡C—$CH_2CH_3$ | $CH_2CH_3$ |
| 228 | 5-F | $CF_3$ | $CH_2CH_2CH(CH_3)_2$ | $CH_2CH_3$ |
| 229 | 5-F | $CF_3$ | $CH_2CH_2CH_2CH_3$ | $CH_2CH_3$ |
| 230 | 5-F | $CF_3$ | $CH_2CH_2CH_3$ | $CH_2CH_3$ |
| 231 | 5-F | $CF_3$ | $CH_2CH_2$-tBu | $CH_2CH_3$ |
| 232 | 5-Cl,6-F | $CF_3$ | C≡C-iPr | H |
| 233 | 5-Cl,6-F | $CF_3$ | C≡C-Pr | H |
| 234 | 5-Cl,6-F | $CF_3$ | C≡C-Bu | H |
| 235 | 5-Cl,6-F | $CF_3$ | C≡C-iBu | H |
| 236 | 5-Cl,6-F | $CF_3$ | C≡C-tBu | H |
| 237 | 5-Cl,6-F | $CF_3$ | C≡C—Et | H |
| 238 | 5-Cl,6-F | $CF_3$ | C≡C—Me | H |
| 239 | 5-Cl,6-F | $CF_3$ | $CH_2$C≡C—$CH_3$ | H |
| 240 | 5-Cl,6-F | $CF_3$ | $CH_2$C≡C—$CH_2CH_3$ | H |
| 241 | 5-Cl,6-F | $CF_3$ | $CH_2CH_2CH(CH_3)_2$ | H |
| 242 | 5-Cl,6-F | $CF_3$ | $CH_2CH_2CH_2CH_3$ | H |
| 243 | 5-Cl,6-F | $CF_3$ | $CH_2CH_2CH_3$ | H |
| 244 | 5-Cl,6-F | $CF_3$ | $CH_2CH_2$-tBu | H |
| 245 | 5-Cl,6-F | $CF_3$ | C≡C-iPr | $CH_3$ |
| 246 | 5-Cl,6-F | $CF_3$ | C≡C-Pr | $CH_3$ |
| 247 | 5-Cl,6-F | $CF_3$ | C≡C-Bu | $CH_3$ |
| 248 | 5-Cl,6-F | $CF_3$ | C≡C-iBu | $CH_3$ |
| 249 | 5-Cl,6-F | $CF_3$ | C≡C-tBu | $CH_3$ |
| 250 | 5-Cl,6-F | $CF_3$ | C≡C—Et | $CH_3$ |
| 251 | 5-Cl,6-F | $CF_3$ | C≡C—Me | $CH_3$ |
| 252 | 5-Cl,6-F | $CF_3$ | $CH_2$C≡C—$CH_3$ | $CH_3$ |
| 253 | 5-Cl,6-F | $CF_3$ | $CH_2$C≡C—$CH_2CH_3$ | $CH_3$ |
| 254 | 5-Cl,6-F | $CF_3$ | $CH_2CH_2CH(CH_3)_2$ | $CH_3$ |
| 255 | 5-Cl,6-F | $CF_3$ | $CH_2CH_2CH_2CH_3$ | $CH_3$ |
| 256 | 5-Cl,6-F | $CF_3$ | $CH_2CH_2CH_3$ | $CH_3$ |
| 257 | 5-Cl,6-F | $CF_3$ | $CH_2CH_2$-tBu | $CH_3$ |
| 258 | 6-Cl,8-F | $CF_3$ | C≡C-iPr | H |
| 259 | 6-Cl,8-F | $CF_3$ | C≡C-Pr | H |
| 260 | 6-Cl,8-F | $CF_3$ | C≡C-BU | H |
| 261 | 6-Cl,8-F | $CF_3$ | C≡C-iBu | H |
| 262 | 6-Cl,8-F | $CF_3$ | C≡C-tBu | H |
| 263 | 6-Cl,8-F | $CF_3$ | C≡C—Et | H |
| 264 | 6-Cl,8-F | $CF_3$ | C≡C—Me | H |
| 265 | 6-Cl,8-F | $CF_3$ | $CH_2$C≡C—$CH_3$ | H |
| 266 | 6-Cl,8-F | $CF_3$ | $CH_2$C≡C—$CH_2CH_3$ | H |
| 267 | 6-Cl,8-F | $CF_3$ | $CH_2CH_2CH(CH_3)_2$ | |
| 268 | 6-Cl,8-F | $CF_3$ | $CH_2CH_2CH_2CH_3$ | H |

TABLE 3*-continued

| Ex. # | R³ | R¹ | R² | R⁸ |
|---|---|---|---|---|
| 269 | 6-Cl,8-F | CF₃ | CH₂CH₂CH₃ | H |
| 270 | 6-Cl,8-F | CF₃ | CH₂CH₂-tBu | H |
| 271 | 6-Cl,8-F | CF₃ | C≡C-iPr | CH₃ |
| 272 | 6-Cl,8-F | CF₃ | C≡C-Pr | CH₃ |
| 273 | 6-Cl,8-F | CF₃ | C≡C-Bu | CH₃ |
| 274 | 6-Cl,8-F | CF₃ | C≡C-iBu | CH₃ |
| 275 | 6-Cl,8-F | CF₃ | C≡C-tBu | CH₃ |
| 276 | 6-Cl,8-F | CF₃ | C≡C—Et | CH₃ |
| 277 | 6-Cl,8-F | CF₃ | C≡C—Me | CH₃ |
| 278 | 6-Cl,8-F | CF₃ | CH₂C≡C—CH₃ | CH₃ |
| 279 | 6-Cl,8-F | CF₃ | CH₂C≡C—CH₂CH₃ | CH₃ |
| 280 | 6-Cl,8-F | CF₃ | CH₂CH₂CH(CH₃)₂ | CH₃ |
| 281 | 6-Cl,8-F | CF₃ | CH₂CH₂CH₂CH₃ | CH₃ |
| 282 | 6-Cl,8-F | CF₃ | CH₂CH₂CH₃ | CH₃ |
| 283 | 6-Cl,8-F | CF₃ | CH₂CH₂-tBu | CH₃ |
| 284 | 6-CH₃ | CF₃ | C≡C-iPr | H |
| 285 | 6-CH₃ | CF₃ | C≡C-Pr | H |
| 286 | 6-CH₃ | CF₃ | C≡C-Bu | H |
| 287 | 6-CH₃ | CF₃ | C≡C-iBu | H |
| 288 | 6-CH₃ | CF₃ | C≡C-tBu | H |
| 289 | 6-CH₃ | CF₃ | C≡C—Et | H |
| 290 | 6-CH₃ | CF₃ | C≡C—Me | H |
| 291 | 6-CH₃ | CF₃ | CH₂C≡C—CH₃ | H |
| 292 | 6-CH₃ | CF₃ | CH₂C≡C—CH₂CH₃ | H |
| 293 | 6-CH₃ | CF₃ | CH₂CH₂CH(CH₃)₂ | H |
| 294 | 6-CH₃ | CF₃ | CH₂CH₂CH₂CH₃ | H |
| 295 | 6-CH₃ | CF₃ | CH₂CH₂CH₃ | H |
| 296 | 6-CH₃ | CF₃ | CH₂CH₂-tBu | H |
| 297 | 6-CH₃ | CF₃ | C≡C-iPr | CH₃ |
| 298 | 6-CH₃ | CF₃ | C≡C-Pr | CH₃ |
| 299 | 6-CH₃ | CF₃ | C≡C-Bu | CH₃ |
| 300 | 6-CH₃ | CF₃ | C≡C-iBu | CH₃ |
| 301 | 6-CH₃ | CF₃ | C≡C-tBu | CH₃ |
| 302 | 6-CH₃ | CF₃ | C≡C—Et | CH₃ |
| 303 | 6-CH₃ | CF₃ | C≡C—Me | CH₃ |
| 304 | 6-CH₃ | CF₃ | CH₂C≡C—CH₃ | CH₃ |
| 305 | 6-CH₃ | CF₃ | CH₂C≡C—CH₂CH₃ | CH₃ |
| 306 | 6-CH₃ | CF₃ | CH₂CH₂CH(CH₃)₂ | CH₃ |
| 307 | 6-CH₃ | CF₃ | CH₂CH₂CH₂CH₃ | CH₃ |
| 308 | 6-CH₃ | CF₃ | CH₂CH₂CH₃ | CH₃ |
| 309 | 6-CH₃ | CF₃ | CH₂CH₂-tBu | CH₃ |
| 310 | 6-COCH₃ | CF₃ | C≡C-iPr | H |
| 311 | 6-COCH₃ | CF₃ | C≡C-Pr | H |
| 312 | 6-COCH₃ | CF₃ | C≡C-Bu | H |
| 313 | 6-COCH₃ | CF₃ | C≡C-iBu | H |
| 314 | 6-COCH₃ | CF₃ | C≡C-tBu | H |
| 315 | 6-COCH₃ | CF₃ | C≡C—Et | H |
| 316 | 6-COCH₃ | CF₃ | C≡C—Me | H |
| 317 | 6-NH₂ | CF₃ | C≡C-iPr | H |
| 318 | 6-NH₂ | CF₃ | C≡C-Pr | H |
| 319 | 6-NH₂ | CF₃ | C≡C-Bu | H |
| 320 | 6-NH₂ | CF₃ | C≡C-iBu | H |
| 321 | 6-NH₂ | CF₃ | C≡C-tBu | H |
| 322 | 6-NH₂ | CF₃ | C≡C—Et | H |
| 323 | 6-NH₂ | CF₃ | C≡C—Me | H |
| 324 | 6-NMe₂ | CF₃ | C≡C-iPr | H |
| 325 | 6-NMe₂ | CF₃ | C≡C-Pr | H |
| 326 | 6-NMe₂ | CF₃ | C≡C-Bu | H |
| 327 | 6-NMe₂ | CF₃ | C≡C-iBu | H |
| 328 | 6-NMe₂ | CF₃ | C≡C-tBu | H |
| 329 | 6-NMe₂ | CF₃ | C≡C—Et | H |
| 330 | 6-NMe₂ | CF₃ | C≡C—Me | H |
| 331 | 7-Cl | CF₃ | C≡C-iPr | H |
| 332 | 7-Cl | CF₃ | C≡C-Pr | H |
| 333 | 7-Cl | CF₃ | C≡C-Bu | H |
| 334 | 7-Cl | CF₃ | C≡C-iBu | H |
| 335 | 7-Cl | CF₃ | C≡C-tBu | H |
| 336 | 7-Cl | CF₃ | C≡-C—Et | H |
| 337 | 7-Cl | CF₃ | C≡C—Me | H |

*Unless otherwise indicated, stereochemistry is (+/−)

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and In Vitro RNA Transcripts

Plasmid pDAB 72 containing both gag and pol sequences of BH10 (bp 113-1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCT-TGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCT-TACTTTGATAAAACCTC 3') was complementary to nucleotides 2403–2425 of HXB2. The gag reporter probe (5' CCCAGTATTTGTCTACAGCCTTCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 $\mu$M stocks in 2×SSC (0.3 M NaCl, 0.03 M sodium citrate), 0.05 M Tris pH 8.8, 1 mg/mL BSA. The biotinylated capture probes were prepared as 100 $\mu$M stocks in water.

Streptavidin Coated Plates

Streptavidin coated plates were obtained from Du Pont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM l-glutamine and 50 $\mu$g/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1 (RF) stocks were 1–3×10$^7$ PFU (plaque forming units )/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×10$^5$ cells/mL in RPMI 1640, 5% FCS for bulk infections or at 2×10$^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final quanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 $\mu$L) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline (PBS), 0.05% Tween 20.) A second hybridization of reporter probe to the immobilized complex of capture probe and hybridized target RNA was carried out in the washed streptavidin coated well by addition of 120 $\mu$l of a hybridization cocktail containing 4×SSC, 0.66% Triton× 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 $\mu$L of 0.2 mM 4-methylumbelliferyl phosphate (MUBP, JBL Scientific) in buffer $\delta$ (2.5 M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 $\mu$L) were added to a final concentration of 5×10$^5$ per mL (1×10$^5$ per well). Cells were incubated with compounds for 30 minutes at 37° C. in a CO$_2$ incubator. For evaluation of antiviral potency, an appropriate dilution of HIV-1 (RF) virus stock (50 $\mu$L) was added to culture wells containing cells and dilutions of the test compounds. The final volume in each well was 200 $\mu$L. Eight wells per plate were left uninfected with 50 $\mu$L of medium added in place of virus, while eight wells were infected in the absence of any antiviral compound. For evaluation of compound toxicity, parallel plates were cultured without virus infection.

After 3 days of culture at 37° C. in a humidified chamber inside a CO$_2$ incubator, all but 25 $\mu$L of medium/well was removed from the HIV infected plates. Thirty seven $\mu$L of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 $\mu$L of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an IC$_{90}$ value (concentration of compound required to reduce the HIV RNA level by 90%) for dideoxycytidine (ddC) of 0.2 $\mu$g/mL. IC$_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, IC$_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The IC$_{90}$ for ddC, determined in each assay run, should be between 0.1 and 0.3 $\mu$g/mL. Finally, the plateau level of viral RNA produced by an effective reverse transcriptase inhibitor should be less than 10% of the level achieved in an uninhibited infection. A compound was considered active if its IC$_{90}$ was found to be less than 20 $\mu$M.

For antiviral potency tests, all manipulations in microtiter plates, following the initial addition of 2× concentrated compound solution to a single row of wells, were performed using a Perkin Elmer/Cetus ProPette.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of the mutant viruses. The concentration of compound required for 90% inhibition of virus replication as measured in a sensitive viral RNA-based detection method is designated the IC90. It is desirable to have a compound which has a high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelating capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a table or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of United States is:

1. A compound of formula (I):

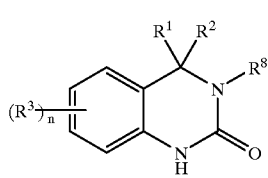

or a stereoisomer or pharmaceutically acceptable salt form thereof, wherein:

$R^1$ is $C_{1-3}$ alkyl substituted with 1–7 halogen;

$R^2$ is selected from $C_{1-5}$ alkyl substituted with 1–2 $R^4$, $C_{2-5}$ alkenyl substituted with 1–2 $R^4$, and $C_{2-5}$ alkynyl substituted with 1 $R^4$;

$R^3$, at each occurrence, is independently selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

$R^4$ is selected from $C_{3-5}$ cycloalkyl substituted with 0–2 $R^3$, phenyl substituted with 0–5 $R^3$, and a 5–6 membered heterocyclic group substituted with 0–2 $R^3$, the heterocyclic group is selected from 2-pyrrolidonyl, 2H-pyrrolyl, 4-piperidonyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, piperazinyl, piperidinyl, pteridinyl, piperidonyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl;

$R^5$ and $R^{5a}$ are independently selected from H and $C_{1-3}$ alkyl;

$R^6$ is selected from H, OH, $C_{1-4}$ alkyl, $C_{1-4}$ alkoxy, and $NR^5R^{5a}$;

$R^7$ is selected from $C_{1-3}$ alkyl and $C_{1-3}$ alkoxy;

$R^8$ is selected from H, cyclopropyl, cyclobutyl, cyclopentyl, methyl, ethyl, n-propyl, and i-propyl; and, n is selected from 0, 1, 2, 3, and 4.

2. A compound according to claim 1, wherein:

$R^1$ is $C_{1-3}$ alkyl substituted with 1–7 halogen;

$R^2$ is selected from $C_{1-5}$ alkyl substituted with 1 $R^4$, $C_{2-5}$ alkenyl substituted with 1 $R^4$, and $C_{2-5}$ alkynyl substituted with 1 $R^4$;

$R^3$, at each occurrence, is independently selected from $C_{1-4}$ alkyl, OH, $C_{1-4}$ alkoxy, F, Cl, Br, I, $NR^5R^{5a}$, $NO_2$, CN, $C(O)R^6$, $NHC(O)R^7$, and $NHC(O)NR^5R^{5a}$;

$R^4$ is selected from $C_{3-5}$ cycloalkyl substituted with 0–2 $R^3$, phenyl substituted with 0–2 $R^3$, and a 5–6 membered heterocyclic group substituted with 0–2 $R^3$, the heterocyclic group is selected from 2-pyrrolidonyl, 2H-pyrrolyl, 4-piperidonyl, 6H-1,2,5-thiadiazinyl, 2H,6H-1,5,2-diathiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, piperazinyl, piperidinyl, pteridinyl, piperidonyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl;

$R^5$ and $R^{5a}$ are independently selected from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$; and, n is selected from 0, 1, 2, and 3.

3. A compound according to claim 2, wherein:

$R^1$ is selected from $CF_3$, and $C_2F_5$;

$R^2$ is selected from $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, at each occurrence, is independently selected from $C_{1-3}$ alkyl, OH, $C_{1-3}$ alkoxy, F, Cl, Br, I, $NR^5R^{5a}$, $NO_2$, CN, $C(O)R^6$, $NHC(O)R^7$, and $NHC(O)NR^5R^{5a}$;

$R^4$ is selected from $C_{3-5}$ cycloalkyl substituted with 0–2 $R^3$, phenyl substituted with 0–2 $R^3$, and a 5–6 membered heterocyclic group substituted with 0–2 $R^3$, the heterocyclic group is selected from 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, piperazinyl, piperidinyl, pteridinyl, piperidonyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl;

$R^5$ and $R^{5a}$ are independently selected from H and $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$; and, n is selected from 0, 1, and 2.

4. A compound according to claim 3, wherein:

$R^1$ is $CF_3$;

$R^2$ is selected from $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, at each occurrence, is independently selected from $C_{1-3}$ alkyl, OH, $C_{1-3}$ alkoxy, F, Cl, $NR^5R^{5a}$, $NO_2$, CN, $C(O)R^6$, $NHC(O)R^7$, and $NHC(O)NR^5R^{5a}$;

$R^4$ is selected from cyclopropyl substituted with 0–1 $R^3$, phenyl substituted with 0–2 $R^3$, and a 5–6 membered heterocyclic system containing 1–3 heteroatoms selected from O, N, and S, substituted with 0–1 $R^3$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^5$ and $R^{5a}$ are independently selected from H, $CH_3$ and $C_2H_5$;

$R^6$ is selected from H, OH, $CH_3$, $C_2H_5$, $OCH_3$, $OC_2H_5$, and $NR^5R^{5a}$;

$R^7$ is selected from $CH_3$, $C_2H_5$, $OCH_3$, and $OC_2H_5$; and, n is selected from 1 and 2.

5. A compound according to claim 4, wherein the compound is of formula Ia:

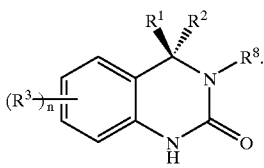

Ia

6. A compound according to claim 4, wherein the compound is of formula Ia:

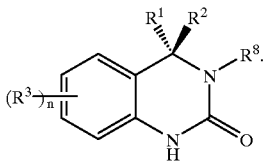

Ib

7. A compound according to claim 1, wherein the compound is selected from:
(+/−)-6-Chloro-4-cyclopropylethynyl-4-trifluoromethyl-3,4-dihydro-2(1H)-quinazolinone;
(+/−)-6-Chloro-4-(2-pyridyl)ethynyl-4-trifluoromethyl-3,4-dihydro-2(1H)-quinazolinone;
(+/−)-6-Chloro-4-phenylethynyl-4-trifluoromethyl-3,4-dihydro-2(1H)-quinazolinone;
(+/−)-4-Cyclopropylethynyl-6-methoxy-4-trifluoromethyl-3,4-dihydro-2(1H)-quinazolinone;
(+/−)-6-Methoxy-4-(2-pyridyl)ethynyl-4-trifluoromethyl-3,4-dihydro-2(1H)-quinazolinone;
(+/−)-6-Methoxy-4-phenylethynyl-4-trifluoromethyl-3,4-dihydro-2(1H)-quinazolinone;
(+/−)-4-Cyclopropylethynyl-5,6-difluoro-4-trifluoromethyl-3,4-dihydro-2(1H)-quinazolinone;
(+/−)-5,6-Difluoro-4-(2-pyridyl)ethynyl-4-trifluoromethyl-3,4-dihydro-2(1H)-quinazolinone;
(+/−)-5,6-Difluoro-4-phenylethynyl-4-trifluoromethyl-3,4-dihydro-2(1H)-quinazolinone;
(+/−)-4-Cyclopropylethynyl-6-fluoro-4-trifluoromethyl-3,4-dihydro-2(1H)-quinazolinone;
(+/−)-6-Fluoro-4-(2-pyridyl)ethynyl-4-trifluoromethyl-3,4-dihydro-2(1H)-quinazolinone;
(+/−)-6-Fluoro-4-phenylethynyl-4-trifluoromethyl-3,4-dihydro-2(1H)-quinazolinone;
(+/−)-6-Fluoro-4-(2'-2-pyridyl)ethyl-4-trifluoromethyl-3,4-dihydro-2(1H)-quinazolinone;
(+/−)-6-Fluoro-4-phenylethyl-4-trifluoromethyl-3,4-dihydro-2(1H)-quinazolinone;
(−)-6-Chloro-4-cyclopropylethynyl-4-trifluoromethyl-3,4-dihydro-2(1H)-quinazolinone;
(+)-6-Chloro-4-cyclopropylethynyl-4-trifluoromethyl-3,4-dihydro-2(1H)-quinazolinone;
(+)-4-Cyclopropylethynyl-5,6-difluoro-4-trifluoromethyl-3,4-dihydro-2(1H)-quinazolinone;
(−)-4-Cyclopropylethynyl-5,6-difluoro-4-trifluoromethyl-3,4-dihydro-2(1H)-quinazolinone;
(+)-E-4-Cyclopropylethynyl-5,6-difluoro-4-trifluoromethyl-3,4-dihydro-2(1H)-quinazolinone; and,
(−)-6-Chloro-4-E-cyclopropylethynyl-4-trifluoromethyl-3,4-dihydro-2(1H)-quinazolinone;
or a pharmaceutically acceptable salt thereof.

8. A pharmaceutical composition, comprising: a pharmaceutically acceptable carrier and a therapeutically effective amount of a compound of claim 1 or a pharmaceutically acceptable salt thereof.

9. A method for treating HIV infection, comprising: administering to a host in need of such treatment a therapeutically effective amount of a compound of claim 1, or a pharmaceutically acceptable salt form thereof.

10. A method of inhibiting HIV present in a body fluid sample which comprises treating the body fluid sample with an effective amount of a compound according to claim 1 or a salt form thereof.

11. A pharmaceutical composition, comprising: a pharmaceutically acceptable carrier and a therapeutically effective amount of a compound of claim 2 or a pharmaceutically acceptable salt form thereof.

12. A pharmaceutical composition, comprising: a pharmaceutically acceptable carrier and a therapeutically effective amount of a compound of claim 3 or a pharmaceutically acceptable salt form thereof.

13. A pharmaceutical composition, comprising: a pharmaceutically acceptable carrier and a therapeutically effective amount of a compound of claim 4 or a pharmaceutically acceptable salt form thereof.

14. A pharmaceutical composition, comprising: a pharmaceutically acceptable carrier and a therapeutically effective amount of a compound of claim 5 or a pharmaceutically acceptable salt form thereof.

15. A pharmaceutical composition, comprising: a pharmaceutically acceptable carrier and a therapeutically effective amount of a compound of claim 6 or a pharmaceutically acceptable salt form thereof.

16. A pharmaceutical composition, comprising: a pharmaceutically acceptable carrier and a therapeutically effective amount of a compound of claim 7 or a pharmaceutically acceptable salt form thereof.

17. A method for treating HIV infection, comprising: administering to a host in need of such treatment a therapeutically effective amount of a compound of claim 2, or a pharmaceutically acceptable salt form thereof.

18. A method for treating HIV infection, comprising: administering to a host in need of such treatment a therapeutically effective amount of a compound of claim 3, or a pharmaceutically acceptable salt form thereof.

19. A method for treating HIV infection, comprising: administering to a host in need of such treatment a therapeutically effective amount of a compound of claim 4, or a pharmaceutically acceptable salt form thereof.

20. A method for treating HIV infection, comprising: administering to a host in need of such treatment a therapeutically effective amount of a compound of claim 5, or a pharmaceutically acceptable salt form thereof.

21. A method for treating HIV infection, comprising: administering to a host in need of such treatment a therapeutically effective amount of a compound of claim 6, or a pharmaceutically acceptable salt form thereof.

22. A method for treating HIV infection, comprising: administering to a host in need of such treatment a therapeutically effective amount of a compound of claim 7, or a pharmaceutically acceptable salt form thereof.

23. A compound according to claim 7, wherein the compound is: (+/−)-6-chloro-4-cyclopropylethynyl-4-trifluoromethyl-3,4-dihydro-2(1H)-quinazolinone, or a pharmaceutically acceptable salt form thereof.

24. A compound according to claim 7, wherein the compound is: (+/−)-6-chloro-4-(2-pyridyl)ethynyl-4-trifluoromethyl-3,4-dihydro-2(1H)-quinazolinone, or a pharmaceutically acceptable salt form thereof.

25. A compound according to claim 7, wherein the compound is: (+/−)-6-chloro-4-phenylethynyl-4-trifluoromethyl-3,4-dihydro-2(1H)-quinazolinone, or a pharmaceutically acceptable salt form thereof.

26. A compound according to claim 7, wherein the compound is: (+/−)-4-cyclopropylethynyl-6-methoxy-4-trifluoromethyl-3,4-dihydro-2(1H)-quinazolinone, or a pharmaceutically acceptable salt form thereof.

27. A compound according to claim 7, wherein the compound is: (+/−)-6-methoxy-4-(2-pyridyl)ethynyl-4-trifluoromethyl-3,4-dihydro-2(1H)-quinazolinone, or a pharmaceutically acceptable salt form thereof.

28. A compound according to claim 7, wherein the compound is: (+/−)-6-methoxy-4-phenylethynyl-4-trifluoromethyl-3,4-dihydro-2(1H)-quinazolinone, or a pharmaceutically acceptable salt form thereof.

29. A compound according to claim 7, wherein the compound is: (+/−)-4-cyclopropylethynyl-5,6-difluoro-4-trifluoromethyl-3,4-dihydro-2(1H)-quinazolinone, or a pharmaceutically acceptable salt form thereof.

30. A compound according to claim 7, wherein the compound is: (+/−)-5,6-difluoro-4-(2-pyridyl)ethynyl-4-trifluoromethyl-3,4-dihydro-2(1H)-quinazolinone, or a pharmaceutically acceptable salt form thereof.

31. A compound according to claim 7, wherein the compound is: (+/−)-5,6-difluoro-4-phenylethynyl-4-trifluoromethyl-3,4-dihydro-2(1H)-quinazolinone, or a pharmaceutically acceptable salt form thereof.

32. A compound according to claim 7, wherein the compound is: (+/−)-4-cyclopropylethynyl-6-fluoro-4-trifluoromethyl-3,4-dihydro-2(1H)-quinazolinone, or a pharmaceutically acceptable salt form thereof.

33. A compound according to claim 7, wherein the compound is: (+/−)-6-fluoro-4-(2-pyridyl)ethynyl-4-trifluoromethyl-3,4-dihydro-2(1H)-quinazolinone, or a pharmaceutically acceptable salt form thereof.

34. A compound according to claim 7, wherein the compound is: (+/−)-6-fluoro-4-phenylethynyl-4-trifluoromethyl-3,4-dihydro-2(1H)-quinazolinone, or a pharmaceutically acceptable salt form thereof.

35. A compound according to claim 7, wherein the compound is: (+/−)-6-fluoro-4-(2'-2-pyridyl)ethyl-4-trifluoromethyl-3,4-dihydro-2(1H)-quinazolinone, or a pharmaceutically acceptable salt form thereof.

36. A compound according to claim 7, wherein the compound is: (+/−)-6-fluoro-4-phenylethyl-4-trifluoromethyl-3,4-dihydro-2(1H)-quinazolinone, or a pharmaceutically acceptable salt form thereof.

37. A compound according to claim 7, wherein the compound is: (−)-6-chloro-4-cyclopropylethynyl-4-trifluoromethyl-3,4-dihydro-2(1H)-quinazolinone, or a pharmaceutically acceptable salt form thereof.

38. A compound according to claim 7, wherein the compound is: (+-6-chloro-4-cyclopropylethynyl-4-trifluoromethyl-3,4-dihydro-2(1H)-quinazolinone, or a pharmaceutically acceptable salt form thereof.

39. A compound according to claim 7, wherein the compound is: (+)-4-cyclopropylethynyl-5,6-difluoro-4-trifluoromethyl-3,4-dihydro-2(1H)-quinazolinone, or a pharmaceutically acceptable salt form thereof.

40. A compound according to claim 7, wherein the compound is: (−)-4-cyclopropylethynyl-5,6-difluoro-4-trifluoromethyl-3,4-dihydro-2(1H)-quinazolinone, or a pharmaceutically acceptable salt form thereof.

41. A compound according to claim 7, wherein the compound is: (+)-E-4-cyclopropylethenyl-5,6-difluoro-4-trifluoromethyl-3,4-dihydro-2(1H)-quinazolinone, or a pharmaceutically acceptable salt form thereof.

42. A compound according to claim 7, wherein the compound is: (−)-6-chloro-4-E-cyclopropylethynyl-4-trifluoromethyl-3,4-dihydro-2(1H)-quinazolinone, or a pharmaceutically acceptable salt form thereof.

43. A pharmaceutical composition, comprising: a pharmaceutically acceptable carrier and a therapeutically effective amount of a compound of claim 37 or a pharmaceutically acceptable salt form thereof.

44. A pharmaceutical composition, comprising: a pharmaceutically acceptable carrier and a therapeutically effective amount of a compound of claim 39 or a pharmaceutically acceptable salt form thereof.

45. A pharmaceutical composition, comprising: a pharmaceutically acceptable carrier and a therapeutically effective amount of a compound of claim 41 or a pharmaceutically acceptable salt form thereof.

46. A pharmaceutical composition, comprising: a pharmaceutically acceptable carrier and a therapeutically effective amount of a compound of claim 42 or a pharmaceutically acceptable salt form thereof.

47. A method for treating HIV infection, comprising: administering to a host in need of such treatment a therapeutically effective amount of a compound of claim 37, or a pharmaceutically acceptable salt form thereof.

48. A method for treating HIV infection, comprising: administering to a host in need of such treatment a therapeutically effective amount of a compound of claim 39, or a pharmaceutically acceptable salt form thereof.

49. A method for treating HIV infection, comprising: administering to a host in need of such treatment a therapeutically effective amount of a compound of claim 41, or a pharmaceutically acceptable salt form thereof.

50. A method for treating HIV infection, comprising: administering to a host in need of such treatment a therapeutically effective amount of a compound of claim 42, or a pharmaceutically acceptable salt form thereof.

51. A compound according to claim 37, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

52. A compound according to claim 39, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

53. A compound according to claim 41, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

54. A compound according to claim 42, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

* * * * *

UNITED STATES PATENT AND TRADEMARK OFFICE
CERTIFICATE OF CORRECTION

PATENT NO. : 6,124,302
DATED : Sept. 26, 2000
INVENTOR(S) : Jeffrey W. Corbett; Soo S. Ko It is certified that error appears in the above-identified patent and that said Letters Patent is hereby corrected as shown below:

In column 1, line 55, please delete " glycoprotiens" and insert -- glycoproteins--.

In column 3, line 57, please delete "presnet inventionto" and insert -- present invention to --.

In column 4, line 13, please delete "effectivereverse" and insert -- effective reverse --.

In column 6, line 61, at the beginning of the line, please delete "(-)" and insert -- (+) --.

In column 8, line 13, please delete "ethlethynyl" and insert -- ethylethynyl --.

In column 9, line 17, please delete "sturcure" and insert -- structure --.

In column 10, line 24, please delete "atomatic" and insert -- aromatic --.

In column 11, line 14, at the end of the line, please delete "conventinal" and insert --conventional--.

In column 11, line 28, please delete "thses compunds" and insert --these compounds --.

In column 11, line 37, please delete "pharmaceutiaclly" and insert --pharmaceutically--.

UNITED STATES PATENT AND TRADEMARK OFFICE
CERTIFICATE OF CORRECTION

PATENT NO.   : 6,124,302
DATED        : Sept. 26, 2000
INVENTOR(S)  : Jeffrey W. Corbett; Soo S. Ko It is certified that error appears in the above-identified patent and that said Letters Patent is hereby corrected as shown below:

In column 12, line 6, please delete "substituten to" and insert --substituent is--.

In column 12, line 63, please delete "substututed" and insert --substituted--.

In column 15, line 37, please delete "enantimoer" and insert --enantiomer--.

In column 17, line 64, please delete "2-thynylpyridine" and insert --2-ethynylpyridine--.

In column 18, line 15, please delete "$R^4$=Ethyl" and insert --$R^4$ = Ethyl--.

In column 71, line 37, please delete "Ia" and insert --Ib--.

In column 72, line 19, please delete "Cyclopropylethynyl" and insert -- Cyclopropylethenyl --.

In column 72, line 21, please delete "cyclopropylethynyl" and insert -- cyclopropylethenyl --.

In column 74, line 9, please delete "(+" and insert --(+)--.

In column 74, line 25, please delete "cyclopropylethynyl" and insert -- cyclopropylethenyl --.

UNITED STATES PATENT AND TRADEMARK OFFICE
CERTIFICATE OF CORRECTION

PATENT NO. : 6,124,302
DATED : Sept. 26, 2000
INVENTOR(S) : Jeffrey W. Corbett; Soo S. Ko It is certified that error appears in the above-identified patent and that said Letters Patent is hereby corrected as shown below:

In the following columns and for the examples listed, please delete "C-C" and insert --C=C--.

| Column | Ex. |
|--------|-----|
| 33 | 44 |
| 34 | 47 |
| 34 | 58 |
| 34 | 60 |
| 34 | 71 |
| 35 | 128 |
| 36 | 207 |
| 36 | 227 |
| 37 | 293 |
| 38 | 319 |
| 38 | 381 |
| 39 | 387 |
| 39 | 398 |
| 39 | 449 |
| 40 | 479 |

UNITED STATES PATENT AND TRADEMARK OFFICE
CERTIFICATE OF CORRECTION

PATENT NO. : 6,124,302
DATED : Sept. 26, 2000
INVENTOR(S) : Jeffrey W. Corbett; Soo S. Ko It is certified that error appears in the above-identified patent and that said Letters Patent is hereby corrected as shown below:

In the following columns and for the examples listed, please delete "C-C" and insert --C=C--.

| | |
|---|---|
| 41 | 534 |
| 41 | 547 |
| 41 | 554 |
| 42 | 633 |
| 42 | 635 |
| 43 | 690 |
| 43 | 701 |
| 43 | 703 |
| 44 | 789 |
| 45 | 808 |
| 46 | 894 |
| 46 | 905 |
| 47 | 955 |
| 47 | 962 |
| 48 | 1043 |

UNITED STATES PATENT AND TRADEMARK OFFICE
CERTIFICATE OF CORRECTION

PATENT NO. : 6,124,302
DATED : Sept. 26, 2000
INVENTOR(S) : Jeffrey W. Corbett; Soo S. Ko It is certified that error appears in the above-identified patent and that said Letters Patent is hereby corrected as shown below:

In the following columns and for the examples listed, please delete "C-C" and insert --C=C--.

| Column | Line |
|---|---|
| 48 | 1061 |
| 49 | 1067 |
| 49 | 1078 |
| 49 | 1129 |
| 50 | 1135 |
| 50 | 1159 |
| 51 | 1214 |
| 51 | 1216 |
| 52 | 1295 |
| 53 | 1350 |
| 53 | 1370 |
| 54 | 1469 |
| 55 | 1475 |
| 55 | 1486 |
| 55 | 1499 |
| 55 | 1517 |
| 55 | 1537 |
| 57 | 1622 |

UNITED STATES PATENT AND TRADEMARK OFFICE
CERTIFICATE OF CORRECTION

PATENT NO.  : 6,124,302
DATED       : Sept. 26, 2000
INVENTOR(S) : Jeffrey W. Corbett; Soo S. Ko It is certified that error appears in the above-identified patent and that said Letters Patent is hereby corrected as shown below:

In column 2, line 17, please delete "deoxythymidinene" and insert --deoxythymidine --.

In column 2, line 64, at the end of the line, please delete "4((2-pyridy)" and insert --4((2-pyridyl)--.

In column 6, line 17, please delete "[5]" and insert --[6]--.

In column 11, line 66, please delete "contempleted" and insert --contemplated--.

In column 71, line 37, please delete "Ia" and insert --Ib--.

Signed and Sealed this

Eighth Day of May, 2001

Attest:

NICHOLAS P. GODICI

Attesting Officer

Acting Director of the United States Patent and Trademark Office